(12) United States Patent
Stairs et al.

(10) Patent No.: US 12,246,305 B2
(45) Date of Patent: Mar. 11, 2025

(54) SYSTEMS AND METHODS FOR CHROMATOGRAPHY USE AND REGENERATION

(71) Applicant: Regeneron Pharmaceuticals, Inc., Tarrytown, NY (US)

(72) Inventors: Robert Stairs, High Springs, FL (US); James Reilly, Putnam Valley, NY (US); John Mattila, Nyack, NY (US); Samantha Wadsworth, Stamford, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 315 days.

(21) Appl. No.: 17/753,915

(22) PCT Filed: Sep. 23, 2020

(86) PCT No.: PCT/US2020/052243
§ 371 (c)(1),
(2) Date: Mar. 18, 2022

(87) PCT Pub. No.: WO2021/061790
PCT Pub. Date: Apr. 1, 2021

(65) Prior Publication Data
US 2022/0323937 A1    Oct. 13, 2022

Related U.S. Application Data

(60) Provisional application No. 62/958,899, filed on Jan. 9, 2020, provisional application No. 62/905,033, filed on Sep. 24, 2019.

(51) Int. Cl.
*B01D 15/20* (2006.01)
*B01D 15/32* (2006.01)
(Continued)

(52) U.S. Cl.
CPC ........ *B01J 20/3475* (2013.01); *B01D 15/203* (2013.01); *B01D 15/327* (2013.01);
(Continued)

(58) Field of Classification Search
CPC ...... B01D 15/203; B01D 15/327; C07K 1/20; G01N 30/50
See application file for complete search history.

(56) References Cited

U.S. PATENT DOCUMENTS 6,927,004 B2   8/2005   Eurlings et al.
7,087,411 B2   8/2006   Daly et al.
(Continued)

FOREIGN PATENT DOCUMENTS

CN   104892734 A   9/2015
CN   105457612 A   4/2016
(Continued)

OTHER PUBLICATIONS

Ismail B.P. "Basic Principles of Chromatography", Food Analysis, 2017, pp. 185-211.
(Continued)

*Primary Examiner* — Bradley R Spies
(74) *Attorney, Agent, or Firm* — Bookoff McAndrews, PLLC

(57) ABSTRACT

Aspects of the present disclosure relate to a method of regenerating a hydrophobic interaction chromatography column to which a load mass has been applied, the method comprising passing one or more column volumes of an alkaline solution through hydrophobic interaction media within the column, wherein the alkaline solution exhibits a pH of between about 10 and about 14, and a conductivity of between 0.5 mS/cm and about 10 mS/cm, wherein material bound to the hydrophobic interaction media is removed. In some cases, the alkaline solution may include sodium
(Continued)

hydroxide at a concentration of between, e.g., about 0.1 mM and 10 mM.

24 Claims, 39 Drawing Sheets

(51) Int. Cl.
    *B01J 20/34*     (2006.01)
    *C07K 1/20*     (2006.01)
    *C07K 16/06*     (2006.01)

(52) U.S. Cl.
    CPC ............. *C07K 1/20* (2013.01); *C07K 16/065* (2013.01); *B01J 2220/58* (2013.01)

(56) References Cited

U.S. PATENT DOCUMENTS

| | | |
|---|---|---|
| 7,279,159 B2 | 10/2007 | Daly et al. |
| 7,582,298 B2 | 9/2009 | Stevens et al. |
| 7,879,984 B2 | 2/2011 | Martin et al. |
| 8,043,617 B2 | 10/2011 | Stevens et al. |
| 8,062,640 B2 | 11/2011 | Sleeman et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,079,948 B2 | 7/2015 | Orengo et al. |
| 9,132,192 B2 | 9/2015 | Daly et al. |
| 9,173,880 B2 | 11/2015 | Dix et al. |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,302,015 B2 | 4/2016 | Papadopoulos et al. |
| 9,402,898 B2 | 8/2016 | Walsh et al. |
| 2014/0044730 A1 | 2/2014 | Yancopoulos et al. |
| 2014/0088295 A1 | 3/2014 | Smith et al. |
| 2014/0271642 A1 | 9/2014 | Murphy et al. |
| 2014/0271653 A1 | 9/2014 | Gurnett-Bander et al. |
| 2014/0271658 A1 | 9/2014 | Murphy et al. |
| 2014/0271681 A1 | 9/2014 | Martin et al. |
| 2014/0275494 A1 | 9/2014 | Wang et al. |
| 2015/0203579 A1 | 7/2015 | Papadopoulos et al. |
| 2015/0203580 A1 | 7/2015 | Papadopoulos et al. |
| 2015/0259423 A1 | 9/2015 | Kirshner et al. |
| 2015/0266966 A1 | 9/2015 | Smith et al. |
| 2015/0313194 A1 | 11/2015 | Hu et al. |
| 2015/0337045 A1 | 11/2015 | Okamoto et al. |
| 2016/0075778 A1 | 3/2016 | Okamoto et al. |
| 2019/0263855 A1* | 8/2019 | Gadgil ............... C07K 1/22 |
| 2020/0002373 A1 | 1/2020 | Livigni et al. |

FOREIGN PATENT DOCUMENTS

| | | |
|---|---|---|
| CN | 107636005 A | 1/2018 |
| CN | 109843904 A | 6/2019 |
| EP | 3116645 A1 | 1/2017 |
| JP | 2006-512283 A | 4/2006 |
| JP | 2009244252 A | 10/2009 |
| WO | 2015035180 A1 | 3/2015 |
| WO | 2018/234543 A1 | 12/2018 |

OTHER PUBLICATIONS

Amersham Pharmacia Biotech, "Hydrophobic Interaction Chromatography Principles and Methods Edition AB," pp. 1-104 (2000).
International Search Report in International Application No. PCT/US2020/052243, mailed Mar. 15, 2021 (7 pages).
Ghose, S. et al., "Purification of monoclonal antibodies by hydrophobic interaction chromatography under no-salt conditions," mAbs, vol. 5, pp. 795-800 (2013).

* cited by examiner

SYSTEMS AND METHODS FOR CHROMATOGRAPHY USE AND REGENERATION

CROSS-REFERENCE TO RELATED APPLICATIONS

This application is a U.S. national stage filing under 35 U.S.C. § 371 of International Application No. PCT/US2020/052243, filed Sep. 23, 2020, which claims priority to U.S. Provisional Patent Application No. 62/905,033, filed on Sep. 24, 2019, and U.S. Provisional Patent Application No. 62/958,899, filed Jan. 9, 2020, both of which are hereby incorporated by reference in their entirety.

FIELD OF DISCLOSURE

The present disclosure relates to systems, methods, and solutions for the use and regeneration of chromatography media. Some aspects of the present disclosure relate to systems and methods incorporating a single-step hydrophobic interaction chromatography media regeneration solution.

INTRODUCTION

Chromatography is a widely used category of processes that may be performed in order to separate components of a mixture. Certain types of chromatography may be performed in drug product preparation processes (e.g., in separating, collecting, isolating, purifying, polishing etc. a molecule for use in a drug product). Some molecules of interest (e.g., polypeptides, polyribonucleotides, etc.) may need to be purified from e.g., materials of host cells in which they were produced. Separation or purification of molecules of interest using chromatography may reduce, remove, or separate host cell proteins (e.g., lipases), host cell materials (e.g., cell debris) and other impurities that could otherwise be co-purified with a molecule of interest.

Chromatography may include the use of a stationary phase including media configured to assist in separating components of a mobile phase passing through the stationary phase. For example, hydrophobic interaction chromatography (HIC) may separate molecules (e.g., polypeptides, polyribonucleotides, etc.) according to differences in surface hydrophobicity, by using a reversible interaction between the molecules and hydrophobic surfaces of a HIC medium in a stationary phase. The interaction between the molecules and the hydrophobic surfaces of HIC media may be affected by, e.g., salts in a running buffer. A load mass having a high salt concentration may be loaded into a HIC apparatus, where the high salt concentration encourages interaction between HIC media within the apparatus and the molecules in the mixture. Subsequently, solutions (e.g., buffers) having reduced ionic strength may be run through the HIC apparatus to reverse the hydrophobic interactions between the HIC media and the molecules. Molecules having the lowest hydrophobicity may elute first, and molecules having the greatest hydrophobicity may elute last, requiring a greater reduction in salt concentration to reverse their hydrophobic interactions with the HIC media.

In some cases, HIC media may be reused for multiple chromatography cycles. To maintain efficacy, quality, and cleanliness of HIC media, prevent contamination between cycles, increase longevity of HIC media, prevent buildup of impurities, and/or otherwise meet or exceed operating standards (e.g., operating standards internal to a laboratory or organization or operating standards mandated by a regulatory organization), methods for regenerating HIC media may be employed to remove residual material from the HIC media after a HIC cycle has been run.

SUMMARY

Aspects of the present disclosure relate to regenerating chromatography columns. In one aspect, the present disclosure is directed to a method of regenerating a hydrophobic interaction chromatography column to which a load mass has been applied. The method may include passing one or more column volumes of an alkaline solution through hydrophobic interaction media within the column, wherein the alkaline solution exhibits a pH of between about 10 and about 14, and a conductivity of between 0.5 mS/cm and about 10 mS/cm, wherein material bound to the hydrophobic interaction media is removed. The alkaline solution may include one of sodium hydroxide, potassium hydroxide, calcium hydroxide, magnesium hydroxide, or Tris; the alkaline solution may exhibit a conductivity of between about 0.8 mS/cm and about 1.6 mS/cm, and or the alkaline solution may include a total dissolved salt concentration of between about 0.1 mM and about 10 mM.

After the removal of material bound to the hydrophobic interaction media, less than 1.0% of the load mass may remain bound to the hydrophobic interaction media as a residual mass. The material removed from the media may include host cell proteins, suggested proteins, lipids, polypeptide fragments, biomolecules, or nucleic acids. The material removed from the media may, in some embodiments, not include bacteria or fungi. The method may, in some embodiments, not include contacting the hydrophobic interaction media with a chaotropic agent or an organic solvent. The step of passing the one or more column volumes of an alkaline solution through the hydrophobic interaction media within the column takes between about 10 minutes and about 1 hour.

In another aspect, the present disclosure is direct to a method of regenerating a chromatography column to which a load mass has been applied, the method comprising passing one or more column volumes of an alkaline solution through media within the column, wherein the alkaline solution includes sodium hydroxide at a total dissolved concentration of between about 0.5 mM and about 50 mM, wherein material bound to the media is removed. The media may include a matrix comprising ligands having between 2 and 10 hydrocarbons in an aliphatic or aromatic configuration. The ligands may be present in the media at a density of between about 20 and about 30 μmol per ml of media. In other examples, the media may include no ligands including 30 or more hydrocarbons; the chromatography column may not be used in a mixed-mode chromatography process; and/or the media may include a matrix comprising cross-linked agarose and phenyl ligands. In other examples, the method may not include contacting the media with alcohol, ethylene glycol, or sodium chloride. The method may further comprise after passing the one or more column volumes of the alkaline solution through the column, passing one or more column volumes of a chaotropic agent through the column, wherein the chaotropic agent is one of 6N guanidine hydrochloride or 8N urea. The method may further include contacting the column with a storage buffer comprising sodium hydroxide at a total dissolved concentration of between about 0.05M and about 0.15M. The method may also include applying a first load mass to the chromatography column, and applying a second load mass to the chromatography column, wherein the method does not include cleaning the chromatography column.

In another aspect, the present disclosure is directed to a method of identifying a concentration of an alkaline solution for a hydrophobic interaction chromatography column regeneration solution, the method comprising passing a volume of a first solution through hydrophobic interaction media within the column, wherein the first solution includes water and a concentration of an alkaline solution beginning from about 0N and increasing at an approximately constant rate to a maximum concentration; passing a volume of a second solution through the hydrophobic interaction media, wherein the second solution includes water and a concentration of an alkaline solution beginning from the maximum concentration and decreasing at an approximately constant rate to about 0N; and identifying a portion of the first or second solution that, when passing through the hydrophobic interaction media, removes material bound to the hydrophobic interaction media. The alkaline solution may include sodium hydroxide and the maximum concentration may be about 1N. In other examples, the volume of the first solution and the volume of the second solution are about 20 column volumes each.

In another aspect, the present disclosure includes predicting, evaluating, or comparing usability of and regeneration of various chromatography resins. In some examples, a method of evaluating a chromatography protocol includes: in a filter plate well, adding a load mass containing a target molecule to a volume of chromatography media and collecting a flowthrough from the filter plate well, wherein the load mass exhibits the protocol pH; adding a plurality of aliquots of a buffer with the chromatography media to obtain an eluent from the chromatography media, wherein the buffer exhibits the buffer pH and a concentration of a kosmotropic salt decreases linearly over the plurality of aliquots, and wherein a first quantity of the target molecule is included in the flowthrough and the eluent combined; adding a second solution to the chromatography media to extract a second quantity of the target molecule from the chromatography media; and adding a chaotropic agent to the chromatography media to extract a third quantity of the target molecule from the chromatography media.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments. Any features of an embodiment or example described herein (e.g., composition, formulation, method, etc.) may be combined with any other embodiment or example, and all such combinations are encompassed by the present disclosure. Moreover, the described systems and methods are neither limited to any single aspect nor embodiment thereof, nor to any combinations or permutations of such aspects and embodiments. For the sake of brevity, certain permutations and combinations are not discussed and/or illustrated separately herein.

DETAILED DESCRIPTION

Figure 1:
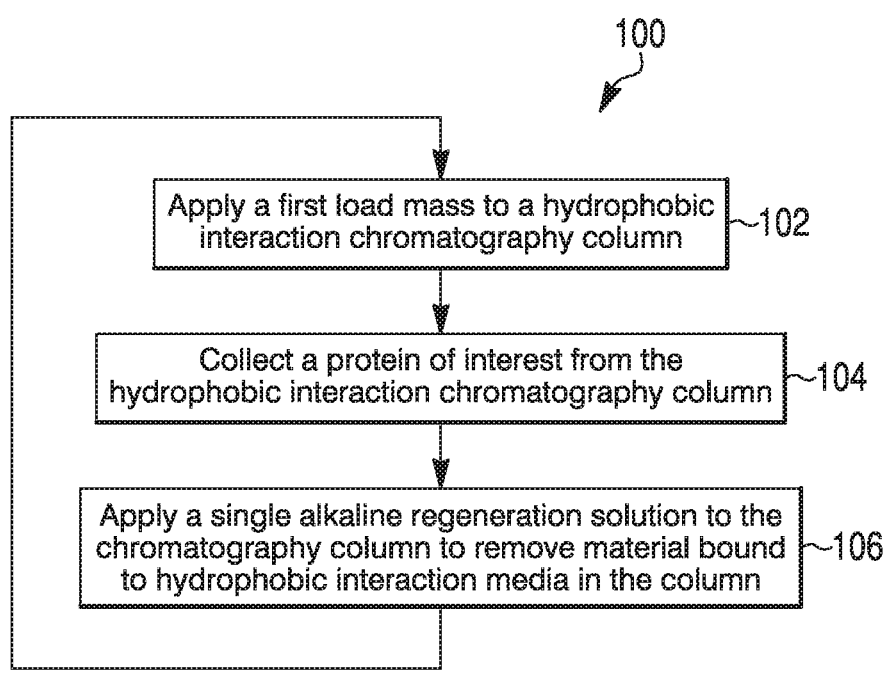
FIG. 1 depicts, in flow-chart form, an exemplary method according to aspects of the present disclosure.

Unless defined otherwise, all technical and scientific terms used herein have the same meaning as is commonly understood by one of ordinary skill in the art to which this disclosure belongs. Although any suitable methods and materials (e.g., similar or equivalent to those described herein) can be used in the practice or testing of the present disclosure, particular methods are now described. All publications mentioned are hereby incorporated by reference.

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." For the terms "for example" and "such as," and grammatical equivalences thereof, the phrase "and without limitation" is understood to follow unless explicitly stated otherwise.

As used herein, the term "about" is meant to account for variations due to experimental error. When applied to numeric values, the term "about" may indicate a variation of +/−5% from the disclosed numeric value, unless a different variation is specified. As used herein, the singular forms "a," "an," and "the" include plural referents unless the context clearly dictates otherwise. Further, all ranges are understood to be inclusive of endpoints, e.g., from 1 centimeter (cm) to 5 cm would include lengths of 1 cm, 5 cm, and all distances between 1 cm and 5 cm.

It should be noted that all numeric values disclosed herein (including all disclosed values, limits, and ranges) may have a variation of +/−5% from the disclosed numeric value unless a different variation is specified.

The term "polypeptide" as used herein refers to any amino acid polymer having more than about 20 amino acids covalently linked via amide bonds. Proteins contain one or more amino acid polymer chains (e.g., polypeptides). Thus, a polypeptide may be a protein, and a protein may contain multiple polypeptides to form a single functioning biomolecule.

Post-translational modifications may modify or alter the structure of a polypeptide. For example, disulfide bridges (e.g., S—S bonds between cysteine residues) may be formed post-translationally in some proteins. Some disulfide bridges are essential to proper structure, function, and interaction of polypeptides, immunoglobulins, proteins, co-factors, substrates, and the like. In addition to disulfide bond formation, proteins may be subject to other post-translational modifications, such as lipidation (e.g., myristoylation, palmitoylation, farnesoylation, geranylgeranylation, and glycosylphosphatidylinositol (GPI) anchor formation), alkylation (e.g., methylation), acylation, amidation, glycosylation (e.g., addition of glycosyl groups at arginine, asparagine, cysteine, hydroxylysine, serine, threonine, tyrosine, and/or tryptophan), and phosphorylation (i.e., the addition of a phosphate group to serine, threonine, tyrosine, and/or histidine). Post-translational modifications may affect the hydrophobicity, electrostatic surface properties, or other properties which determine the surface-to-surface interactions participated in by the polypeptide.

As used herein, the term "protein" includes biotherapeutic proteins, recombinant proteins used in research or therapy, trap proteins and other Fc-fusion proteins, chimeric proteins, antibodies, monoclonal antibodies, human antibodies, bispecific antibodies, antibody fragments, antibody-like molecules, nanobodies, recombinant antibody chimeras, cytokines, chemokines, peptide hormones, and the like. A protein of interest (POI) may include any polypeptide or protein that is desired to be isolated, purified, or otherwise prepared. POIs may include polypeptides produced by a cell, including antibodies.

The term "antibody," as used herein, includes immunoglobulins comprised of four polypeptide chains: two heavy (H) chains and two light (L) chains inter-connected by disulfide bonds. Typically, antibodies have a molecular weight of over 100 kDa, such as between 130 kDa and 200 kDa, such as about 140 kDa, 145 kDa, 150 kDa, 155 kDa, or 160 kDa. Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3.

A class of immunoglobulins called Immunoglobulin G (IgG), for example, is common in human serum and comprises four polypeptide chains—two light chains and two heavy chains. Each light chain is linked to one heavy chain via a cystine disulfide bond, and the two heavy chains are bound to each other via two cystine disulfide bonds. Other classes of human immunoglobulins include IgA, IgM, IgD, and IgE. In the case of IgG, four subclasses exist: IgG 1, IgG 2, IgG 3, and IgG 4. Each subclass differs in their constant regions, and as a result, may have different effector functions. In some embodiments described herein, a POI may comprise a target polypeptide including IgG. In at least one embodiment, the target polypeptide comprises IgG 4.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Target molecules (such as target polypeptides/antibodies) may be produced using recombinant cell-based production systems, such as the insect bacculovirus system, yeast systems (e.g., *Pichia* sp.), or mammalian systems (e.g., CHO cells and CHO derivatives like CHO-K1 cells). The term "cell" includes any cell that is suitable for expressing a recombinant nucleic acid sequence. Cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, bacculovirus-infected insect cells, Trichoplusiani, etc.), non-human animal cells, human cells, or cell fusions such as, for example, hybridomas or quadromas. In some embodiments a cell may be a human, monkey, ape, hamster, rat, or mouse cell. In some embodiments, a cell may be eukaryotic and may be selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, a cell may comprise one or more viral genes, e.g. a retinal cell that expresses a viral gene (e.g., a PER.C6™ cell).

The term "target molecule" may be used herein to refer to target polypeptides (e.g., antibodies, antibody fragments, or other proteins or protein fragments), or to other molecules intended to be produced, isolated, purified, and/or included in drug products (e.g., adeno-associated viruses (AAVs) or other molecules for therapeutic use). While methods according to the present disclosure may refer to target polypeptides, they may be as applicable to other target molecules. AAVs, for example, may be prepared according to suitable methods (e.g., depth filtration, affinity chromatography, and the like), and mixtures including AAVs may be subjected to methods according to the present disclosure. Before or after following one or more methods of the present disclosure, mixtures including AAVs may be subjected to additional procedures (e.g., to the removal of "empty cassettes" or AAVs that do not contain a target sequence).

In some embodiments, the target molecule is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

In some embodiments, a target molecule (e.g., an antibody) is selected from a group consisting of an anti-Programmed Cell Death 1 antibody (e.g., an anti-PD1 antibody as described in U.S. Pat. Appln. Pub. No. US2015/ 0203579A1), an anti-Programmed Cell Death Ligand-1 (e.g. an anti-PD-L1 antibody as described in in U.S. Pat. Appln. Pub. No. US2015/0203580A1), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g. an anti-AngPtl3 antibody as described in U.S. Pat. No. 9,018,356), an anti-platelet derived growth factor receptor antibody (e.g. an anti-PDGFR antibody as described in U.S. Pat. No. 9,265,827), an anti-Prolactin Receptor antibody (e.g., anti-PRLR antibody as described in U.S. Pat. No. 9,302,015), an anti-Complement 5 antibody (e.g., an anti-O5 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/ 0259423A1), an anti-Proprotein Convertase Subtilisin Kexin-9 antibody (e.g., an anti-PCSK9 antibody as described in U.S. Pat. No. 8,062,640 or U.S. Pat. Appln. Pub. No. US2014/0044730A1), an anti-Growth And Differentiation Factor-8 antibody (e.g., an anti-GDF8 antibody, also known as anti-myostatin antibody, as described in U.S. Pat. Nos. 8,871,209 or 9,260,515), an anti-Glucagon Receptor (e.g., anti-GCGR antibody as described in U.S. Pat. Appln. Pub. Nos. US2015/0337045A1 or US2016/ 0075778A1), an anti-VEGF antibody, an anti-IL1R antibody, an interleukin 4 receptor antibody (e.g., an anti-IL4R antibody as described in U.S. Pat. Appln. Pub. No. US2014/ 0271681A1 or U.S. Pat No. 8,735,095 or 8,945,559), an anti-interleukin 6 receptor antibody (e.g., an anti-IL6R antibody as described in U.S. Pat. No. 7,582,298, 8,043,617 or 9,173,880), an anti-interleukin 33 (e.g., anti-IL33 antibody as described in U.S. Pat. Appln. Pub. Nos. US2014/ 0271658A1 or US2014/0271642A1), an anti-Respiratory syncytial virus antibody (e.g., anti-RSV antibody as described in U.S. Pat. Appln. Pub. No. US2014/ 0271653A1), an anti-Cluster of differentiation 3 (e.g., an anti-CD3 antibody, as described in U.S. Pat. Appln. Pub. Nos. US2014/0088295A1 and US20150266966A1, and in U.S. Application No. 62/222,605), an anti-Cluster of differentiation 20 (e.g., an anti-CD20 antibody as described in U.S. Pat. Appln. Pub. Nos. US2014/0088295A1 and US20150266966A1, and in U.S. Pat. No. 7,879,984), an anti-Cluster of Differentiation-48 (e.g., anti-CD48 antibody as described in U.S. Pat. No. 9,228,014), an anti-Fel d1 antibody (e.g., as described in U.S. Pat. No. 9,079,948), an anti-Middle East Respiratory Syndrome virus (e.g., an anti-MERS antibody), an anti-Ebola virus antibody (e.g., Regeneron's REGN-EB3), an anti-CD19 antibody, an anti-CD28 antibody, an anti-IL1 antibody, an anti-IL2 antibody, an anti-IL3 antibody, an anti-IL4 antibody, an anti-IL5 antibody, an anti-IL6 antibody, an anti-IL7 antibody, an anti-Erb3 antibody, an anti-Zika virus antibody, an anti-Lymphocyte Activation Gene 3 (e.g., anti-LAG3 antibody or anti-CD223 antibody) and an anti-Activin A antibody. Each U.S. patent and U.S. patent publication mentioned in this paragraph is incorporated by reference in its entirety.

In some embodiments, a target molecule (e.g., a bispecific antibody) is selected from the group consisting of an anti-CD3×anti-CD20 bispecific antibody, an anti-CD3×anti-Mucin 16 bispecific antibody, and an anti-CD3×anti-Prostate-specific membrane antigen bispecific antibody. In some embodiments, the target molecule is selected from the group consisting of alirocumab, sarilumab, fasinumab, nesvacumab, dupilumab, trevogrumab, evinacumab, and rinucumab.

In some embodiments, the target molecule is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is incorporated by reference in its entirety), or a VEGF trap (e.g., aflibercept or ziv-aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159, both of which are incorporated by reference in their entireties). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

Embodiments of the present disclosure may be used in the preparation of various drug products, or in developing methods to purify various drug products. In some embodiments, the present disclosure may be useful in the preparation or purification of drug products including an antigen-binding molecule or an AAV. In some aspects, embodiments of the present disclosure may be suitable for use in the preparation of drug products including ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-1a, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

The term "hydrophobic interaction media" or "HIC media" means a combination of a support structure and a hydrophobic moiety, wherein the hydrophobic moiety is affixed to the support structure. The media can be in the form of chromatography media, e.g., beads or other particles held in a packed bed column format, in the form of a membrane, or in any format that can accommodate a liquid comprising a protein of interest and contaminants. Thus, support structures include agarose beads (e.g., sepharose), silica beads, cellulosic membranes, cellulosic beads, hydrophilic polymer beads, resins, and the like. The hydrophobic moiety binds to hydrophobic molecules and hydrophobic surfaces of proteins. The degree of hydrophobicity of the media can be controlled by selecting the hydrophobic moiety. Hydrophobic interaction media is employed in a process known as hydrophobic interaction chromatography (HIC) and is used to separate target molecules, such as proteins of interest or other molecules, from product and process related contaminants. When target molecules are manufactured in and/or purified from host cells, some product and process related components from which they should eventually be separated are referred to as host cell proteins (HCP) and cellular debris. In some cases, a mixture containing the target molecules and other components is applied to the HIC media in a buffer designed to promote binding of hydrophobic groups in the target molecule to the hydrophobic moiety of the HIC medium. Such a mixture may be referred to as a "load mass." HIC exploits hydrophobic differences between the target molecule(s) and impurities that result in separation during load, wash, or regeneration phases. Often, the target molecules are separated into the flow through while impurities are bound to the HIC medium. HIC may also be operated in a mode where target molecule binds to the HIC medium while HCP and cellular debris fail to bind and flow through. The present disclosure may be applicable in either case (whether a target molecule does or does not bind to the hydrophobic interaction moiety.

HIC media may be periodically stripped or regenerated after its use in purifying/collecting a target molecule. As used herein, the terms "stripping" and "regenerating," are used interchangeably and/or in combination to refer to processes configured to remove any residual components of a load mass from HIC media after a purification cycle and prepare the HIC media for a subsequent purification cycle. For example, after a HIC apparatus is used to separate or purify a molecule of interest from a load mass including host cell materials (e.g., host cell debris, host cell proteins, etc.) and the molecule of interest is eluted from the HIC apparatus, the HIC media may be regenerated to remove residual materials (e.g., host cell materials, host cell proteins, lipids, residual polypeptides, aggregated proteins, nucleic acids, biomolecules, etc.) from the HIC media and prepare the HIC media to be used in purifying the molecule of interest from another load mass. In some embodiments, regeneration of the HIC media may include disrupting hydrophobic interactions between residual host cell materials and/or target molecules and the HIC media, and/or denaturing residual host cell materials. Regeneration may be performed in between HIC cycles to "reset" the HIC media without the need for more lengthy cleaning processes. In some embodiments, regeneration may be performed in between HIC cycles to prevent or reduce discoloration of HIC media over time. In some embodiments, a regeneration process according to the present disclosure may take between, e.g., about 5 minutes and about an hour, such as between about 10 minutes and about 1 hours, between about 10 minutes and about 45 minutes, or between about 10 minutes and about 30 minutes. Preferably, regeneration of the HIC media may be completed without subjecting the HIC media to more robust cleaning solutions that may have unwanted effects or raise additional concerns. Regeneration processes may be configured without a particular focus on, e.g., removal of bacteria, fungi, or other microbes from chromatography media.

"Stripping" and "regenerating" may be distinguished from, e.g., "cleaning" chromatography media. Cleaning may include processes intended to thoroughly disinfect and/or decontaminate chromatography media, a chromatography apparatus, and/or a laboratory setting. For example, cleaning processes may include the use of antibiotic, antifungal, or otherwise antimicrobial solutions, other disinfecting solutions, sterilization, and the like, in concentrations and amounts intended to sanitize and/or sterilize chromatography media or a chromatography apparatus. In contrast, while regeneration may in some cases include the use of solutions having antimicrobial properties, a main intention of regeneration may be to remove residual components of a load mass from chromatography media after a purification process. In some embodiments, additional safeguards or procedures may be needed during and/or after a cleaning process to ensure that subsequent chromatography cycles are not affected by disinfecting, sanitization, antimicrobial, or antibiotic solutions used during the cleaning process. In many cases, cleaning processes may be lengthier than regeneration processes (e.g., greater than about an hour).

Separation of molecules in HIC media may be accomplished by, e.g., exposing the HIC media to a load mass having a high salt concentration to increase hydrophobic interactions between the HIC media and target molecules in the load mass, and subsequently passing a volume of a solution (e.g., a buffer) having a decreased or decreasing salt concentration through the HIC media to reverse the hydrophobic interactions. Therefore, it is conventionally understood that less material will bind to HIC media in low- or no-salt conditions. However, surprisingly, it has been discovered that certain types of HIC media exhibit increased binding (e.g., hydrophobic interactions) to residual materials (e.g., host cell proteins) under no-salt conditions. Further, it has been discovered that some proteins (e.g., monoclonal antibodies) may denature onto some types of HIC media (e.g., Capto™ Phenyl (High Sub) media (GE Healthcare Life Sciences). While the proteins may return to their native configurations once eluted from HIC media, such proteins in their denatured states may not be removed from HIC media by regeneration procedures including, e.g., reverse osmosis deionized water (RODI), 1N sodium hydroxide, and/or 20% ethanol. It is hypothesized that, in some cases, elution of molecules from HIC media is dependent on pH and/or conductivity.

Aspects of the present disclosure relate to a regeneration solution, and to evaluation of chromatography media for usability, including ease of regeneration.

In some embodiments of the present disclosure, a regeneration solution may be an alkaline solution. It is contemplated that, in some embodiments of the present disclosure, high pH may be a driving factor in effectiveness of a regeneration solution; however, it is further contemplated that in some cases, effectiveness of a high pH may be counteracted with high ionic strength. In some embodiments, therefore, efficacy of a regeneration solution may be driven by a high pH combined with low, but non-zero, conductivity. (See, e.g., Example 14, discussed below.) For example, in some embodiments, a regeneration solution may exhibit a pH of between about 8 and about 14, such as between about 10 and about 14. In some embodiments, a regeneration solution may exhibit a generally low conductivity. For example, in some embodiments, a regeneration solution may exhibit a conductivity of between about 0.5 mS/cm and about 10 mS/cm, such as between about 0.5 mS/cm and about 5 mS/cm, between about 5.0 mS/cm and about 10 mS/cm, between about 0.5 mS/cm and about 3 mS/cm, between about 0.5 mS and about 1.6 mS, between about 0.8 mS/cm and about 1.6 mS/cm, about 0.5 mS/cm, about 1.0 mS/cm, about 1.5 mS/cm, about 2.0 mS/cm, about 2.5 mS/cm, about 3 mS/cm, about 3.5 mS/cm, about 4.0 mS/cm, about 4.5 mS/cm, or about 5.0 mS/cm.

In some embodiments, a regeneration solution may be an alkaline solution including a concentration of, e.g., sodium hydroxide, potassium hydroxide, calcium hydroxide, magnesium hydroxide, Tris, other alkaline solution, or a combination thereof. In some embodiments, a regeneration solution may include a total dissolved salt concentration of between about 0.1 mM and about 50 mM, such as between about 0.1 mM and about 25 mM, between about 0.1 mM and about 20 mM, between about 0.1 mM and about 15 mM, between about 0.1 mM and about 10 mM, between about 0.1 mM and about 5 mM, between about 0.1 mM and about 2.5 mM, between about 1 mM and about 10 mM, between about 1 mM and about 7 mM, between about 2.5 mM and about 5 mM, or between about 2.5 mM and about 7 mM, such as about 0.5 mM, about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 15 mM, about 20 mM, or about 25 mM.

In some embodiments, regeneration solutions according to the present disclosure may be suitable for using in single-step regeneration processes. That is, in some embodiments, a method of regenerating HIC media may include contacting the HIC media with a single solution, where the solution exhibits one or more of the properties described herein, and wherein after being contacted with the single solution, less than about 5% of the load mass remains bound to the HIC media as a residual mass. For example, in some embodiments, a method of regenerating HIC media may include contacting the HIC media with a solution exhibiting a pH of between about 10 and about 14, and a conductivity of between about 0.5 mS/cm and about 10 mS/cm, after which less than about 5% of the load mass remains bound to the HIC media as a residual mass. In some embodiments, the residual mass may be less than about 4%, less than about 3%, less than about 2% or less than about 1% of the load mass.

The volume of regeneration solution used according to the present disclosure may be any suitable volume. In some embodiments, e.g., in which a load mass is applied to HIC media in a chromatography column, a volume of regeneration solution used according to the present disclosure may be measured in column volumes (CV). In some embodiments, for example, a method of regenerating HIC media in a chromatography column may include passing at least one CV of a regeneration solution through the column. In some embodiments, the method may include passing between about 1 and about 20 column volumes of a regeneration solution through the column, such as between about 1 column volume and about 15 column volumes, between about 1 column volume and about 10 column volumes, between about 1 column volume and about 5 column volumes, between about 3 column volumes and about 17 column volumes, between about 5 column volumes and about 15 column volumes, or between about 5 column volume and about 10 column volumes, such as about 1 column volume, about 2 column volumes, about 3 column volumes, about 4 column volumes, about 5 column volumes, about 6 column volumes, about 7 column volumes, about 8 column volumes, about 9 column volumes, about 10 column volumes, about 12 column volumes, about 14 column volumes, about 16 column volumes, about 18 column volumes, or about 20 column volumes.

Systems and methods according to the present disclosure may be applicable to a variety of separation media and/or processes. A single system, method, or solution of the present disclosure may share characteristics with more than one embodiment described herein. In some exemplary embodiments, systems and methods according to the present disclosure may be applicable to media and/or processes in which components of a load mass are separated based fully or partly on their hydrophobicity, such as HIC, or to media/processes using a combination of hydrophobicity and electrical charge, such as ion exchange/hydrophobic interaction mixed mode chromatography. In some embodiments, one or more regeneration solutions and/or methods disclosed herein may be combined with (e.g., implemented before or after) other regeneration solutions and/or methods. For example, a regeneration solution of the present disclosure may be applied to media used in mixed mode chromatography, in order to strip the media of residual mass interacting with the media due to hydrophobicity. Another regeneration solution may also be applied to the media, in order to strip the media of residual mass bound to the media due to charge.

In some embodiments, regeneration solutions and/or methods disclosed herein may be applicable to HIC media having a high degree of hydrophobicity. In some embodiments, chromatography media that may be used with solutions and methods according to the present disclosure may include, e.g., hydrophobic matrices comprising cross-linked agarose, polystyrene divinylbenzene, or polymethacrylate. In some embodiments, the matrices may include ligands having between 2 and 10 hydrocarbons in an aliphatic or aromatic configuration. In some embodiments, the matrices do not include ligands including 30 or more hydrocarbons. In some embodiments, for example, the ligands may include phenyl ligands, butyl ligands, or octyl ligands. In some embodiments, the ligands may be present in the media at a density of between about 20 and about 30 µmol per ml of media. In some embodiments, methods and regeneration solutions described herein may be applied specifically to regenerate HIC media. In some embodiments, methods and regeneration solutions described herein may be suited for, e.g., Capto™ Phenyl (High Sub), Capto™ Butyl, or Capto™ Octyl media (GE Healthcare Life Sciences), Phenyl Sepharose® media (GE Healthcare Life Sciences), POROS™ Benzyl and POROS™ Ethyl HIC resins (Thermo Scientific™), or TOYOPEARL™ resins. In some embodiments, methods and regeneration solutions described herein may be suited for use in continuous (multi-column) HIC systems and methods, such as those disclosed in U.S. Appln. Pub. No. US2020/0002373A1, which is incorporated by reference herein. For example, single-step regeneration solutions according to the present disclosure may be used in a multi-column continuous HIC setup, in which the efficiency of a single-step regeneration solution may enhance the overall efficiency of the multi-column setup. In some embodiments, methods and regeneration solutions described herein may be useful in HIC systems and methods including low- or no-kosmotrope conditions.

In some embodiments, regeneration processes according to the present disclosure may be performed without the use of reverse osmosis deionized water (RODI), organic solvents (e.g., ethanol or ethylene glycol), chaotropic agents (e.g., guanidine or urea), sodium chloride, and/or concentrations of sodium hydroxide over 50 mM. Advantageously, regeneration processes using solutions disclosed herein may not require additional processes to dispose of, e.g., solvents, such as ethanol (e.g., 20% ethanol) and chaotropic agents such as guanidine and urea (e.g., 6N guanidine or 6N urea). In some embodiments, however, it is contemplated that regeneration solutions disclosed herein may be used before, after, or in combination with an organic solvent (e.g., 20% ethanol) or a chaotropic agent (e.g., 6N guanidine or 6N urea).

In some embodiments, methods according to the present disclosure may include passing a regeneration solution disclosed herein through a chromatography column prior to contacting the chromatography column with a storage buffer, for storage purposes. A storage buffer may include, e.g., sodium hydroxide or another salt at a concentration of between about 0.05M and about 0.15M.

In some embodiments, methods according to the present disclosure may include evaluating various chromatography media to identify whether one or more chromatography media is likely to present challenges to use or regeneration of the media during purification of a target molecule. Evaluation of a chromatography media according to this disclosure may include, for example and without limitation, use of one or more chromatography media types, maintaining pH conditions, and a target molecule. Advantageously, methods according to the present disclosure may include screening on a scale smaller than is performed generally to purify a target molecule, allowing for significant savings of sample quantity (e.g., using approximately ⅒, ¹⁄₁₀₀, ¹⁄₅₀₀, ¹⁄₇₀₀ or less of the sample quantity needed to evaluate a chromatography media, such as for HIC, according to conventional methods. Further, multiple purification schemes having different variables (e.g., different combinations and types of media, pH, and/or target molecule) may be screened simultaneously using, e.g., a high-throughput screening (HTS) process. Alternatively, or in addition to high-throughput screening (HTS), elution assays may be used to exclude parameters of a potential HIC protocol.

Advantageously, these screening techniques and assays may result in significant time savings in identifying purification schemes suitable for use in large-scale purification processes, for example by optimizing a HIC unit operation. For example, an HTS process performed according to the present disclosure may be about ten times faster, fifty times faster, sixty times faster, seventy times faster, or even faster than conventional means of identifying regeneration/usability challenges in chromatography protocols for one or more unit operations, including HIC, ion exchange, affinity, and more.

Evaluation methods according to the present disclosure may include packing a well, such as a filter plate well, with an amount of chromatography media, where the chromatography media is intended for use in a potential purification scheme. The filter plate well may have a capacity of, e.g., less than 5 mL, such as less than 4 mL, less than 3 mL, or less than 2 mL. In some embodiments, the filter plate well may have a capacity of about 1 mL, about 0.8 mL, about 0.5 mL, or any other suitable capacity. The filter plate well may be fitted with a filter having a suitable mesh size, such as between about 0.5 and about 1.5 microns, such as about 0.8 microns, about 1.0 microns, or about 1.2 microns. The filter mesh size may depend upon the size of the resin beads present in a chromatography media to be used in the protocol. The size of such chromatography resin beads may be, e.g., between about 40 microns and about 120 microns, such as between about 50 microns and about 100 microns, between about 60 microns and about 90 microns, between about 80 microns and about 90 microns, about 70 microns, about 80 microns, about 90 microns, about 100 microns, or about 110 microns. The amount of chromatography media packed into the well may vary. For example, the amount of chromatography media may range from, e.g., about 2.0 µL to about 50.0 µL, such as about 10 µL, about 20.0 µL, about 30.0 µL, or about 40.0 µL. In some methods according to the present disclosure, a filter plate including multiple wells may be packed with a plurality of different chromatography media for simultaneous evaluation of multiple protocols in an array. This could be used for any chromatography step in a purification scheme, including for HIC, ion exchange, affinity, and more.

A volume of load material may be loaded into the packed filter plate well (or, in the case of multiple protocols being evaluated simultaneously, into each packed filter plate well). The load material may include a target molecule that has undergone some initial purification process, such as affinity chromatography or ion exchange chromatography. The load material may be used according to the present disclosure for testing a unit operation, such as HIC. In the case of multiple conditions for a single unit operation being evaluated simultaneously, load materials for use in different wells may include different target molecules. The load material may be titrated to a protocol-specific pH. The approximate concentration of target molecule within the load material may be adjusted to any suitable unit operation-specific concentration. In some embodiments, the volume of load material may correspond to a load mass (e.g., mass of the target molecule within the load material) that is a fraction of the load mass that would be used in a full-scale HIC protocol, such as ½, ⅕, ⅛, 1/10, 1/20, 1/50, 1/100 or less of the load mass used in a full-scale protocol.

Methods of evaluating a protocol for a unit operation may further include performing elution and wash steps suitable for use in large-scale processes (e.g., including the use of RODI, 1N sodium hydroxide, and/or 5 mM sodium hydroxide), and subsequently performing a stripping step using a caustic or chaotropic agent, such as 6N guanidine HCl or 6N urea, or a solvent, such as 20% ethanol. The elution/wash steps may be performed using, e.g., an elution buffer titrated to a protocol-specific pH. In the case of multiple protocols for a unit operation being evaluated, elution buffers exhibiting different protocol-specific pH values may be used in different wells in a single array. An elution step may include, e.g., exposing loaded chromatography media in a filter plate well to a gradient of elution buffer (beginning at a relatively higher concentration and ending at a concentration of 0). In another embodiment, an elution step may include exposing the loaded chromatography media to a buffer having an initial concentration of a kosmotropic salt (e.g., 500 mM, 400 mM, 300 mM, 200 mM, or the like of citrate), and gradually/linearly decreasing the concentration buffer to 0. In some embodiments, a pseudo-gradient elution may be performed, where the loaded chromatography media is exposed to discrete volumes of elution buffer having a linearly decreasing concentration, from a starting concentration (e.g., 300 mM) to 0 across multiple steps (e.g., 4, 5, 6, 7, 8, more, or fewer steps).

The first step may include any process intended for testing as a unit operation protocol. Generally, the first step may include applying solutions deemed suitable for use in large-scale and repeated operations (e.g., solutions that do not present safety or toxicity concerns). For example, the first step may include a wash or washes of RODI and/or 1N NaOH, applied in series, or in an alternating sequence, one time or multiple times each. The second step may include any solution intended to strip any remaining material bound to chromatography media after completion of the unit operation protocol being evaluated. Such regeneration processes are described elsewhere herein, but in general may include chaotropic agents, such as 6N guanidine HCl or 6N urea, or solvents, such as 20% ethanol.

Evaluation methods according to the present disclosure may include measuring the amount of a target molecule recovered during, e.g., the wash/elution steps and the stripping step. These results may be compared amongst various chromatography media. It may be preferable to have a relatively large percentage of target molecule recovered during the wash/elution steps (i.e., during a HIC protocol being tested), as opposed to during the stripping step (i.e., the rigorous stripping of a chromatography media).

Evaluation methods according to the present disclosure may further include determining a target molecule's recovery during a stripping step, as a percentage of the total target molecule recovered during the unit operation protocol being tested. If the percentage recovery of the target molecule during the stripping step is above a predetermined threshold, then the unit operation protocol may be predicted to potentially cause regeneration/reusability challenges when scaled up and/or when repeated many times. If the percentage recovery of the target molecule during the stripping step is at or below a predetermined threshold, then that unit operation protocol may be predicted to not cause regeneration/reusability challenges when scaled up and/or repeated. The predetermined threshold may be any experimentally-determined threshold indicative of an amount of residue left bound to chromatography media after a unit operation, such as a HIC protocol. In some embodiments, the predetermined threshold may be between, e.g., about 1% and about 10%, such as between about 3% and about 7%, such as about 4%, about 5%, or about 6%.

In embodiments in which multiple chromatography protocols are evaluated simultaneously, the above-described calculation of target molecule percentage recovery may be determined for multiple chromatography protocols at once, resulting in an initial impression of which protocol may be suitable or prioritized for further use, testing, investigation, or development. Protocols for further study may include wells for which a normalized percentage recovery attributable to the stripping step can be less than or equal to 1%, less than or equal to 3%, less than or equal to 5%, less than or equal to 7%, or less than or equal to 10%.

In some embodiments, methods of evaluating a chromatography protocol, such as for a HIC unit operation, according to the present disclosure may be performed in the early stages of developing a purification process. For example, a plurality of HIC protocols may be evaluated as described herein (e.g., high-throughput screening and/or elution assay), and HIC protocols that are predicted to pose regeneration/reusability challenges may be excluded or deprioritized for further study. Chromatography protocols that are not predicted to pose regeneration/reusability challenges may be subjected to further testing (e.g., full-scale testing) or study, to, e.g., maximize yield and minimize impurities, confirm that they meet internal and external quality control guidelines, and assess repeatability and longevity (e.g., whether they result in column discoloration or other undesirable effects after 10, 25, 50, 75, 100 or more cycles).

In some embodiments, methods according to the present disclosure advantageously may prevent or reduce discoloration of regeneration columns, media, and/or equipment that otherwise might arise after one or more uses (see, e.g., Examples 6 and 9 discussed herein). In some embodiments, methods according to the present disclosure may advantageously assist early on in identifying protocols for chromatography unit operations that may present regeneration/usability challenges, thus saving time and expense that may be incurred in developing a full purification scheme only to find out that the protocol for that chromatography step presents such challenges at a later time.

Reference will now be made to specific figures. FIG. 1 depicts a method 100 of regenerating a chromatography column according to aspects of the present disclosure. According to step 102, a first load mass may be applied to a hydrophobic interaction chromatography column. According to step 104, a protein of interest may be collected from the hydrophobic interaction chromatography column. According to step 106, a single alkaline regeneration solution may be applied to the chromatography column to remove material bound to hydrophobic interaction media in the column.

According to step 102, a first load mass may be applied to a hydrophobic interaction chromatography column. The load mass may include a target molecule (e.g., a polypeptide) as well as residual components, such as host cell proteins, cellular debris, and the like. According to step 104, a protein of interest may be collected from the hydrophobic interaction chromatography column. This may be done in, e.g., a wash step or an elution step. According to step 106, a single alkaline regeneration solution may be applied to the chromatography column to remove material bound to hydrophobic interaction media in the column. The single alkaline regeneration solution may have one or more of the characteristics described above.

EXAMPLES

Example 1

An amount of non-esterified free fatty acids ("NEFA") in several sample solutions was measured after incubation with Polysorbate 20 ("PS20"). The presence and amount of NEFA in a sample are taken to be indicative of PS20 degradation caused by, e.g., impurities, such as host cell proteins, in the sample. A first sample was taken from a HIC load mass. Five additional samples were taken from HIC pools after 1, 2, 3, 5, and 10 subsequent cycles. All the samples were incubated for the same amount of time. As shown in Table 1 below, from cycle 1 to cycle 5, the PS20 degradation was calculated to be a negative percentage, equivalent to a negative control. A negative PS20 degradation percentage corresponds to no detectable NEFA, and as such, no detectable lipase activity. NEFA was detectable between cycles 5 and 10, showing an increase in lipase activity. This data indicates that lipase activity may increase as a function of cycling.

TABLE 1

| Cycle | PS20 Degradation (%) | Detection |
| --- | --- | --- |
| Load mass | 1.83 | Detectable |
| Cycle 1 | −0.31 | Equivalent to negative control |
| Cycle 2 | −0.25 | Equivalent to negative control |
| Cycle 3 | −0.20 | Equivalent to negative control |
| Cycle 5 | −0.22 | Equivalent to negative control |
| Cycle 10 | 0.47 | Detectable |

Example 2

Figure 2:
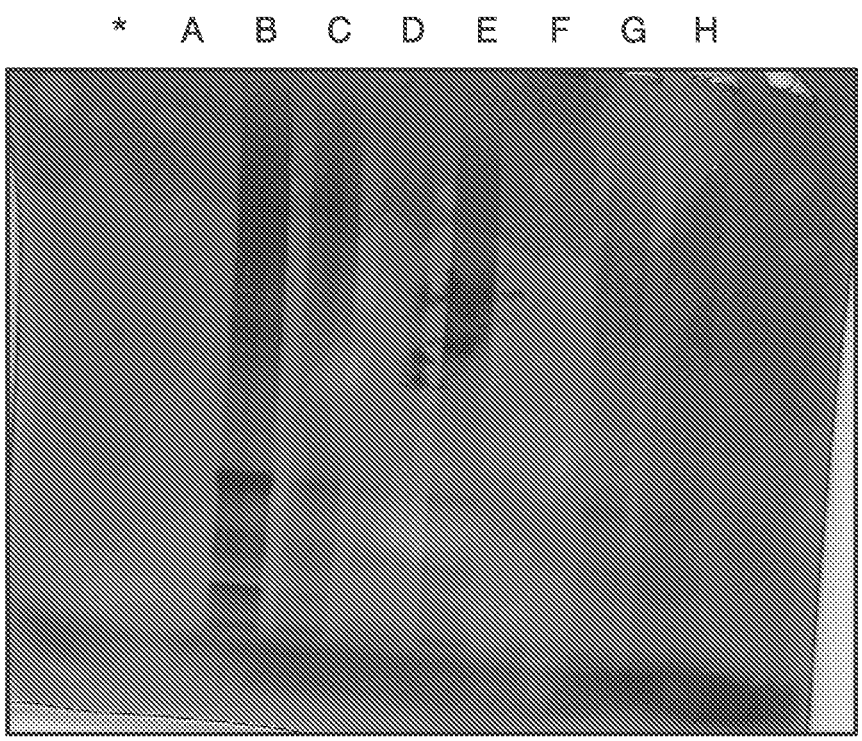
FIG. 2 depicts a blot analysis of chromatography columns in various states of use, according to aspects of the present disclosure.

FIG. 2 depicts a blot analysis of HIC media (Capto™ Phenyl (High Sub) (GE Healthcare Life Sciences)) in various states of use or post-exposure to regeneration solutions, as detailed below.

TABLE 2

| Label | Media state |
| --- | --- |
| * | Reference |
| A | Representative of naïve (unused) media |
| B | Used media |
| C | Used media exposed to 20% ethanol |
| D | Used media exposed to 70% ethanol |
| E | Used media exposed to 30% IPA |
| F | Used media exposed to 6N guanidine HCl |
| G | Used media exposed to 8N urea |
| H | Used media exposed to 2% (w/w) polysorbate 80 |

As can be seen in FIG. 2, darkened areas are visible for each column that has been used, except for the column that has been contacted with 6N guanidine HCl (column F). The column representative of naïve media (column A) also shows no darkened areas. This data indicates that 6N guanidine HCl is able to remove residual media during regeneration of a chromatography column, as compared to other solutions. 6N guanidine HCl is therefore of use as a stripping agent and as an agent that may be used subsequent to other stripping/regeneration agents, to evaluate efficacy of such other agents.

Example 3

Figure 3:
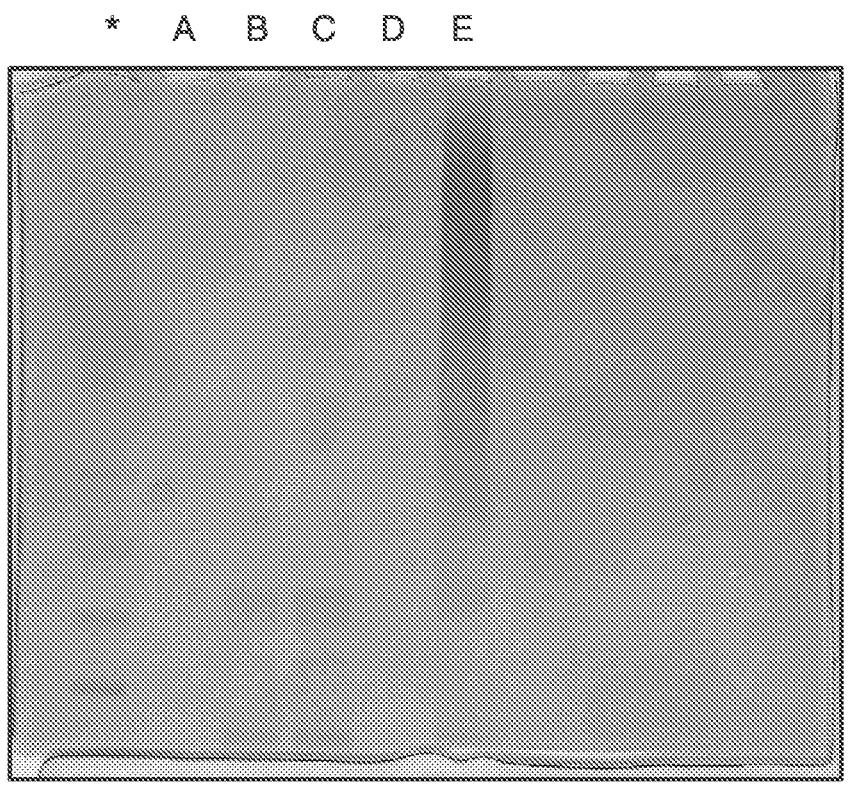
FIG. 3 depicts a blot analysis of chromatography columns in various states of use, according to aspects of the present disclosure.

FIG. 3 depicts a blot analysis of HIC media (Capto™ Phenyl (High Sub)) in various states of use or post-exposure to regeneration solutions, as detailed below.

TABLE 3

| Label | Media state |
| --- | --- |
| * | Reference Ladder |
| A | Representative of naïve (unused) media |
| B | Used media exposed to 10 cycles of a mixture containing a mAb A at a pH of 5.5, each cycle including a regeneration paradigm of RODI, 1.0N NaOH, RODI, and 20% ethanol |
| C | Used media exposed to 10 cycles of a mixture containing a mAb A at a pH of 8,, each cycle including a regeneration paradigm of RODI, 1.0N NaOH, RODI, and 20% ethanol |
| D | Used media exposed to a mixture containing a mAb A followed by 6N guanidine HCl |
| E | Used media exposed to 100 cycles of a mixture containing a mAb B, each cycle including a regeneration paradigm of RODI, 1.0N NaOH, RODI, and 20% ethanol |

Table 3 lists the types of media used and what, if any regenerating agents, the media were exposed to. As can be seen in FIG. 3, the ability of the regeneration paradigm including RODI, 1.0N NaOH, RODI, and 20% ethanol (used in media B and C) to remove residue from the media was not as complete as the ability of 6N guanidine HCl (D) to remove residue from the media.

Example 4

Figure 4:
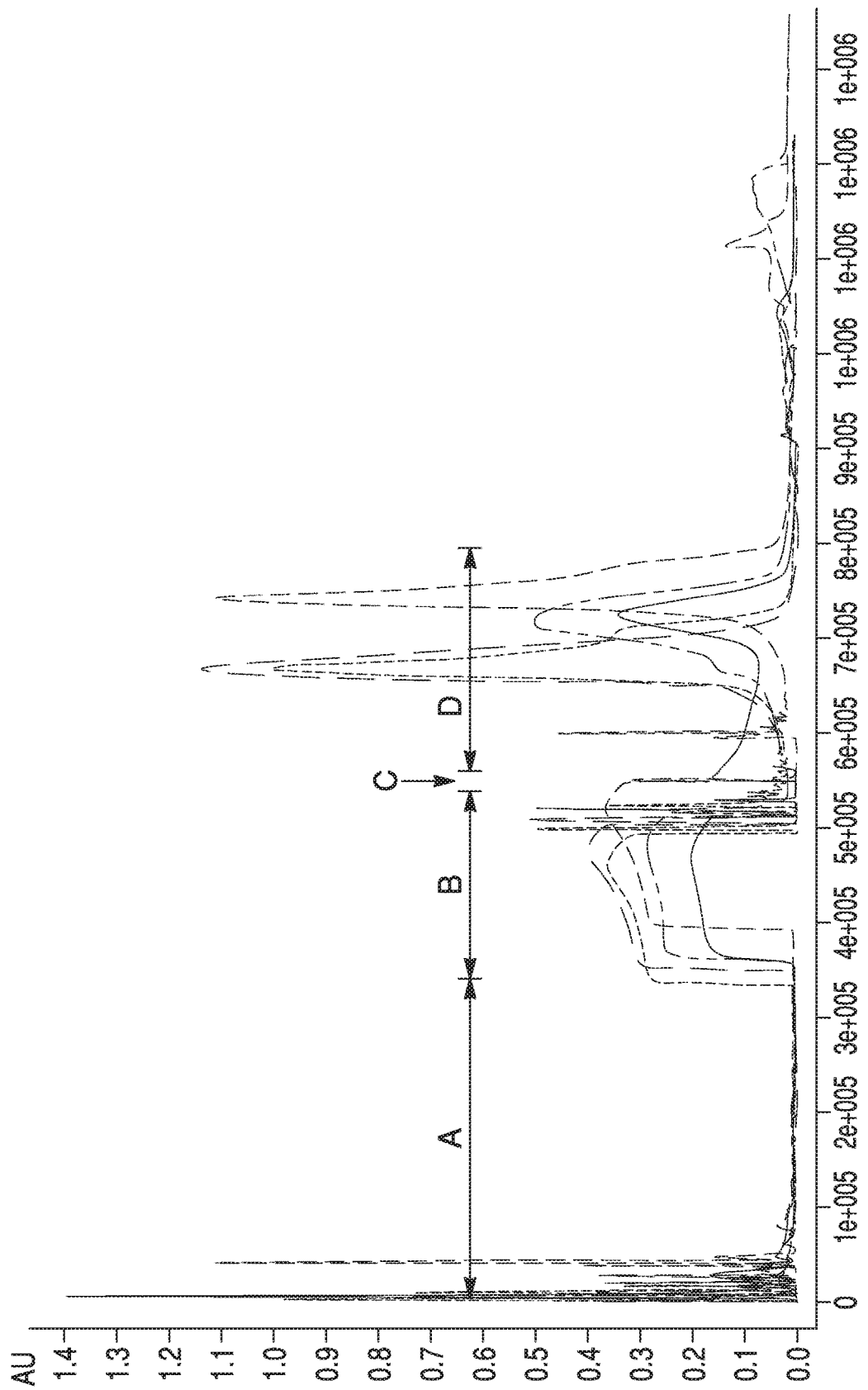
FIG. 4 depicts an overlay of chromatographic data from multiple processes, according to aspects of the present disclosure.

FIG. 4 depicts overlaid UV chromatograms depicting five sanitization procedures following collection of a monoclonal antibody mAb 1 during a process. Each sanitization procedure included a two-column-volume first 0.5N sodium hydroxide flush (A), followed by a pause, and then a one-column-volume second 0.5N sodium hydroxide flush (B). Sanitization was considered to be completed at point C, after which a two-column-volume water for injection ("WFI") flush was performed (D). As can be seen in FIG. 4, the first sodium hydroxide flush (A) produced high absorbances in the early portion of the flush, correlating to a large removal of impurities. The maximum absorbance seen during HIC elution (regeneration) is 2.4 AU, while the maximum absorbance seen during the sanitization cycles of FIG. 4 was approximately 1.4 AU.

Example 5

Figure 5:
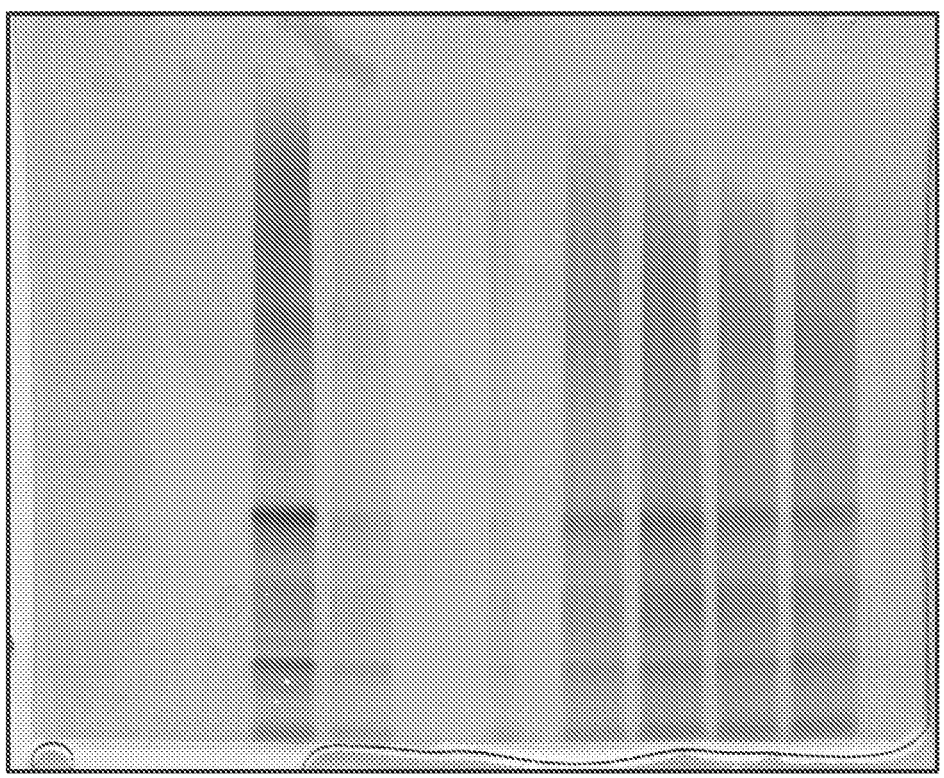
FIG. 5 depicts a blot analysis of chromatography columns in various states of use, according to aspects of the present disclosure.

FIG. 5 depicts a blot analysis of HIC media (Capto™ Phenyl (High Sub)) in various states of use or after exposure to stripping solutions, as detailed below. Specifically, used HIC media was exposed to decreasing concentrations of guanidine.

TABLE 4

| Label | Media state |
|---|---|
| * | Reference Ladder |
| A | Representative of naïve (unused) media |
| B | Used media |
| C | Used media exposed to 20% ethanol |
| D | Used media exposed to 6N guanidine |
| E | Used media exposed to 3N guanidine |
| F | Used media exposed to 2N guanidine |
| G | Used media exposed to 1N guanidine |
| H | Used media exposed to 0.5N guanidine |
| I | Used media exposed to 0.1N guanidine |

As can be seen in FIG. 5, the use of 6N guanidine HCl (D) removed the most residue from the HIC media, whereas solutions having lower concentrations of guanidine, and a solution of 20% ethanol, were not as effective in removal of residue from the HIC media.

Example 6

Figure 6:
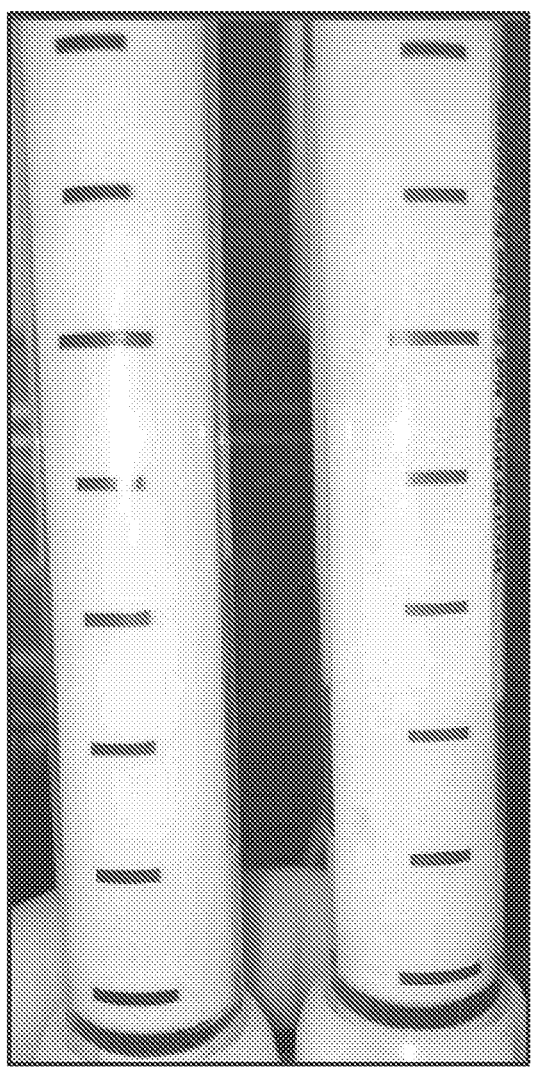
FIG. 6 depicts a comparison of a column containing hydrophobic interaction media subjected to multiple hydrophobic interaction chromatography cycles and a column containing unused hydrophobic interaction media, according to aspects of the present disclosure.

FIG. 6 depicts two columns containing Capto™ Phenyl (High Sub) HIC media (GE Life Sciences). The left-hand column was exposed to 49 cycles of HIC, for purifying a monoclonal antibody mAb 2. Each cycle included regeneration of the column with a sequence of RODI, 1N sodium hydroxide, RODI, and 20% ethanol. After the 40$^{th}$ cycle, a yellow band was identified at the bottom of the column. The right-hand column, as a comparison, is representative of naïve Capto™ Phenyl (High Sub) HIC media. Discoloration of the left-hand column may be indicative of insufficient regeneration.

Pools from cycles 1 and 49 were collected and analyzed for lipase activity and presence of host cell protein (HCP). There was no significant trend in lipase activity or HCP values between cycle 1 and cycle 49.

Example 7

Figure 7A:
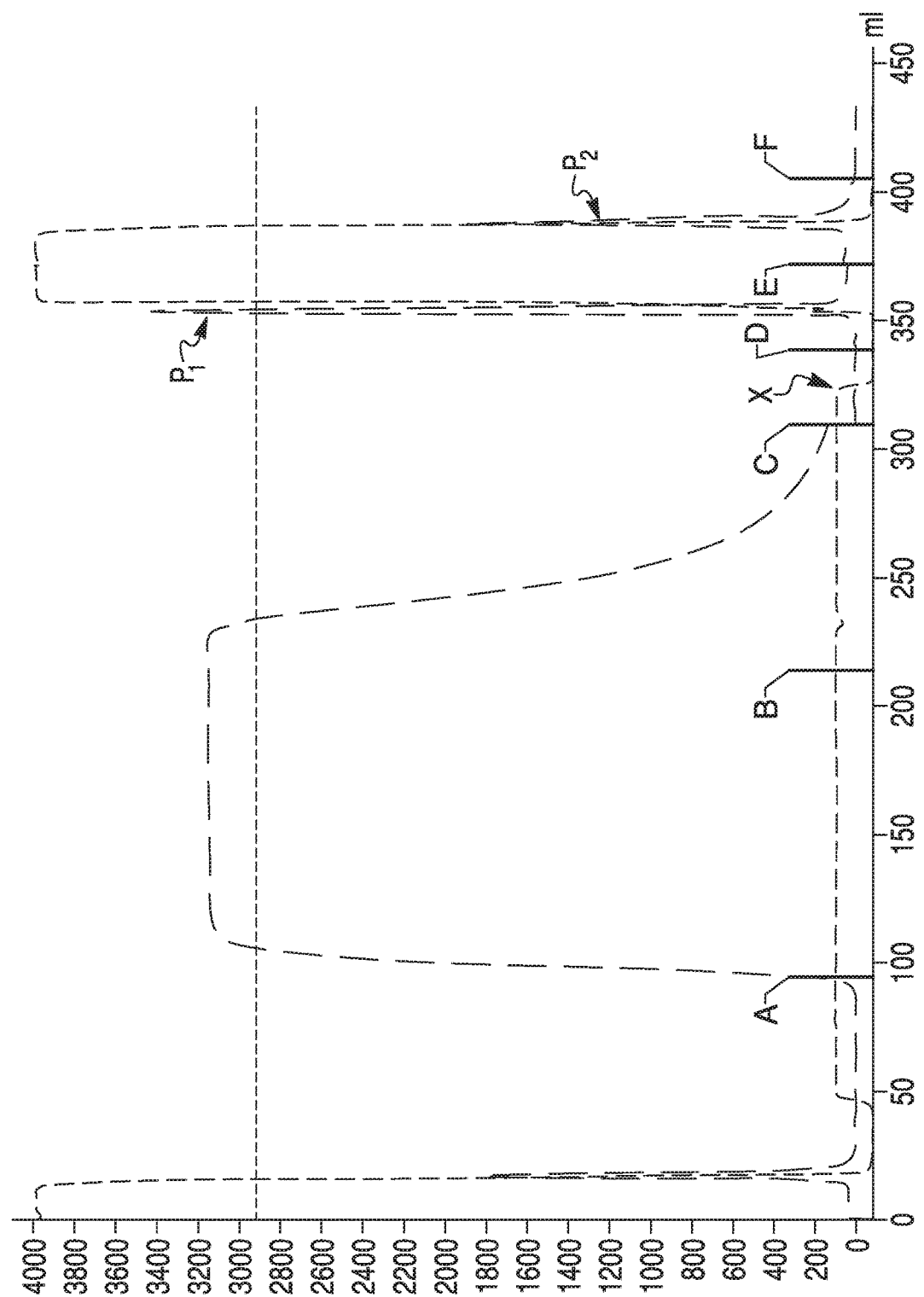
FIGS. 7A and 7B depict chromatograms of regeneration processes following hydrophobic interaction chromatography, the processes including the use of reverse osmosis deionized water, according to aspects of the present disclosure.
Figure 7B:
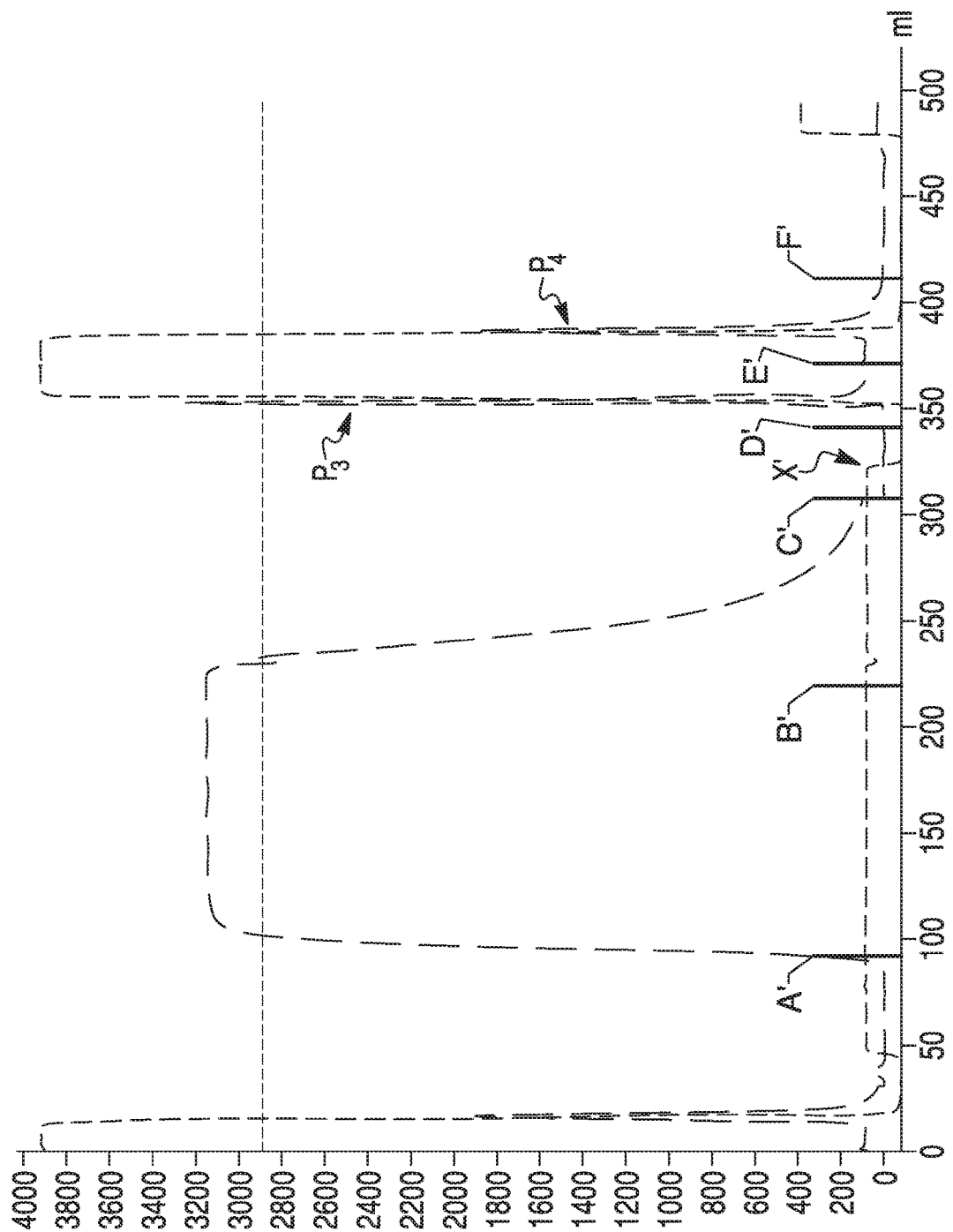

FIGS. 7A and 7B depict chromatograms of cycles 2 and 49, respectively, performed on the left-hand column described with respect to Example 6. FIGS. 7A and 7B are annotated as follows:

TABLE 5

| Cycle 2 (FIG. 7A) | | Cycle 49 (FIG. 7B) | |
|---|---|---|---|
| Marker | Event | Marker | Event |
| A | Pool collection begun | A' | Pool collection begun |
| B | Wash | B' | Wash |
| C | RODI strip | C' | RODI strip |
| D | 1N NaOH strip | D' | 1N NaOH strip |
| E | RODI strip | E' | RODI strip |
| F | 20% EtOH strip | F' | 20% EtOH strip |

In both cycle 2 and cycle 49, RODI was not an effective stripping solution, as shown by an absence of any peak following C or C' (at markers X and X'). The introduction of 1N NaOH created peaks $P_1$ (Cycle 2) and $P_3$ (Cycle 49), meaning that 1N NaOH was at least partially effective as a stripping solution. The introduction of the second RODI strip removed some additional impurities and produced peaks $P_2$ (Cycle 2) and $P_4$ (cycle 49). The introduction of 20% ethanol solution produced no additional peak. This data from both cycles indicates that RODI is not an effective stripping solution when used prior to sodium hydroxide.

Example 8

Figure 8A:
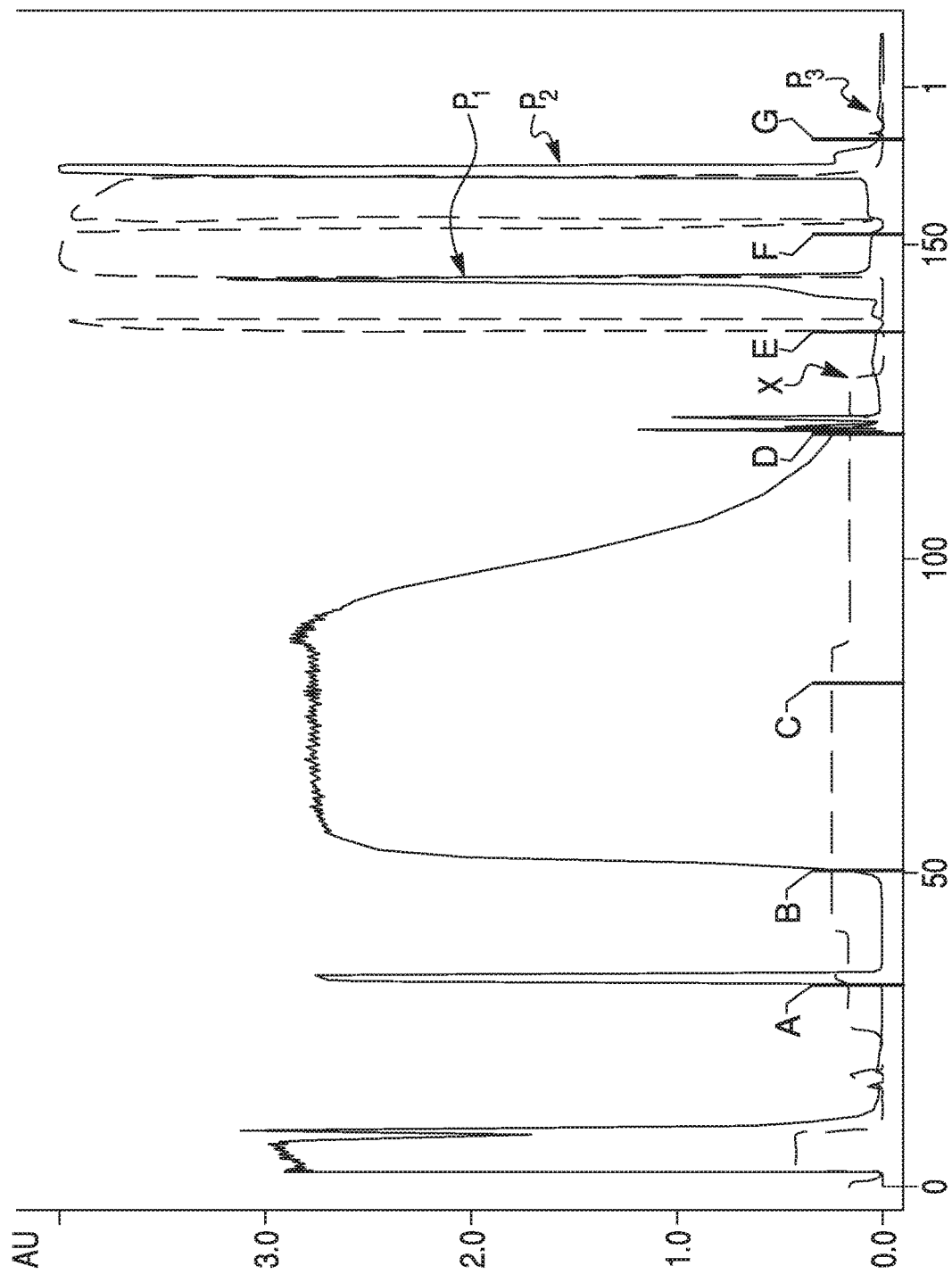
FIGS. 8A and 8B depict additional chromatograms of regeneration processes following hydrophobic interaction chromatography.
Figure 8B:
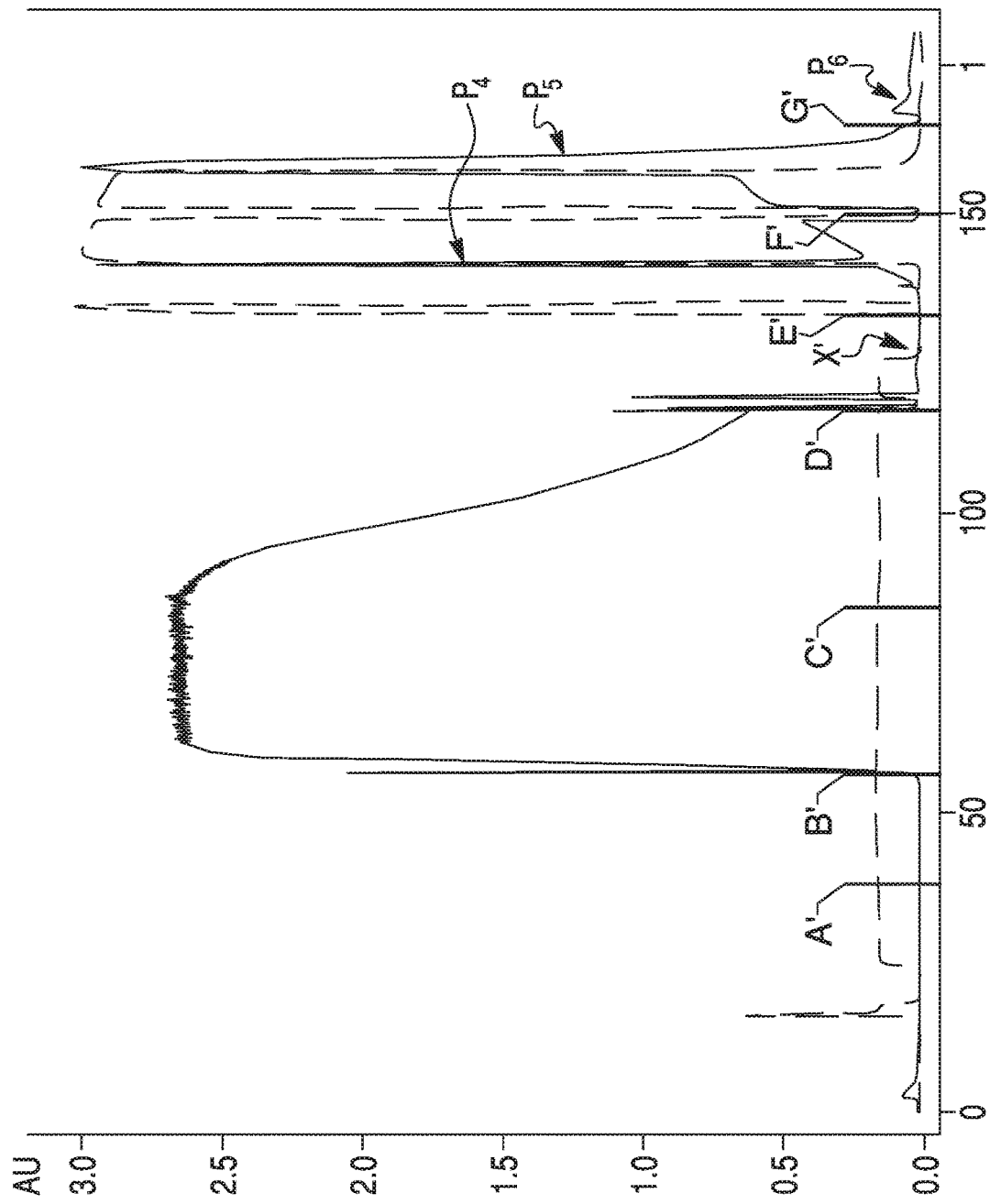

Two load masses, each including a target monoclonal antibody, were subjected to hydrophobic interaction chromatography processes. In a first process, after load, wash, and elution of a target monoclonal antibody mAb 3 from the first load mass, the chromatography column was subjected to a 1N sodium hydroxide stripping solution, followed by a RODI strip, and a 20% ethanol strip. In a second process, after load, wash, and elution of the target monoclonal antibody mAb 4 from the second load mass, the chromatography column was subjected to a RODI strip, followed by a 1N sodium hydroxide strip, another RODI strip, and a 20% ethanol strip. FIG. 8A depicts a chromatogram for the first process, and FIG. 8B depicts a chromatogram for the second process. Each chromatogram has been annotated as follows:

TABLE 6

| First Process (FIG. 8A) | | Second Process (FIG. 8B) | |
|---|---|---|---|
| Marker | Event | Marker | Event |
| A | Load | A' | Load |
| B | Pool collection begun | B' | Pool collection begun |
| C | Wash | C' | Wash |
| D | Pool collection ended | D' | RODI strip |
| E | 1N NaOH strip | E' | 1N NaOH strip |
| F | RODI strip | F' | RODI strip |
| G | 20% Ethanol strip | G' | 20% Ethanol strip |

Following the first RODI strip indicated by marker D' in FIG. 8B (at marker X'), there is a lack of any peak, comparable to the lack of the peak at the position shown by marker X in FIG. 8A (in which no first RODI strip was performed). Thus, the decreased conductivity of the first RODI strip applied in the first process did not cause the removal of any appreciable quantity of material from the chromatography column.

Example 9

The effectiveness of 6N guanidine HCl as a stripping solution and as a potential solution for removing discoloration on the left-hand column depicted in FIG. 6 was further evaluated. The column was subjected to the protocol described in the below table. A chromatogram was generated during the protocol, depicted in FIG. 9.

TABLE 7

| Solution | Flow Direction | Chromatogram Marker |
|---|---|---|
| RODI | Down flow | A |
| 6N guanidine HCl | Down flow | B |
| RODI | Down flow | C |
| 6N guanidine HCl* | Up flow | D |
| RODI | Up flow | E |

Each solution was moved through the column at a rate of 200 cm/hour in either a down flow direction (i.e., in the same direction as a HIC purification process would flow) or an up flow direction (i.e., opposite to the down flow, or "backwards" through the column). The second application of 6N guanidine HCl (indicated by an asterisk) was held within the column for approximately 16 hours.

Figure 9:
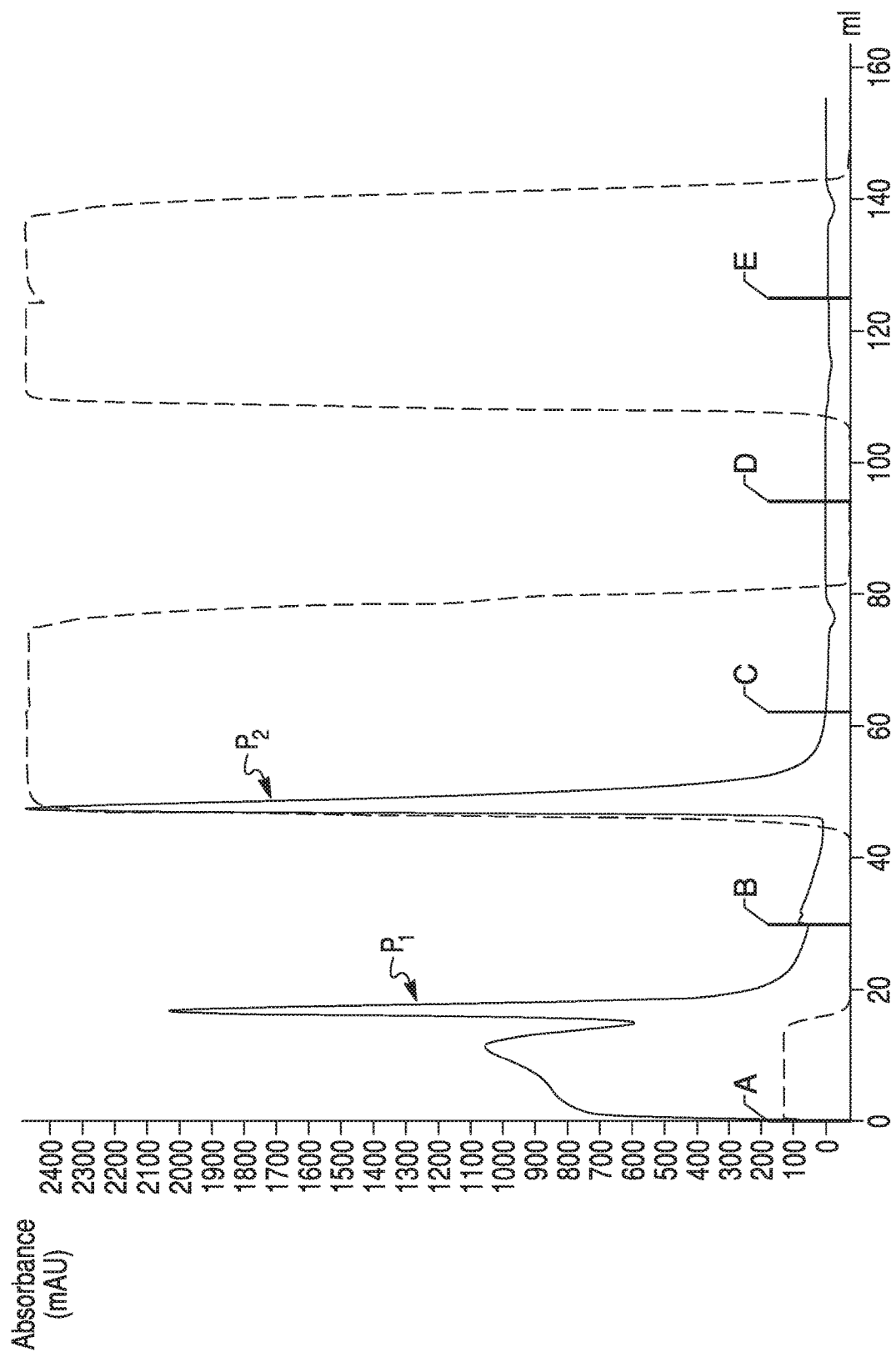
FIG. 9 depicts a chromatogram of a regeneration process using a guanidine HCl solution, according to aspects of the present disclosure.

As shown in the chromatogram of FIG. 9, the first introduction of RODI produced a peak $P_1$, and the first strip of 6N guanidine HCl subsequent to the first introduction of RODI produced a high peak, $P_2$. No peak is associated with second strip of 6N guanidine HCl, which was held in the column overnight before flow-through. This is possibly indicative of the efficacy of the first strip of 6N guanidine HCl in removing residue bound to the column. However, following the full cleaning protocol, the column remained discolored (as shown in FIG. 6).

Example 10

Figure 10A:
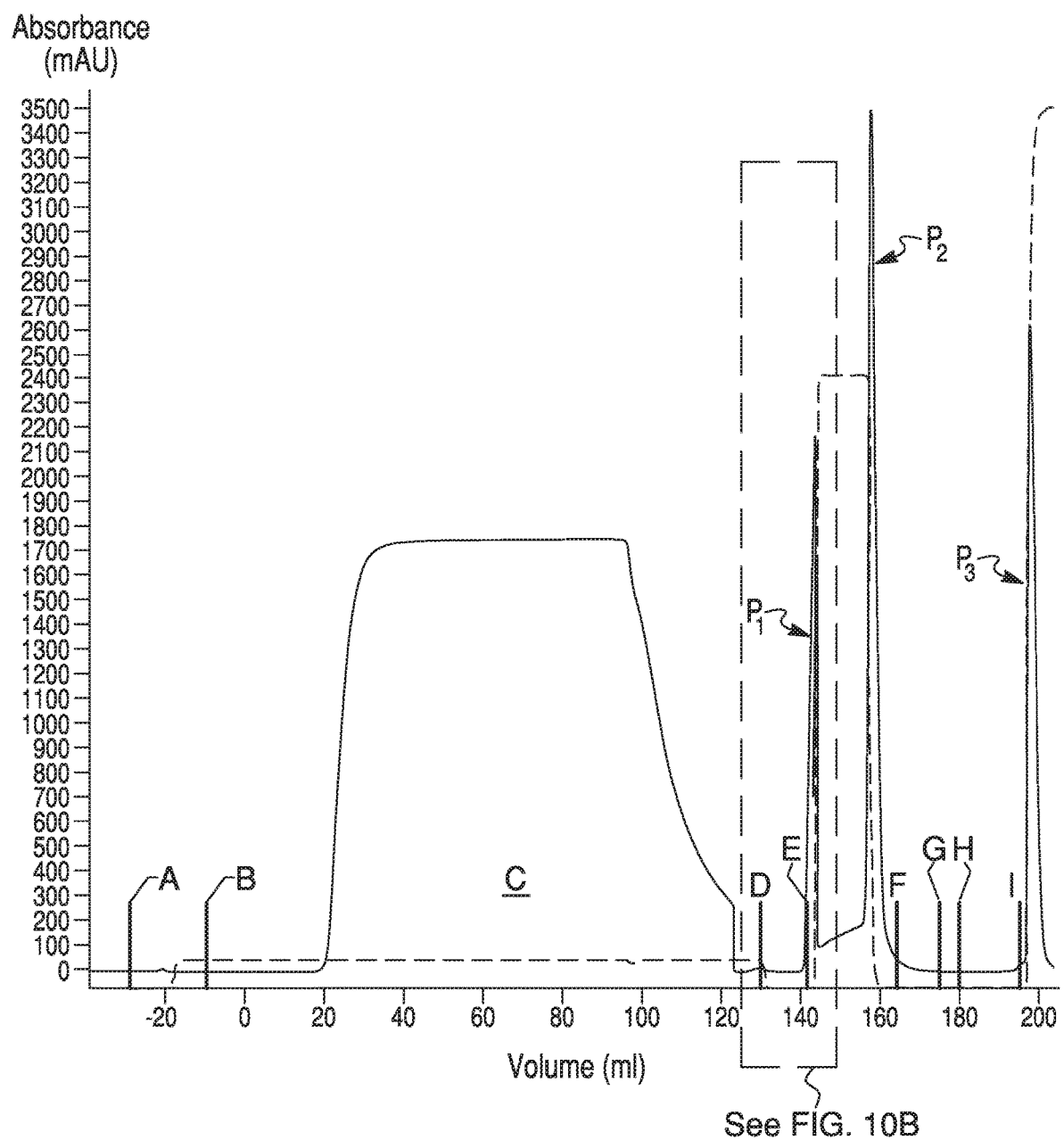
FIG. 10A depicts a chromatogram of a process including multiple regeneration solutions, according to aspects of the present disclosure.

A regeneration paradigm was analyzed in detail. FIG. 10A depicts a chromatogram of a HIC procedure during which a monoclonal antibody mAb 4 was purified using Capto™ Phenyl (High Sub) media (GE Life Sciences). The HIC procedure, including a regeneration paradigm, included the following steps:

TABLE 8

| Marker (FIG. 10A) | Event |
| --- | --- |
| A | Pre-Strip |
| B | Equilibration |
| C | Load and Wash |
| D | RODI Strip |
| E | 1N NaOH strip |
| F | RODI strip |
| G | 20% Ethanol strip |
| H | Pre-guanidine HCl Regeneration RODI |
| I | 6N guanidine HCl |

Referring to FIG. 10A, peak $P_1$ followed the introduction of 1N sodium hydroxide (E), and peak $P_2$ coincided with the second RODI strip (F). Peak $P_3$ followed the introduction of 6N guanidine HCL (I).

Figure 10B:
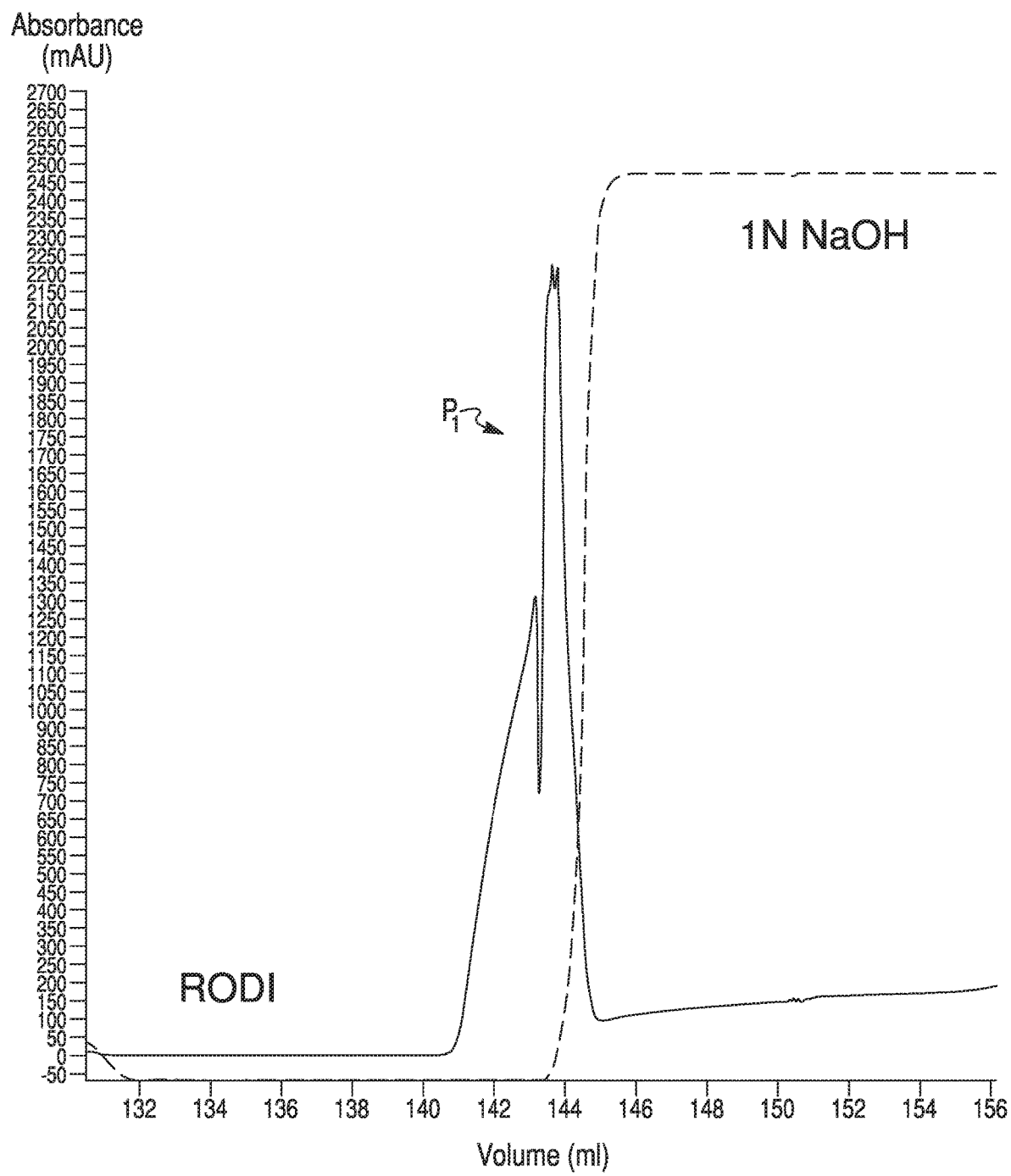
FIG. 10B depicts an enlarged image of a portion of the chromatogram in FIG. 10A.

FIG. 10B shows an enlarged image of peak $P_1$. The first RODI strip (D) did not result in detected absorbance. The 1N NaOH strip (E) appeared to result in immediate and early removal of residue from the column, as indicated by the presence of peak $P_1$, which appeared to baseline as conductivity increased. It is hypothesized that the initial RODI strip (D) may cause some residue to bind more tightly to the column, rather than promoting its removal. It is further hypothesized that elution of residue from the column caused by sodium hydroxide may primarily be driven by pH, but that as concentration of sodium (a weak kosmotrope) hydroxide increases, residual protein may be bound more tightly to the HIC media as conductivity of the solution increases.

Example 11

Figure 11:
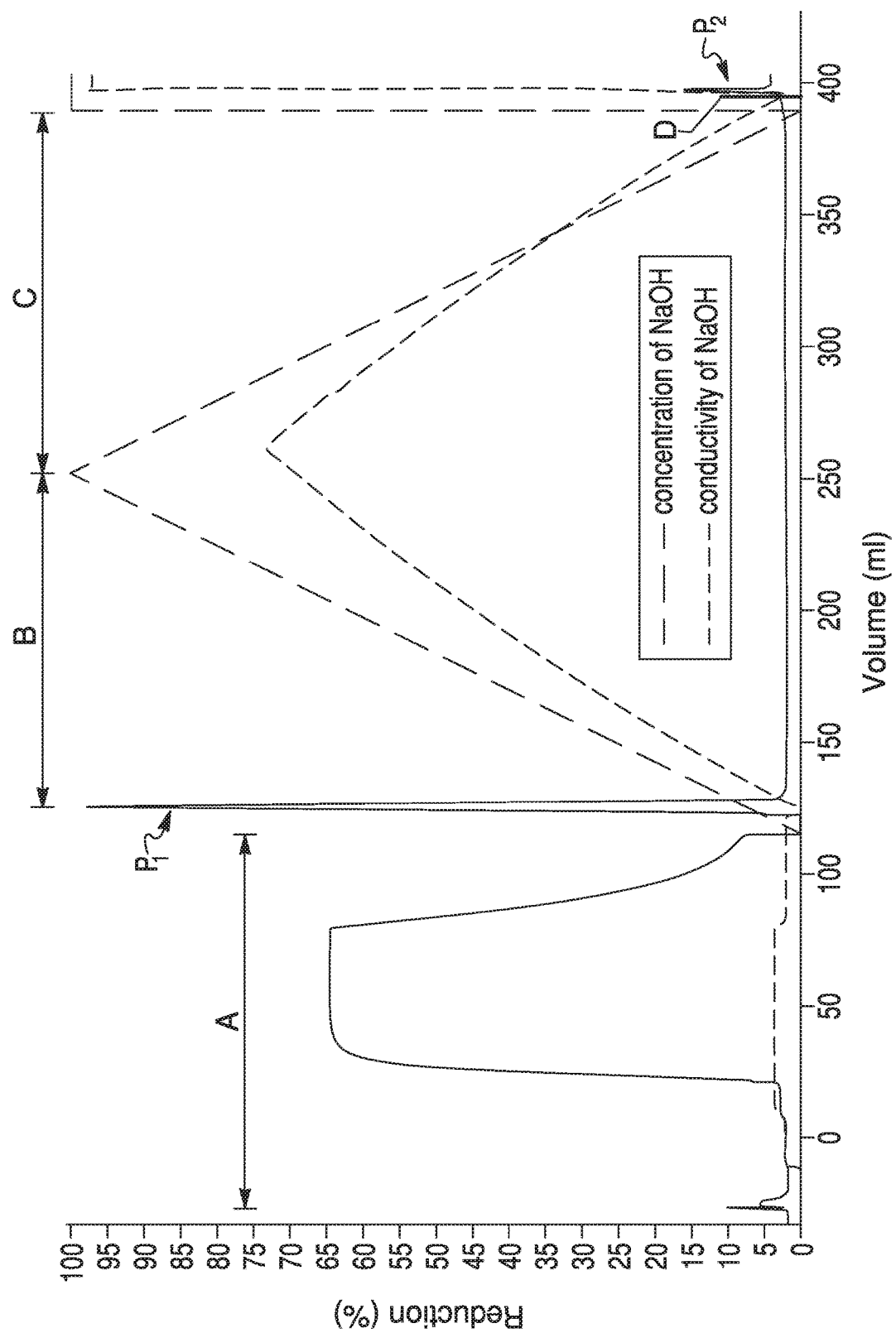
FIG. 11 depicts a chromatogram of a process in which sodium hydroxide solutions having a gradually increasing/gradually decreasing concentration have been introduced to a column, according to aspects of the present disclosure.

Elution of residue from used HIC media was observed as a function of sodium hydroxide concentration. FIG. 11 depicts a chromatogram of a process in which, following a load and wash of a HIC column to collect a monoclonal antibody mAb 4 (during section A), a 20 CV gradient was and loaded into the column, blending RODI and sodium hydroxide beginning with RODI alone and gradually increasing a concentration of sodium hydroxide to a maximum concentration of 1N sodium hydroxide (section B). A single definite peak $P_1$ was observed, eluting with passage of ~5 mM sodium hydroxide through the column. A second 20-CV gradient was performed and loaded into the column, beginning with RODI and sodium hydroxide at a maximum concentration of 1N, and gradually decreasing the concentration of sodium hydroxide to 0 (section C). No additional peaks were observed during this second gradient. Finally, a solution of 6N guanidine HCl was flushed through the column at mark D. A small peak $P_2$ was observed during passage of the 6N guanidine HCl through the column. Area under the curve (AUC) of each peak was calculated by integrated 280 nm UV absorbance. Peak $P_2$ was calculated to have an AUC of 1,160 mL*mAU, as compared to the AUC of a 6N guanidine HCl strip in a control procedure (e.g., Table 8), which was calculated to be 13,305 mL*mAU. Thus, peak $P_2$ exhibited a 91.3% reduction in size as compared to a control.

This process showed that a maximum of bound material eluted from the column when ~5 mM sodium hydroxide passed through the column, leaving relatively little residual media to elute with the 6N guanidine HCl.

Example 12

Figure 12:
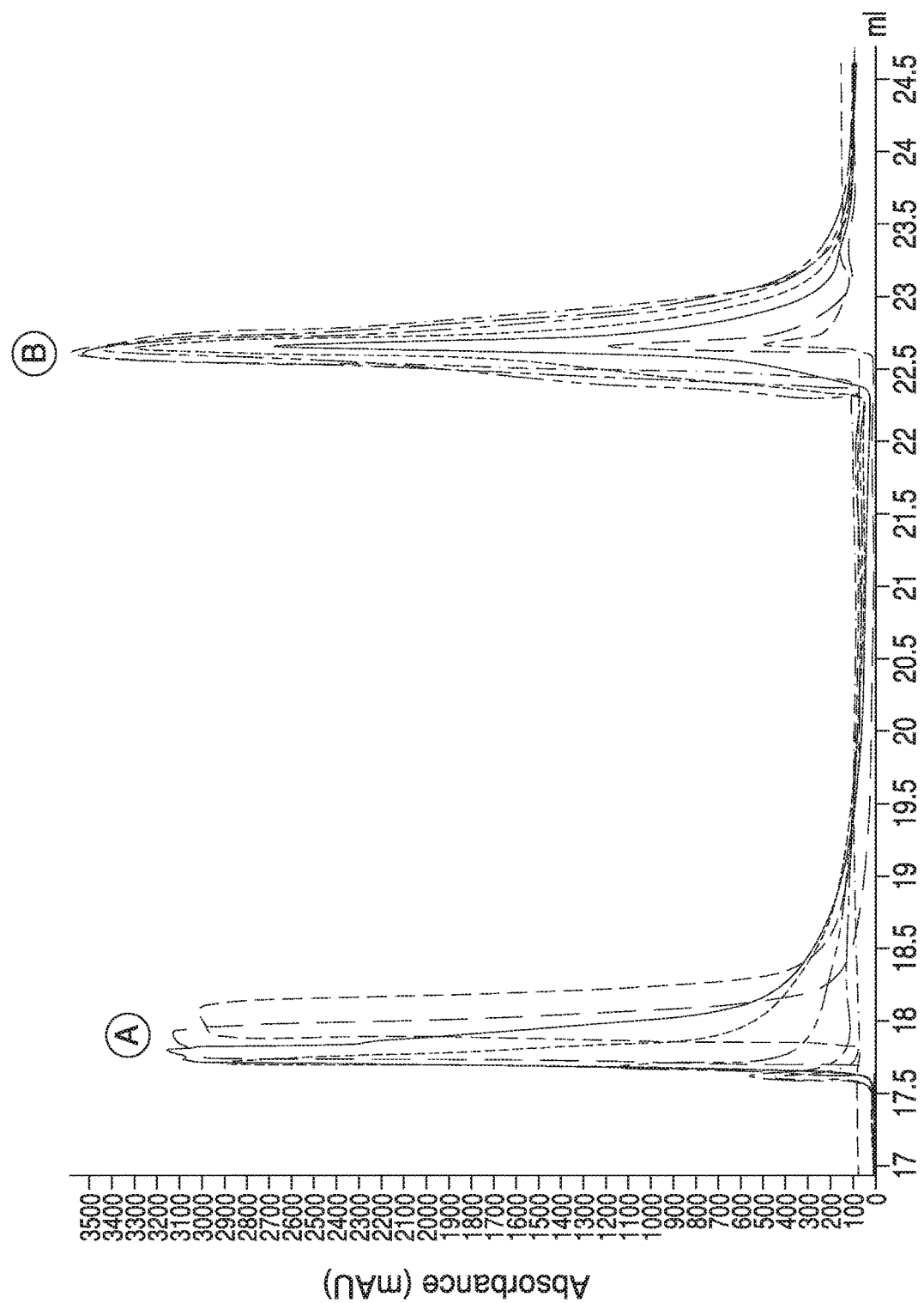
FIG. 12 depicts overlaid chromatograms of multiple two-solution column regeneration processes, according to aspects of the present disclosure.

Sodium hydroxide solutions having varying concentrations (1000 mM, 500 mM, 100 mM, 50 mM, 25 mM, 10 mM, and 5 mM) were applied in separate two-solution regeneration processes, each of which was performed following a load and wash of a HIC column. Each regeneration process included a sodium hydroxide solution as the first regeneration solution, and a 6N guanidine HCl solution as the second regeneration solution. Chromatograms for the regeneration processes were generated and are overlaid in FIG. 12. The sodium hydroxide solution in each regeneration process generated a first peak, represented by the group of peaks labeled A. The 6N guanidine HCl solution in each regeneration process generated a second peak, represented by the group of peaks labeled B. It was determined that the regeneration process including 5 mM NaOH generated the largest "A" peak (indicating the greatest amount of residue eluting with application of the sodium hydroxide solution) and the smallest "B" peak (indicating the least amount of residue eluting with application of guanidine HCl). It was thus determined that the 5 mM sodium hydroxide solution was the most effective at regenerating the HIC column (i.e., it removed the most bound material from the column), out of the range of sodium hydroxide solutions tested. The higher the sodium hydroxide concentration, the more residual mass was left on the column for removal by the 6N guanidine HCl solution. It was hypothesized that while increase in pH drove elution of residue from the HIC column, an increase in conductivity decreased elution of residue by strengthening bonds between residue and the HIC media.

Example 13

Figure 13A:
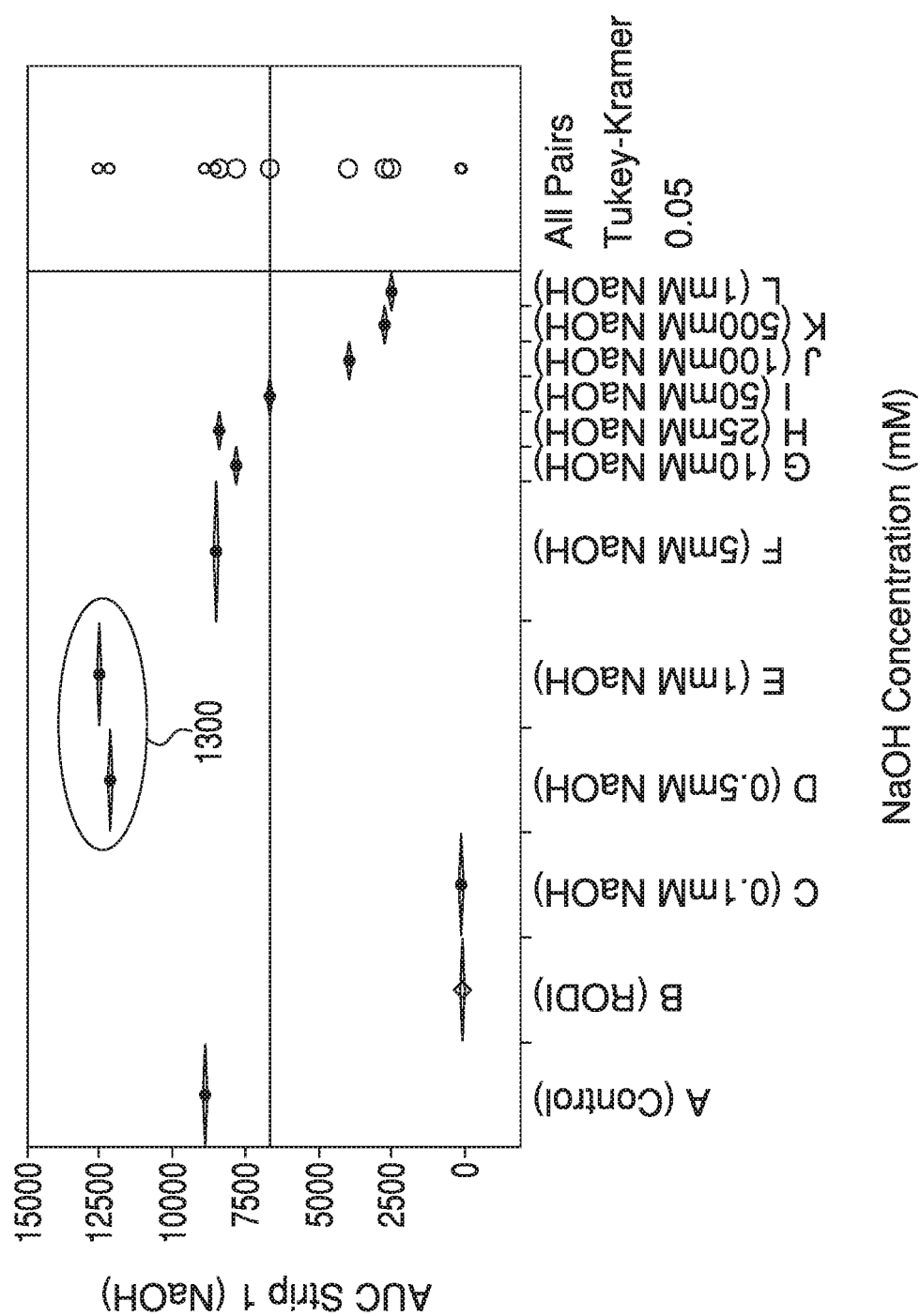
FIGS. 13A and 13B are visual depictions of statistical analyses of various peaks of chromatograms depicting regeneration processes, according to aspects of the present disclosure.
Figure 13B:
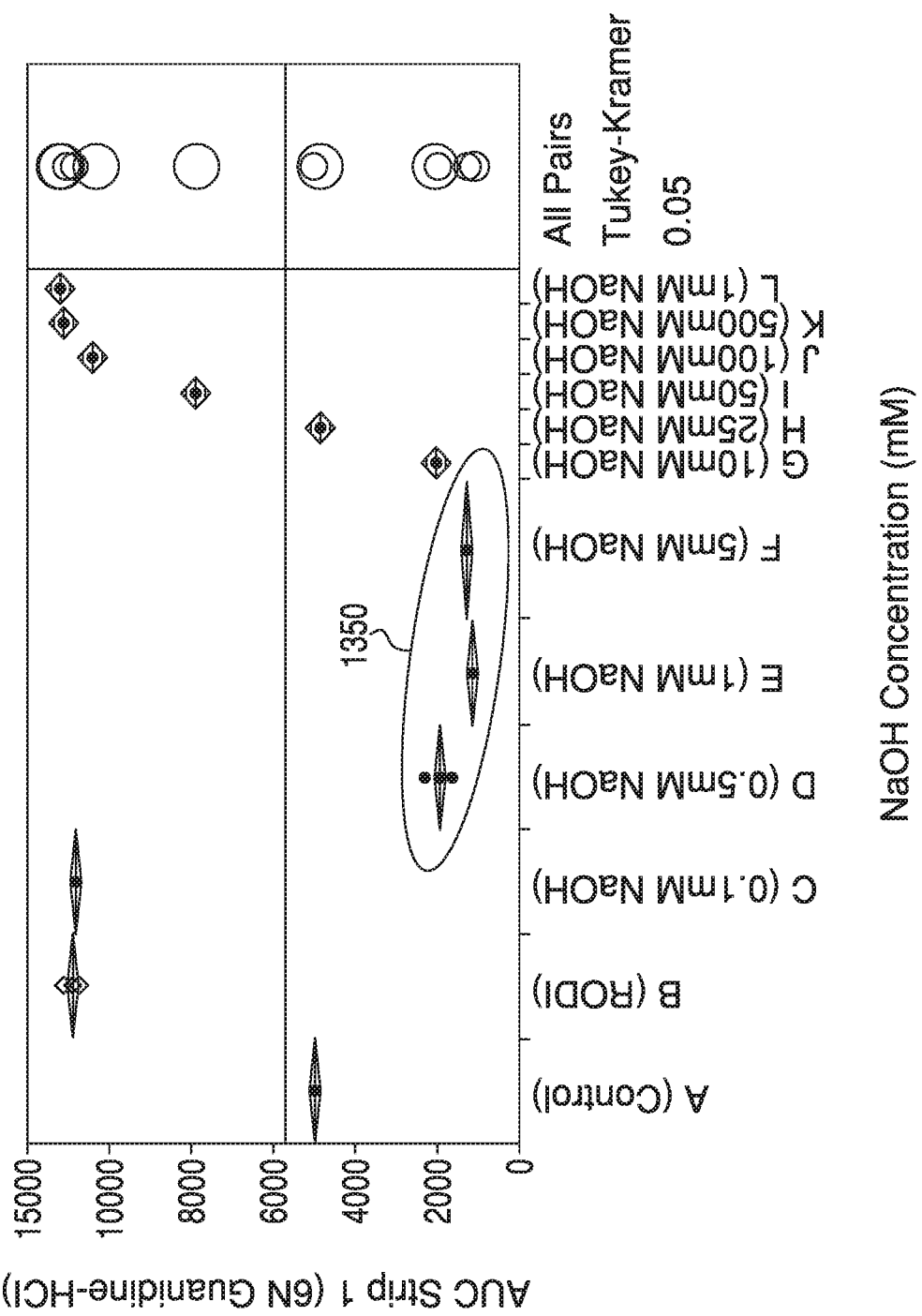

A one-way statistical analysis of variance was conducted on the area under the curve (AUC) of chromatogram peaks generated by regeneration procedures following collection of mAb 4 from HIC columns prepared with Capto™ Phenyl (High Sub) media (GE Healthcare Life Sciences). As shown in FIGS. 13A and 13B, regeneration procedures were performed using a control (A), RODI (B), and various concentrations of sodium hydroxide solutions (C-L). Each regeneration procedure included a stripping solution (AUCs analyzed in FIG. 13A) followed by a solution of 6N guanidine HCl (AUCs analyzed in FIG. 13B). An All Pairs Turkey-Kramer test was also performed on each analysis to depict statistical significance.

As shown in FIGS. 13A and 13B, the procedures associated with 0.5 mM NaOH and 1 mM NaOH regeneration solutions showed the highest AUC values (circled in area 1300) for peaks generated during flow-through of those regeneration solutions, indicating that these regeneration solutions caused a more effective removal of material from the HIC columns. The procedures associated with 0.5 mM NaOH, 1 mM NaOH, and 5 mM NaOH regeneration solutions showed the lowest AUC values (circled in area 1350 of FIG. 13B) for peaks generated during flow-through of the 6N guanidine HCl solution subsequent to the regeneration solutions, also supporting that these regeneration solutions caused a more effective removal of material from the HIC columns, leaving less to be removed by the 6N guanidine HCl. Accordingly, solutions having sodium hydroxide concentrations ranging from 0.5 mM to 5 mM NaOH were shown to be effective for regeneration of HIC columns.

Example 14

Regeneration processes using sodium hydroxide solutions were compared to regeneration processes using sodium chloride solutions. Following collection of a monoclonal antibody mAb 5 from HIC columns, the columns were regenerated using sodium hydroxide having a concentration of 3 mM, 5 mM, or 7 mM, or using sodium chloride having a concentration of 5 mM, 8 mM, or 11 mM. The pH and conductivity of each regeneration solution were also noted. The sodium hydroxide solutions all exhibited a pH of greater than 11, while the sodium chloride solutions all exhibited a pH of between 5.5 and 6.5. Conductivities of the solutions were comparable. For each process, a solution of 6N guanidine HCl was applied to each column after the regeneration solution. A chromatogram was generated for each process, all of which are overlaid in FIG. 14. AUC was calculated for peaks associated with flow-through of the regeneration solution and flow-through of the 6N guanidine HCl. The solutions and AUC are listed in the table below.

TABLE 9

| Regeneration Solution | pH | Conductivity | Regeneration Solution AUC (mL * mAU) | 6N guanidine HCl AUC (mL * mAU) |
| --- | --- | --- | --- | --- |
| 3 mM NaOH | 11.49 | 0.74 | 29,671 | 501 |
| 5 mM NaOH | 11.70 | 1.20 | 27,344 | 562 |
| 7 mM NaOH | 11.83 | 1.68 | 27,497 | 958 |
| 5 mM NaCl | 6.07 | 0.72 | 255 | 34,524 |
| 8 mM NaCl | 5.96 | 1.18 | 146 | 34,114 |
| 11 mM NaCl | 6.04 | 1.65 | 226 | 32,852 |

Figure 14:
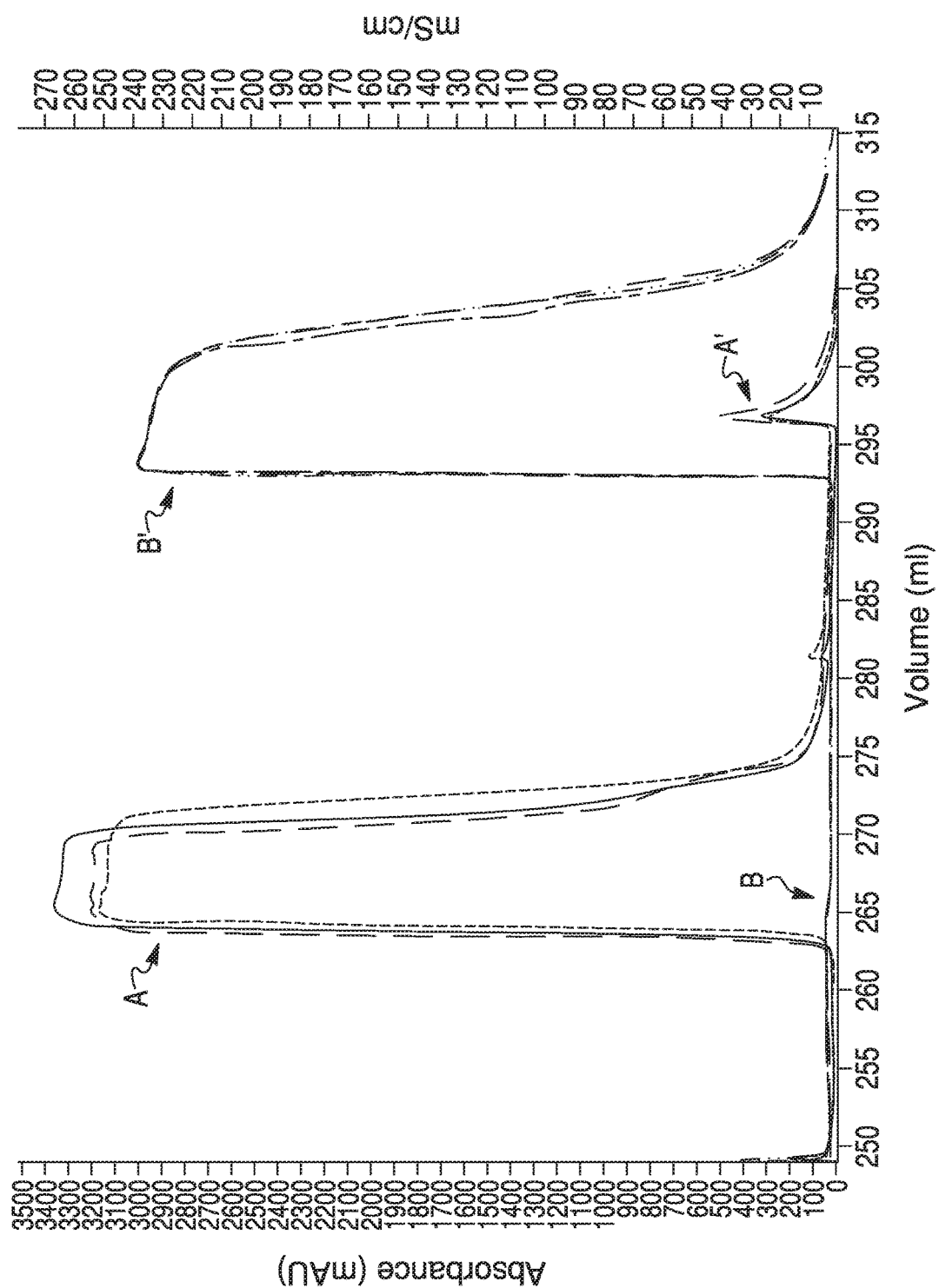
FIG. 14 depicts overlaid chromatograms of multiple two-solution column regeneration processes including either sodium hydroxide or sodium chloride and guanidine HCl, according to aspects of the present disclosure.

As depicted by this data, the flow-through of the sodium hydroxide solutions exhibited substantially higher AUC values than the sodium chloride solutions. Likewise, the flow-through of 6N guanidine HCl following the sodium hydroxide solutions exhibited substantially lower AUC values than the flow-through of 6N guanidine HCl following the sodium chloride solutions. In FIG. 14, peaks generated by flow-through of sodium hydroxide are indicated by marker A, and peaks (or lack thereof) generated by flow-through of sodium chloride are indicated by marker B. Likewise, peaks generated by flow-through of 6N guanidine HCl following sodium hydroxide and peaks generated by flow-through of 6N guanidine HCl following sodium chloride are indicated by markers A' and B', respectively. As is shown in FIG. 14, the sodium hydroxide solutions were more effective stripping agents than the sodium chloride solutions.

Example 15

Figure 15:
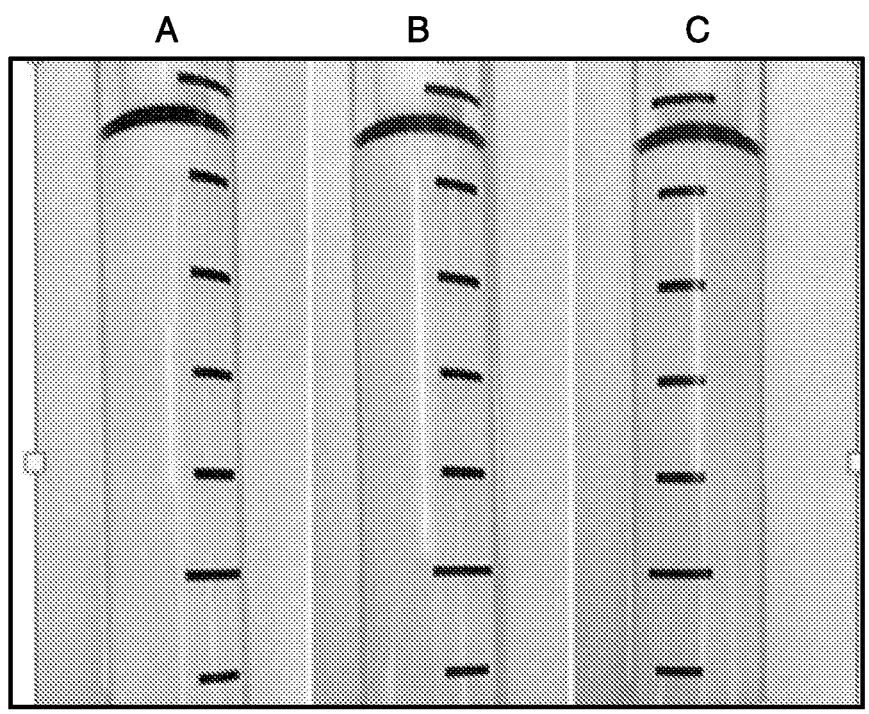
FIG. 15 depicts three chromatographic columns to which solutions have been applied, according to aspects of the present disclosure.

Potential cleaning/regeneration solutions were tested on columns that had been subjected to 50 cycles of HIC to purify a monoclonal antibody mAb 6. The columns exhibited discoloration near the top of the column bed, as depicted in FIG. 15 (columns A, B, and C). Column A was flushed with 2 CV's of 0.5 M EDTA, column B was flushed with 2 CV's of 0.5 M Acetic Acid, and column C served as a control. Neither solutions were effective in reducing the browning/discoloration.

Example 16

Figure 16:
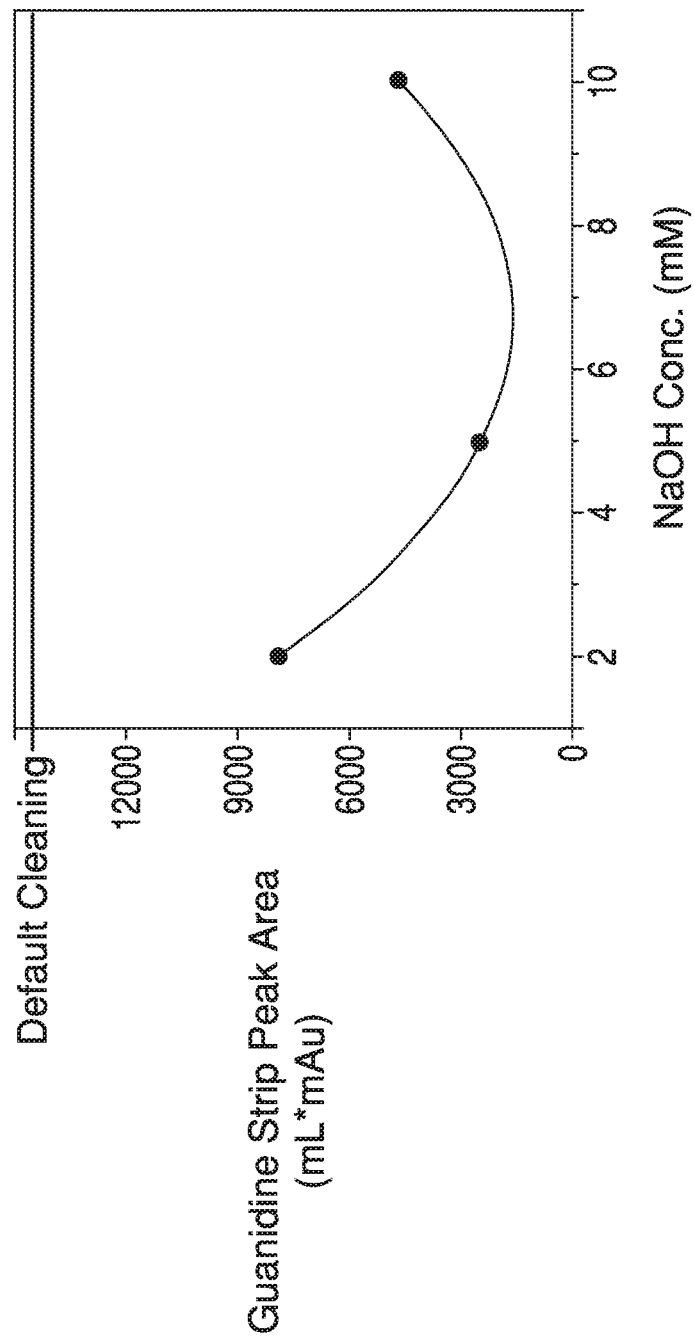
FIG. 16 depicts a graph of guanidine HCl stripping solution peak areas as a function of sodium hydroxide concentration, according to aspects of the present disclosure.

Three sodium hydroxide solutions (2 mM, 5 mM, and 10 mM) were used as regeneration solutions following HIC purification of monoclonal antibody mAb 6. The efficacy of each sodium hydroxide solution in regenerating HIC media used in the purification process was characterized by the size of a chromatogram peak associated with a 6N guanidine HCl strip following application of each sodium hydroxide solution. A larger AUC associated with the guanidine strip peak indicated a greater quantity of residue left by the sodium hydroxide solution preceding the strip, and conversely, a smaller AUC associated with the guanidine strip peak indicated a lesser amount of residue left by the sodium hydroxide solution preceding the strip, and consequently, a more effective sodium hydroxide regeneration solution. FIG. 16 depicts a graph showing guanidine strip peak AUC as a function of sodium hydroxide concentration. All three tested sodium hydroxide solutions showed more effective regeneration (i.e., a smaller guanidine strip peak) than a default cleaning paradigm including a sequence of RODI, 1N sodium hydroxide, RODI, 20% ethanol, and RODI. The 5 mM sodium hydroxide solution had the lowest guanidine strip peak area. Based on a curve extrapolated from the data points, it is possible that a 7 mM sodium hydroxide regeneration solution might result in an even lower guanidine strip peak area.

Example 17

Figure 17:
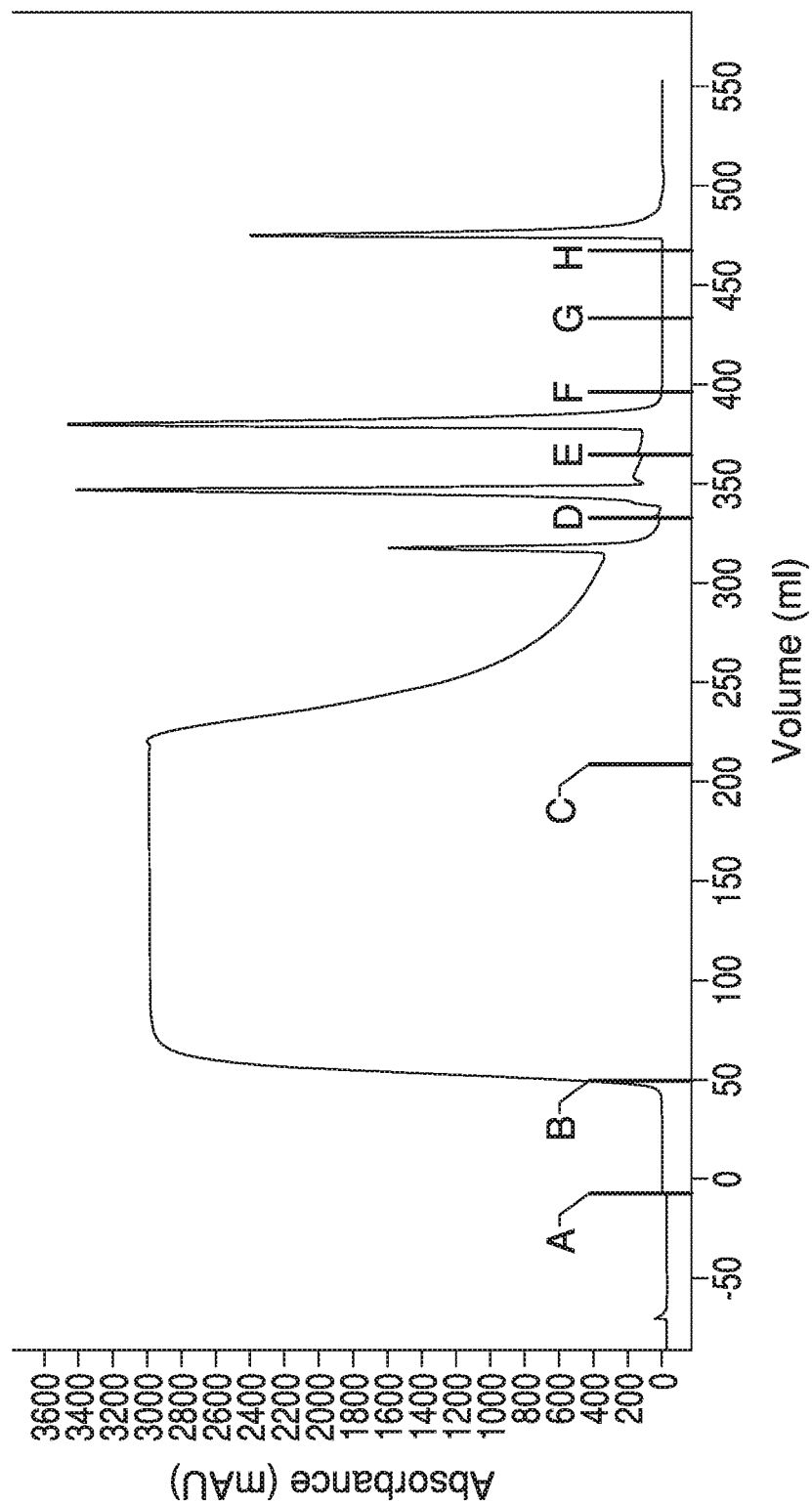
FIGS. 17 and 18 depict chromatograms of a control regeneration process and an experimental regeneration process, each including multiple regeneration solutions, according to aspects of the present disclosure.

A first regeneration process, designed as a control, was used on a HIC column following collection of monoclonal antibody mAb 5 from the column. A chromatogram was generated using the process. Multiple solutions were used in sequence, beginning with 1N sodium hydroxide, followed by RODI, 20% ethanol, RODI, and 6N guanidine HCl. The chromatogram peak corresponding to the flow-through of the 6N guanidine HCl was used as a measurement of the effectiveness of the regeneration process. The chromatogram is depicted in FIG. 17. The markers on the chromatogram indicate the following events:

TABLE 10

| Marker | Event |
| --- | --- |
| A | Load |
| B | Pool collection begun |
| C | Wash |
| D | 1N NaOH solution introduced |
| E | RODI introduced |
| F | 20% Ethanol introduced |
| G | RODI introduced |
| H | 6N guanidine HCl introduced |

The AUC of the peak corresponding to flow-through of the 6N guanidine HCl solution was calculated to be 7,390 mL*mAU.

Figure 18:
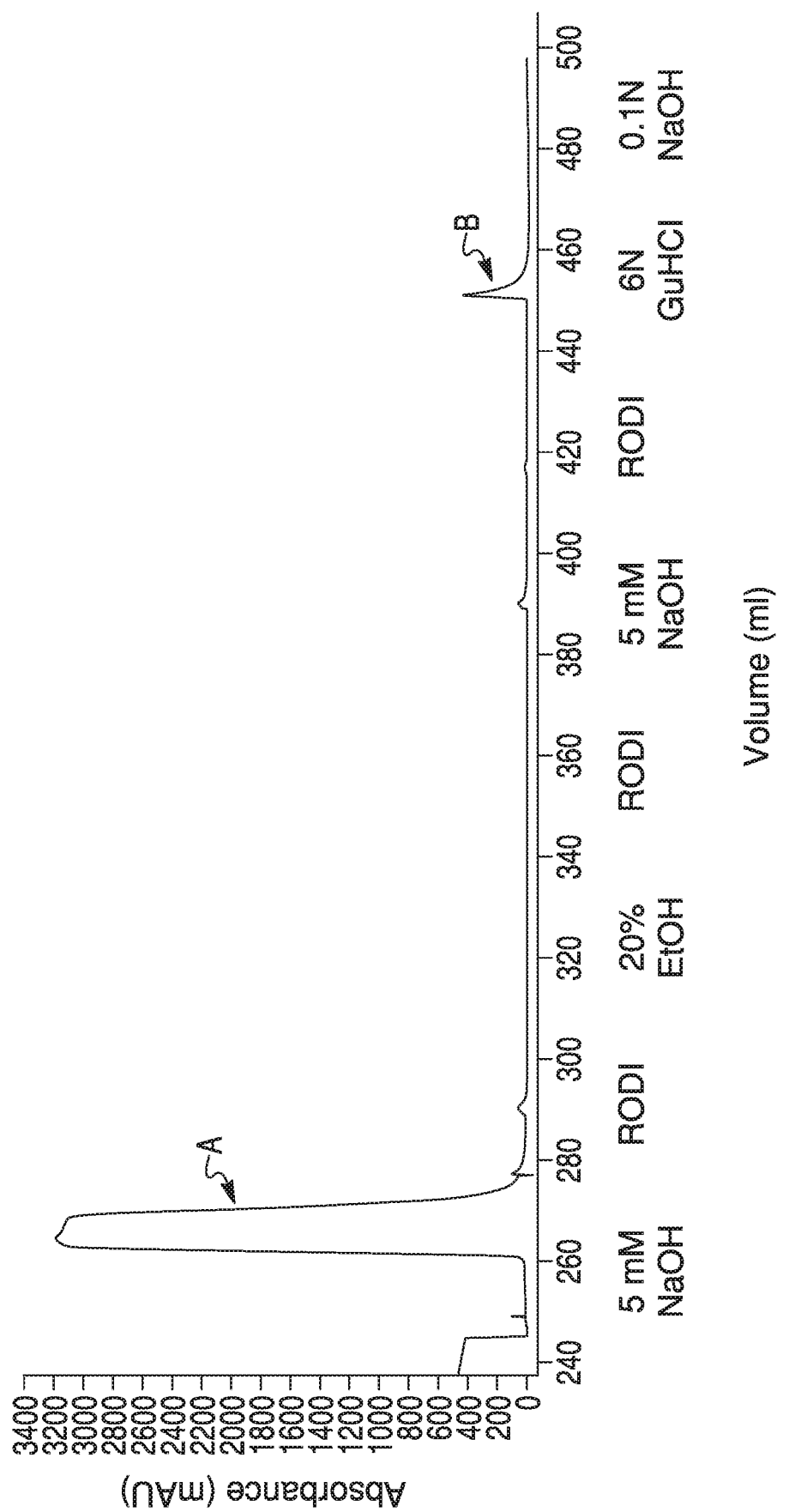

A second regeneration process including 5 mM sodium hydroxide was used following collection of mAb 5 from a HIC column, and a chromatogram was generated, depicted in FIG. 18. Multiple solutions were used in sequence, beginning with 5 mM sodium hydroxide, followed by RODI, 20% ethanol, RODI, 5 mM sodium hydroxide, RODI, 6N guanidine HCl, and 0.1N sodium hydroxide. An AUC corresponding to the flow-through of each solution was calculated from the chromatogram, the results of which are listed in the following table:

TABLE 11

| Order | Solution | AUC (mL * mAU) |
|---|---|---|
| 1 | 5 mM NaOH | 29,119 |
| 2 | RODI | 196 |
| 3 | 20% EtOH | 4 |
| 4 | RODI | 1 |
| 5 | 5 mM NaOH | 125 |
| 6 | RODI | 57 |
| 7 | 6N guanidine HCl | 889 |
| 8 | 0.1N NaOH | N/A |

As shown in FIG. 18 and reflected by the AUC values in the table above, the initial 5 mM NaOH flow-through showed the greatest AUC by a large margin (peak A). Solutions applied to the column after the initial 5 mM NaOH solution provided minimal additional removal of material from the HIC column, as demonstrated by their relatively small corresponding AUC values. The second-greatest AUC value was associated with the flow-through of 6N guanidine HCl, but at 889 mL*mAU was less than one-thirtieth of the value of the AUC associated with the initial 5 mM NaOH flow-through. Moreover, the smaller AUC value of the 6N guanidine HCl peak in this regeneration process as compared to the AUC value of the 6N guanidine HCl peak in the control process depicted in FIG. 17 (7,390 mL*mAU) indicated that the initial 5 mM NaOH solution provided substantially improved regeneration of the HIC column, as compared to the control run. RODI, 20% ethanol, 6N guanidine HCl, and 0.1N NaOH provided minimal additional benefit to HIC regeneration when used after a 5 mM NaOH solution.

Example 18

Six mixtures, each including a different target molecule (e.g., target monoclonal antibody) and including a different concentration of citrate in the load buffer, were subjected to HIC in a column containing Capto™ Phenyl (High Sub) media (GE Life Sciences). Following elution of each monoclonal antibody, the used HIC column was subjected to a volume of RODI and sodium hydroxide in a gradient beginning from no sodium hydroxide (pure RODI) to 1N sodium hydroxide, followed by a gradient in the opposite direction (from 1N sodium hydroxide back to pure RODI). Finally, each process ended with loading and collecting flow-through for 6N guanidine HCl. The table below indicates the pH and concentration of citrate in each load mixture.

TABLE 12

| Mixture | Target antibody | pH | Citrate concentration in load buffer |
|---|---|---|---|
| A | mAb 7 | 5.3 | 30 mM |
| B | mAb 8 | 6 | 10 mM |
| C | mAb 1 | 6.5 | 40 mM |
| D | mAb 2 | 5.8 | 30 mM |
| E | mAb 6 | 6 | 30 mM |
| F | mAb 9 | 8 | 140 mM |

Figure 19:
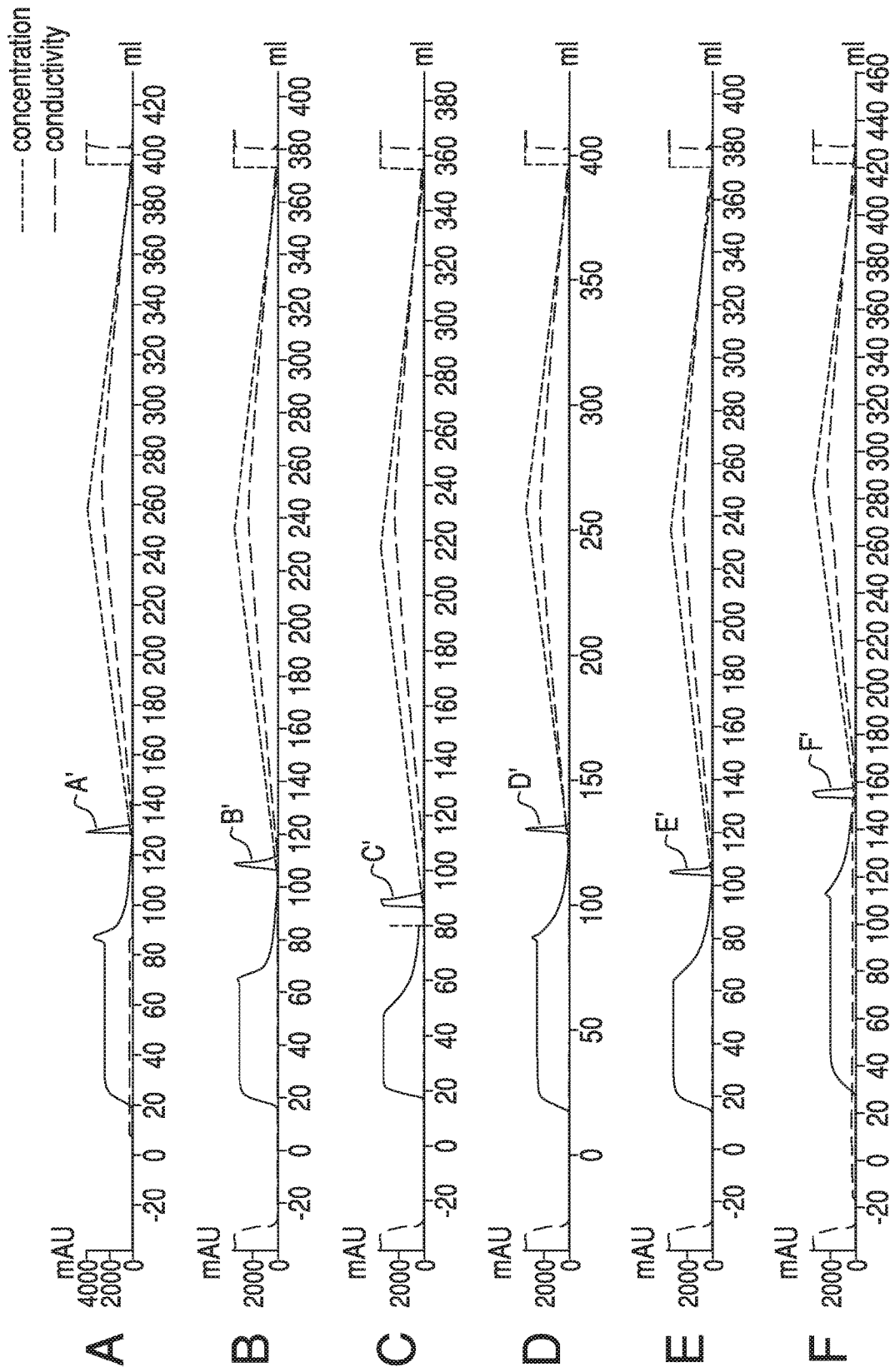
FIG. 19 depicts a series of chromatograms of hydrophobic interaction chromatography runs to purify different monoclonal antibodies, according to aspects of the present disclosure.

A chromatogram was produced for each process; the chromatograms are depicted in series in FIG. 19. As shown, each chromatogram A-F includes a peak (A', B', C', D' E', F') corresponding to elution of material bound to the HIC media at the flow-through of about 5 mM NaOH. Subsequent guanidine HCl flow-through peaks were extremely small or nonexistent. It was thus shown that effectiveness of the regeneration solution was not confined to the use of one monoclonal antibody.

Example 19

Multiple HIC protocols having different conditions were evaluated to determine whether such protocols may pose regeneration/usability challenges. Wells of a 96-well filter plate (AcroPrep™ Advance 1 mL Filter Plate, 1.2 μm Supor membrane, part #8130, Pall Corporation) were packed with 0.02 μL of various HIC media as follows:

TABLE 13

| Wells in Columns: | Media |
|---|---|
| 1-3 | TOYOPEARL ® Hexyl-650C |
| 4-6 | Media B (Phenyl Sepharose 6 Fast Flow (High Sub) (GE Healthcare Life Sciences)) |
| 7-9 | Media C (POROS ™ Ethyl (Thermo Scientific ™)) |

Aliquots of load material containing one of three target antibodies (mAb 1, mAb 2, mAb 3) were prepared and adjusted to a concentration of 0.33 g/L, to target a concentration of 5 g/L when mixed with the HIC media. For each of the three target antibodies, an aliquot of load material was titrated to a different pH (4.5, 6.25, or 8.0) using 2 M acetic acid or 2 M Tris base, to prepare a total of nine aliquots, each including one of the three target antibodies and exhibiting one of the three different pH values.

Each of the three columns of wells packed with a single media type was subjected to a purification protocol at a different pH (4.5, 6.25, or 8.0), to create an array of protocols performed using various combinations of media and pH. Rows of wells in each column were divided into groups, such that each group of rows was subjected to a protocol for a different target antibody (mAb 1, mAb 2, or mAb 3). To run each protocol at a respective pH, for a respective target antibody, an aliquot of load material including the target antibody at the corresponding pH was used, as well as an equilibration buffer of 40 mM Tris, 300 mM citrate at the corresponding pH.

The following steps are performed simultaneously on the array:
1. The wells packed with various HIC resins are equilibrated three times using the equilibration buffer at the respective pH.
2. Load material including the desired target antibody at the respective pH is added to each well and incubated for one hour.
3. The plates is spun at 1100 rpm.

4. Flowthrough (such as components not bound to the media during incubation) is collected.
5. The wells are washed twice using the equilibration buffer at the respective pH for each protocol being tested.
6. A pseudo-gradient elution is performed using the equilibration buffer at the respective pH. Each well is exposed to the equilibration buffer for seven iterations, where citrate concentration is decreased linearly from 300 mM to 0 mM across all seven iterations (in increments of 42.9 mM per iteration).
7. The wells are washed twice with RODI and twice with 1N sodium hydroxide.
8. The plate is spun at 1100 rpm.
9. The wells are stripped twice with a solution of 6N guanidine HCl.
10. The plate is spun at 1100 rpm.

Figure 20A:
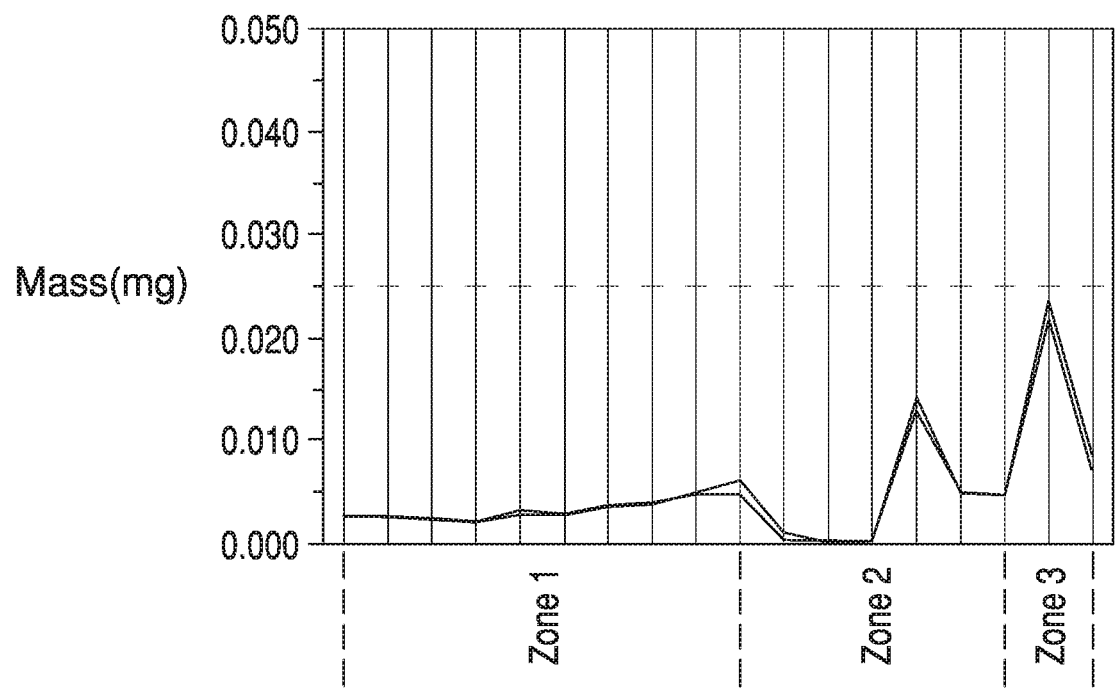
FIGS. 20A-20C depict chromatograms generated using protocols including three different hydrophobic interaction chromatography media, according to aspects of the present disclosure.
Figure 20B:
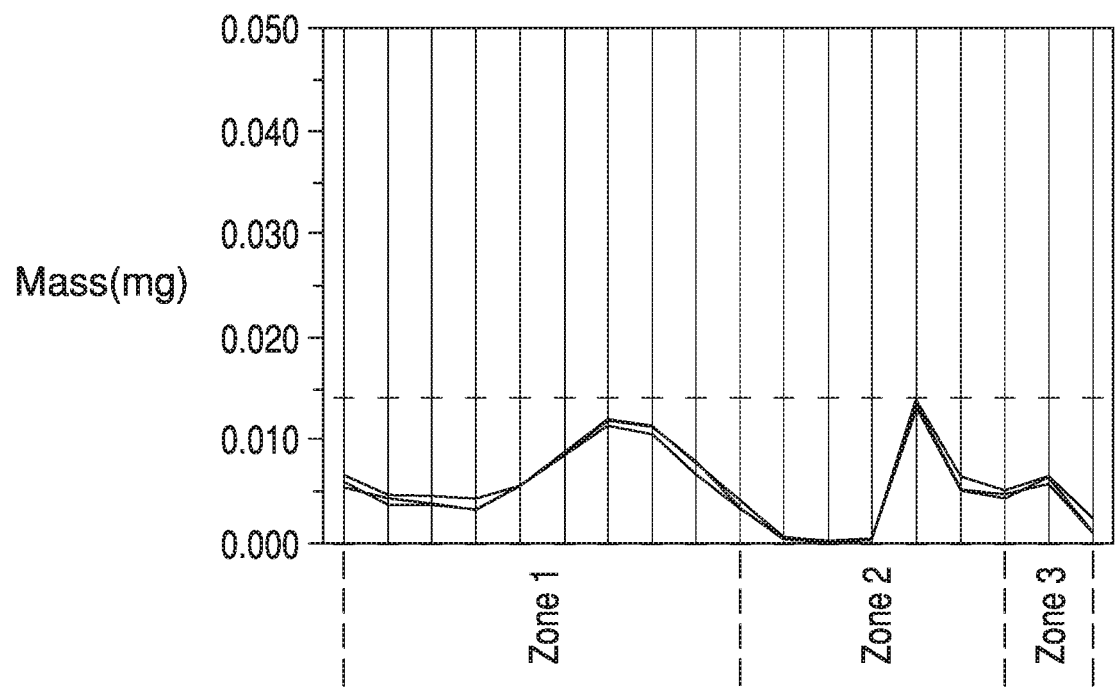
Figure 20C:
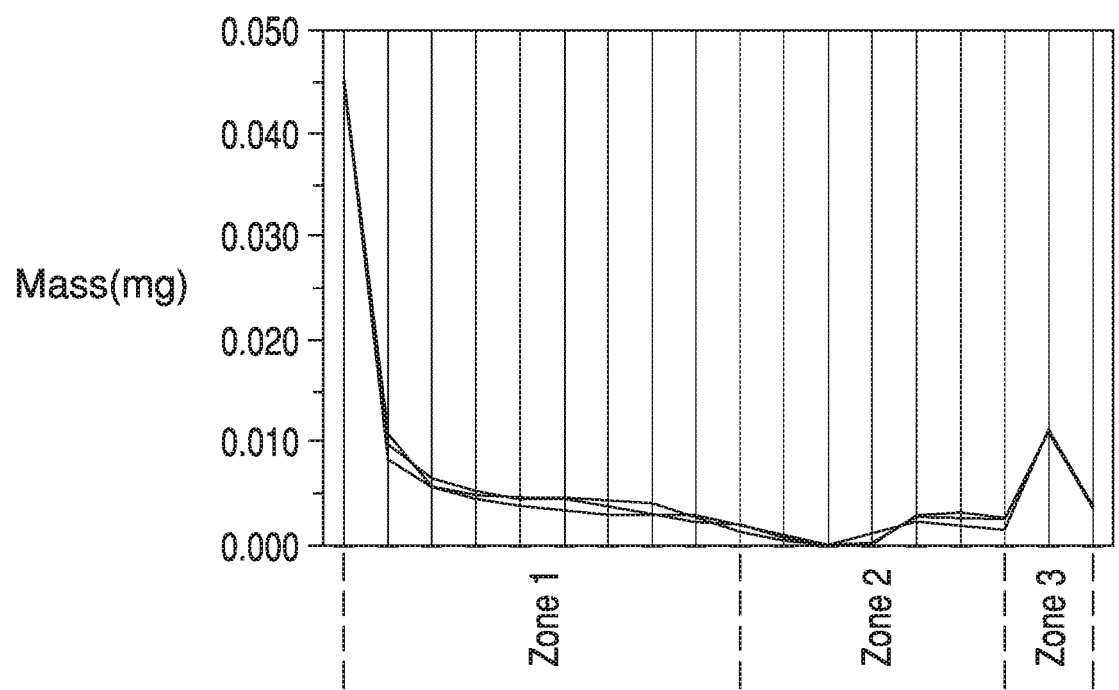

For each well, a chromatogram of the target polypeptide in the material removed from the well (flowthrough, eluent, wash, etc.) was generated. To analyze results, each chromatogram was divided into three zones, where a first zone included the mass of target polypeptide observed in material removed during steps 2, 3, and 4 (flowthrough, washes, and elution), a second zone included the mass of target polypeptide observed in material removed during step 5, 6, 7, 8 (using RODI and 1N sodium hydroxide), and a third zone included the mass of target polypeptide observed in material removed during step 9, 10 (using 6N guanidine HCl). Examples of three chromatograms generated from protocols purifying a target antibody mAb 1, at a pH of 6.25, and each of the three different HIC media (TOYOPEARL® Hexyl-650C, Phenyl Sepharose 6 Fast Flow (High Sub), and POROS™ Ethyl) and divided into three zones are depicted in FIGS. 20A-20C.

Comparison indicate that the protocols and analyses performed on the test wells aligned with the protocols and analyses performed on the large scale columns with a statistically-significant accuracy of 98%.

Example 20

Aggregate collection of data using the high-throughput screening techniques described herein, enables the development of predictive functions, that may inform development of HIC protocols with improved efficiencies and yields. For example, boundary functions may be plotted which describe relationships between multiple parameters (e.g., pH, elution buffer citrate concentration, loading mass, HIC media selection) and either an efficiency or yield of the protocol.

Figure 21A:
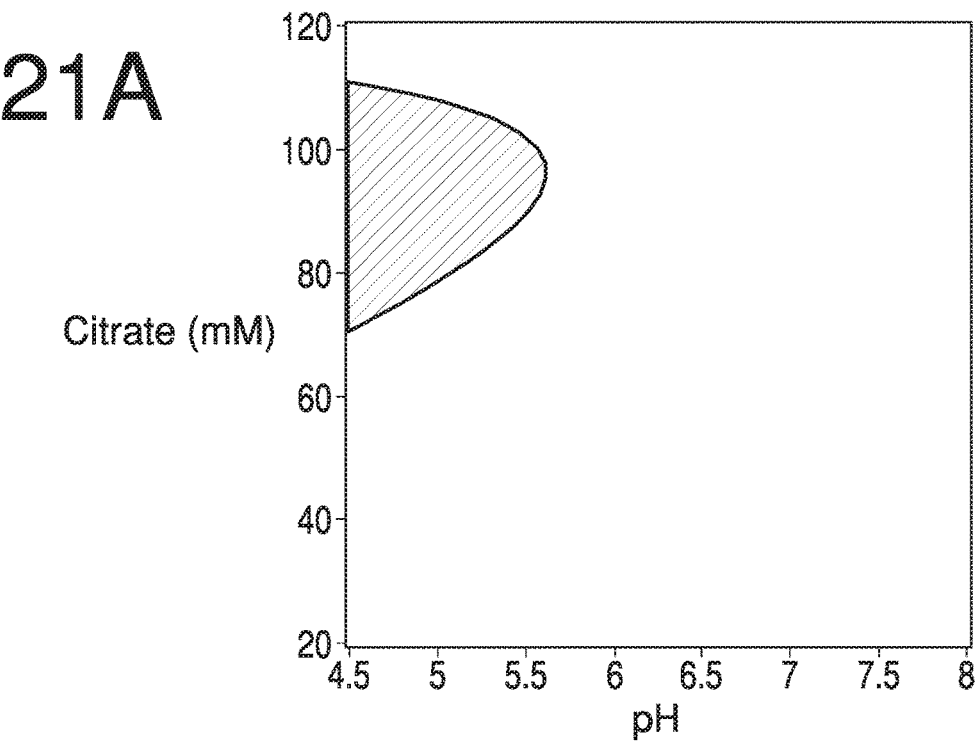
FIGS. 21A and 21B depict plots of boundary functions developed through analysis of data generated during high-throughput screening and full-scale chromatography runs, according to aspects of the present disclosure.

FIG. 21A is a plot of a boundary function relating elution buffer citrate concentration and pH to the predicted yield of the HIC protocol, based on aggregate collection of high-throughput screening data for a given antibody and Phenyl Sepharose® media, at a load of 100 g per liter of media. The shaded area represents combinations of HIC protocol parameters that result in a predicted yield of less than 90% of the theoretical yield. This boundary function informs what citrate and pH parameters should be considered for HIC protocols including the given antibody and Phenyl Sepharose® media. Combinations of pH and citrate concentration outside of the shaded area are viable HIC protocol parameters for the given antibody and the Phenyl Sepharose® media, while combinations of pH and citrate concentrations within the shaded area are excluded parameters.

Figure 21B:
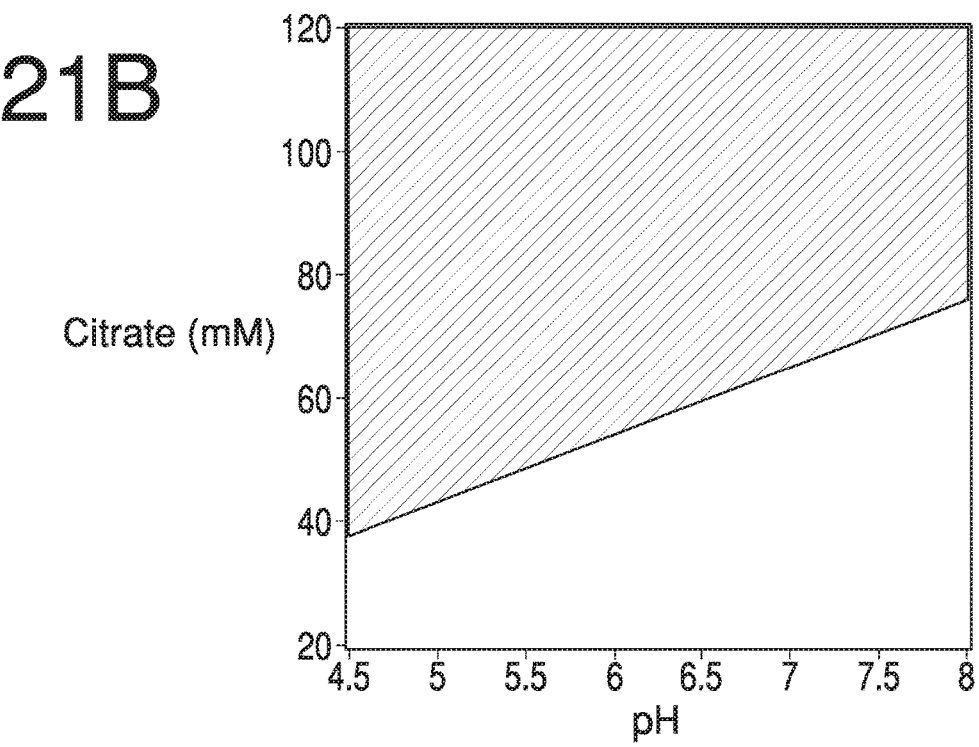

FIG. 21B is a plot of a boundary function relating elution buffer citrate concentration and pH to the predicted yield of the HIC protocol, based on aggregate collection of high-throughput screening data for the given antibody and Capto™ Phenyl (High Sub) chromatography media, at a load of 100 g per liter of media. The shaded area represents combinations of HIC protocol parameters that result in a predicted yield of less than 90% of the theoretical yield. This boundary function informs what citrate and pH parameters should be considered for HIC protocols including the given antibody and Capto™ Phenyl (High Sub) media. Combinations of pH and citrate concentration outside of the shaded area are viable HIC protocol parameters for the given antibody and the Capto™ Phenyl (High Sub) media, while combinations of pH and citrate concentrations within the shaded area are excluded parameters.

In addition to the boundary functions described above, the data collected from high-throughput screening may enable the development of a transfer function, or other mathematical model, that may aid in the design of HIC protocols. For example, a transfer function may be regressed that relates data from an elution assay, high-throughput screen, or bench-scale HIC protocol, to a full-scale HIC protocol. For example, for a set of HIC protocols including a predicted yield (e.g., a yield predicted by small scale assay or high-throughput screening), an actual yield may be determined for each HIC protocol via full-scale chromatography. A relationship between predicted yield and actual yield may be regressed to improve the predictive models. Future predicted yields may be calculated, at least in part, based on the regressed relationship (e.g., transfer function) as applied to data from an elution assay, high-throughput screen, or bench-scale HIC protocol.

Figure 22:
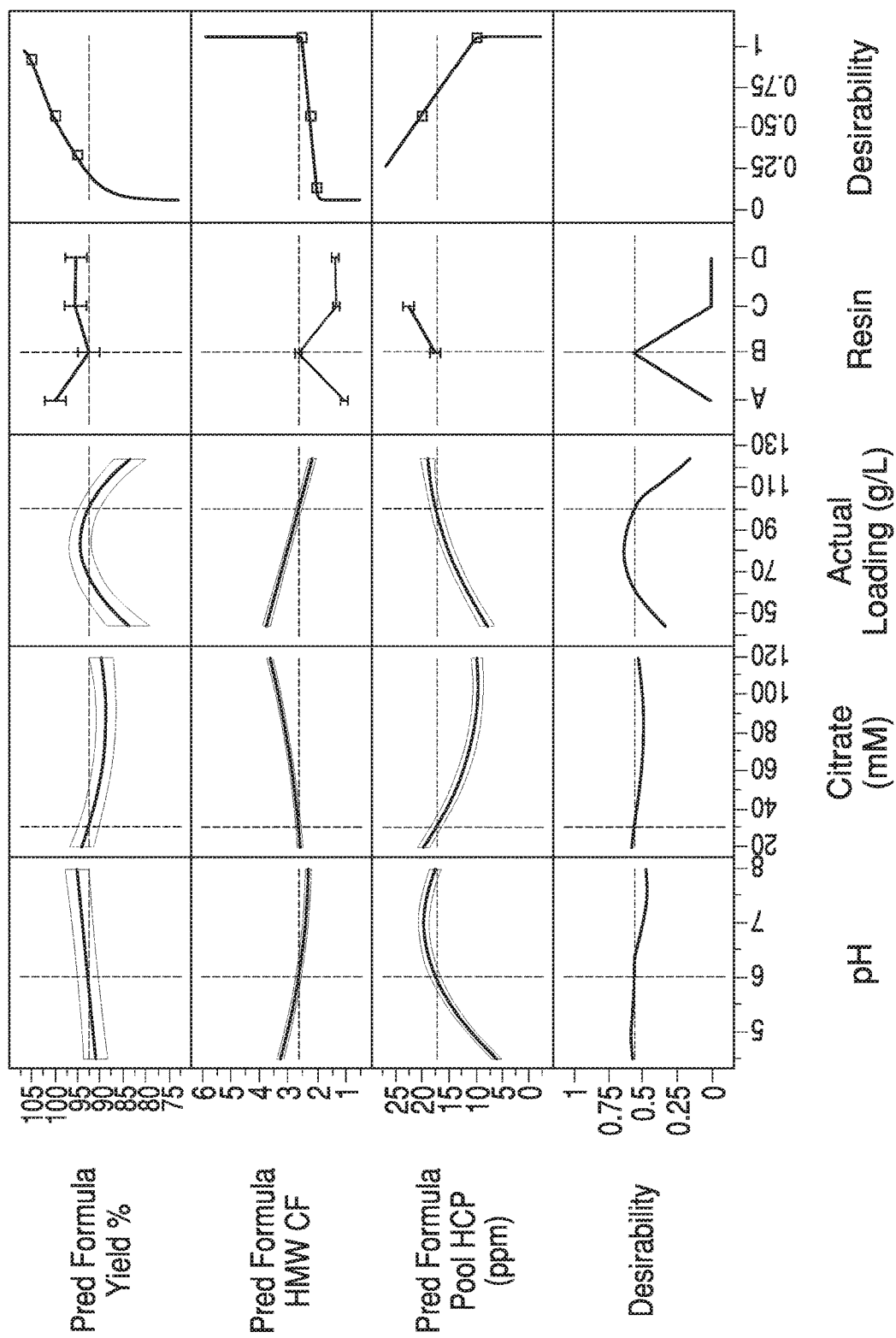
FIG. 22 depicts an exemplary dynamic prediction model, according to aspects of the present disclosure.

One or more transfer functions, boundary functions, and/or predictive models may be combined to develop a dynamic prediction model. Referring to FIG. 22, a dynamic prediction model is shown. The dynamic prediction model calculates how changes to one or more HIC protocol parameters (e.g., pH, citrate concentration, loading mass, chromatography resin) affect quantified properties of the HIC protocol. For example, in the example shown in FIG. 22, then choose protocol parameters include: a pH of 6, a citrate concentration of 30 mM, a loading mass of 100 g per liter of HIC media, and resin C (e.g., Phenyl Sepharose® media). The model then shows how each of these parameters affects the predicted yield, the high molecular weight fraction, and pool host cell protein concentration of the eluate collected using a HIC protocol with the chosen parameters. As shown in FIG. 22, the selected parameters result in a predicted yield of approximately 95%, a high molecular weight fraction of approximately 1.3, and a pool host cell protein concentration of approximately 22.5 ppm. These quantified properties may be used in the evaluation of the HIC protocol and may inform how the protocol parameters affect the product of the HIC protocol. The values for the quantified properties calculated by the dynamic model may update in real-time as protocol parameters are altered.

In some embodiments, an overall desirability may also be calculated as a composite of the quantified properties of the protocol (e.g., a composite of predicted yield, the high molecular weight fraction, and pool host cell protein concentration). Desirability calculations may be based on weighting of quantitative properties of the HIC protocols. For example, changes to a HIC protocol that affect the yield of the protocol may be more important than changes that affect efficiency. The dynamic prediction model may take the relative importance of the quantitative measurements into account, and assign weights to the different measurements so that they unequally affect overall desirability. In some embodiments, the dynamic prediction model may be updated as additional chromatography data (e.g., data from small scale assays, high-throughput screening, and full-scale chromatography runs) is collected and aggregated.

Example 21

Multiple HIC protocols including different target molecules and HIC media combinations, at various pHs, were tested in a gradient elution assay to determine whether such combinations may pose regeneration/usability challenges and whether any of the target molecule and HIC media combinations should be excluded from the development of further HIC protocols.

Wells of a 96-well filter plate (AcroPrep™ Advance 1 mL Filter Plate, 1.2 μm Supor membrane, part #8130, Pall Corporation) were packed with 0.02 μL of various HIC media. Aliquots of load material containing a target molecule were prepared and adjusted to a concentration of 0.33 g/L, to target a concentration of 5 g/L when mixed with the HIC media. For each of the three target antibodies, an aliquot of load material was titrated to several different pH (e.g., 4.5, 6.25, or 8.0) using 2 M acetic acid or 2 M Tris base, to prepare a several aliquots, each including a target antibody and exhibiting a different pH.

Each well of the 96-well plate is packed with a single media type was subjected to a HIC protocol at different pH (4.5, 6.25, or 8.0), to create an array of protocols performed using various combinations of media and pH.

The following steps are performed simultaneously on the array:

1. The wells packed with various HIC resins are equilibrated three times using the equilibration buffer at the respective pH.
2. Load material including the desired target molecule at the respective pH is added to each well and incubated for one hour.
3. The plate is spun at 1100 rpm.
4. Flowthrough (including, for example, components not bound to the media during incubation) is collected.
5. The wells are washed three times using the equilibration buffer at the respective pH for each protocol being tested.
6. A pseudo-elution is performed. Each well is exposed to elution buffer for seven iterations, with the plate being spun at 1100 rpm and eluate being collected after each iteration.
7. The wells are washed twice with NaOH. Different wells of the array may use different concentrations of NaOH. For example, two wells may include the same chromatography media, and were loaded at the same pH, but in one well a 5 mM NaOH wash is used, and in the other well, a 1N NaOH wash is used. After each wash, the plate is spun at 1100 rpm and the wash is collected.
8. The wells are stripped twice with a solution of 6N guanidine HCl, and the stripped material is collected.

For each well, a chromatogram of the target molecule in the material removed from the well (flowthrough, eluent, wash, etc.) was generated. To analyze results, each chromatogram was divided into three zones, where a first zone included the mass of target molecule observed in material removed during steps 2, 3, and 4 (flowthrough, washes, and elution), a second zone included the mass of target molecule observed in material removed during steps 5, 6, 7, (using RODI and NaOH), and a third zone included the mass of target molecule observed in material removed during step 8 (using 6N guanidine HCl).

Figure 23A:
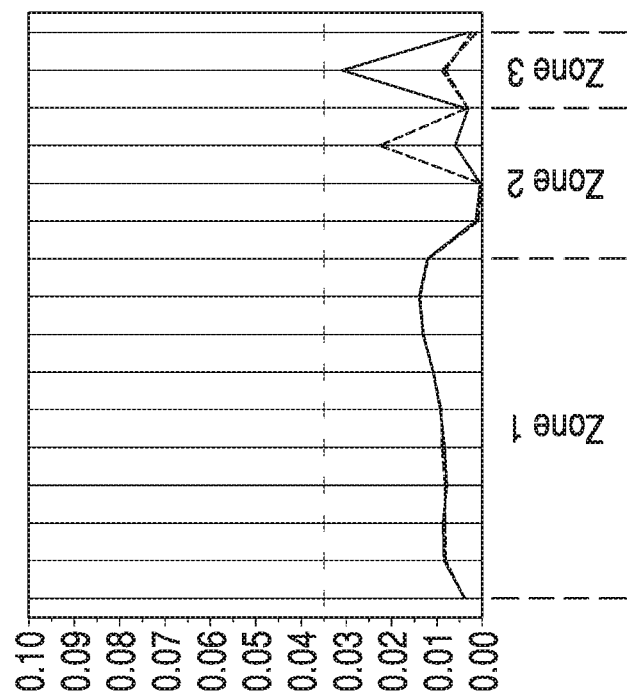
FIGS. 23A-26C depict chromatograms for a first target molecule, generated using multiple hydrophobic interaction chromatography media, pH parameters, and stripping solutions, according to aspects of the present disclosure.
Figure 23B:
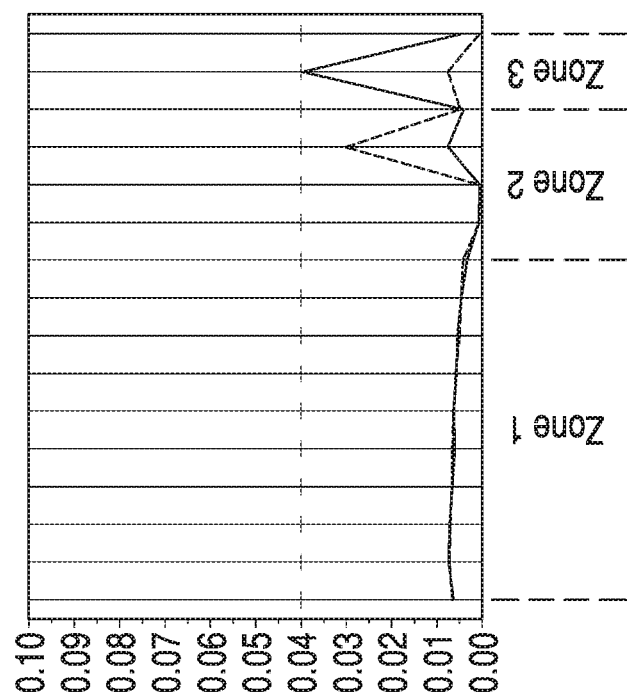
Figure 23C:
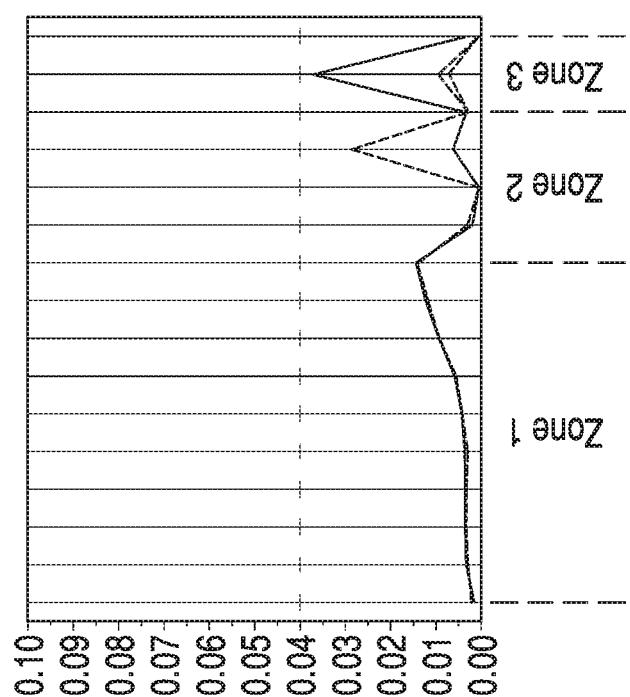
Figure 24A:
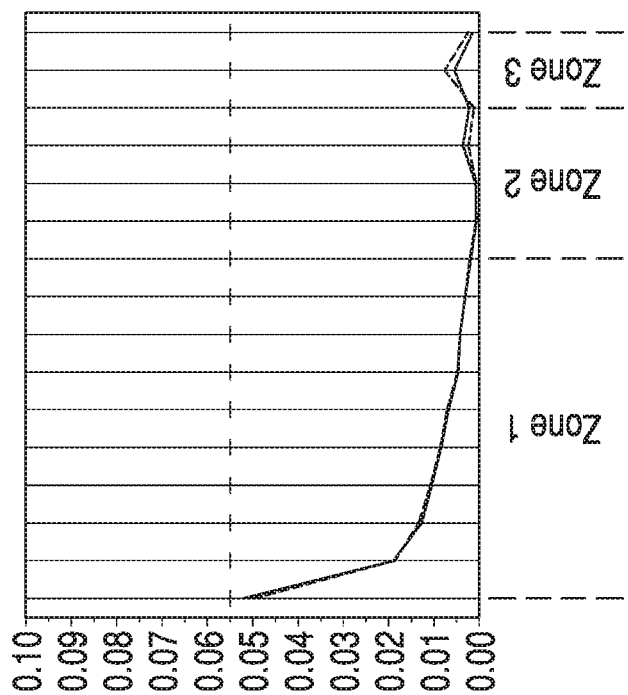
Figure 24B:
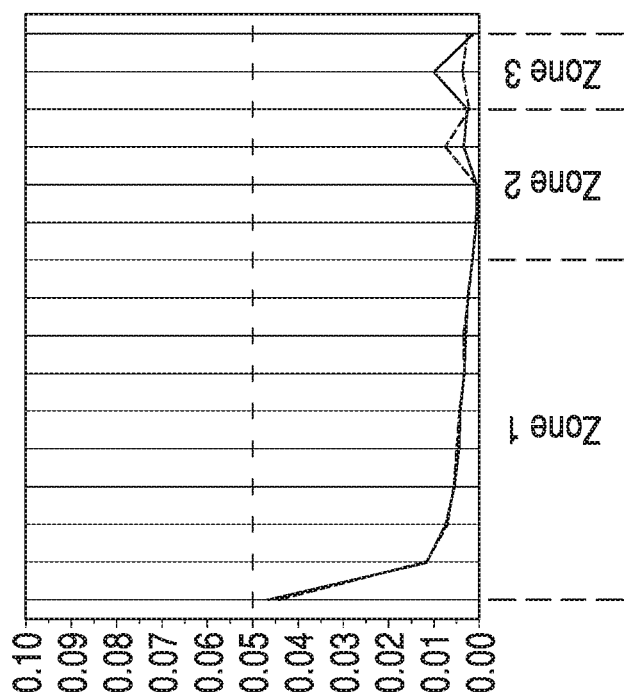
Figure 24C:
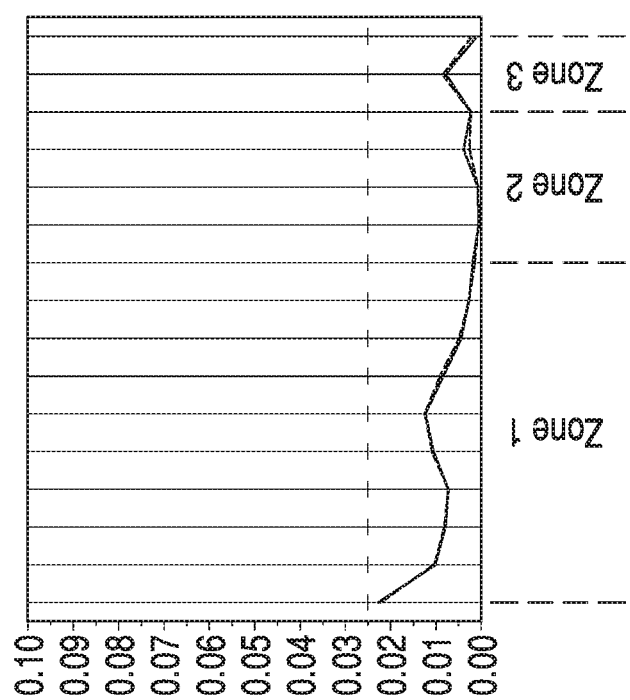
Figure 25A:
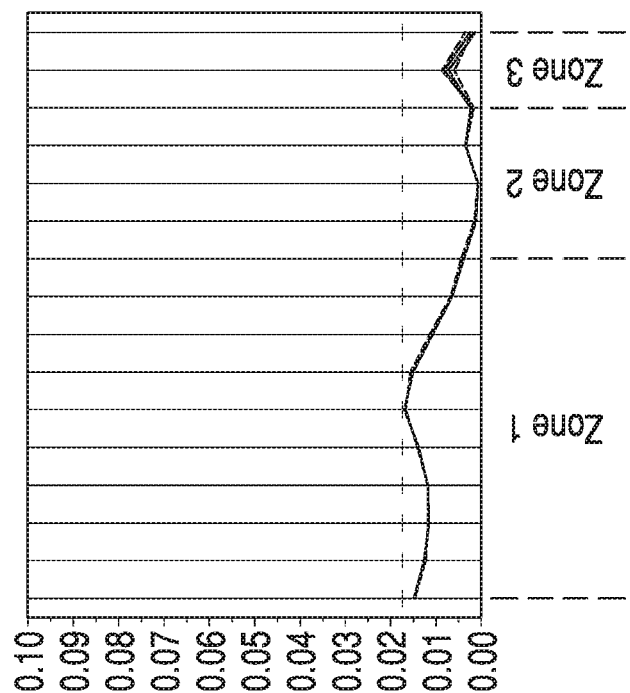
Figure 25B:
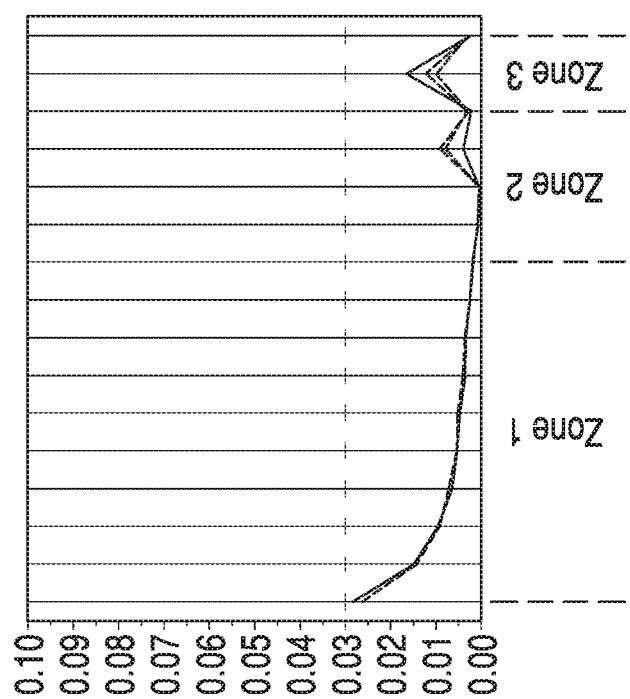
Figure 25C:
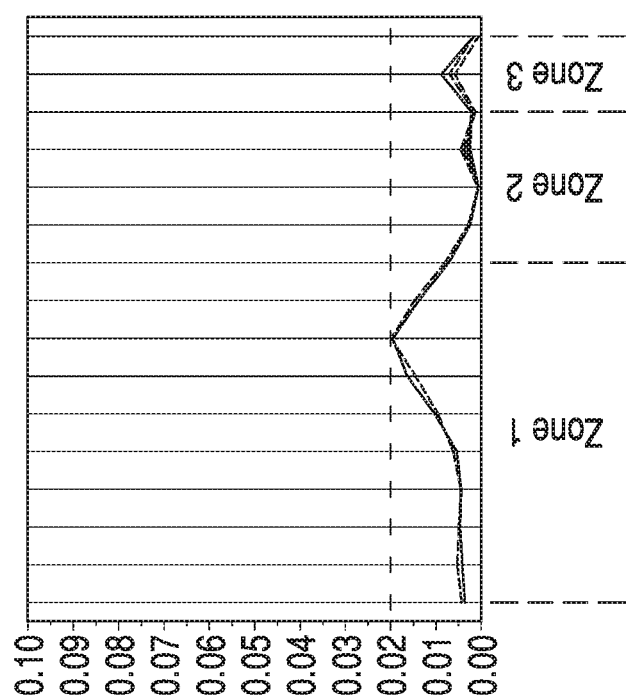
Figure 26A:
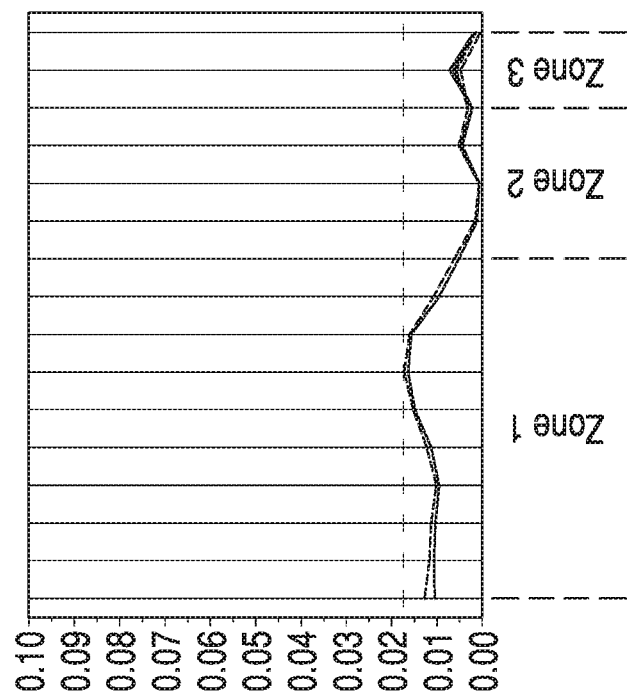
Figure 26B:
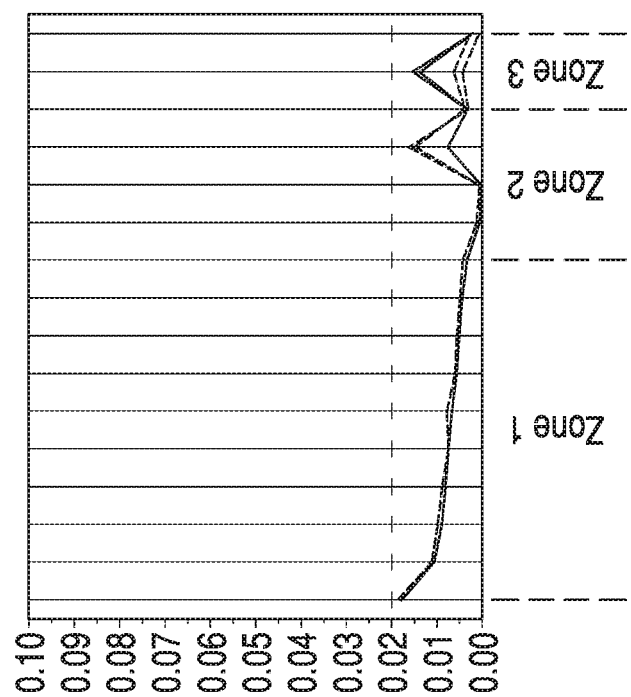
Figure 26C:
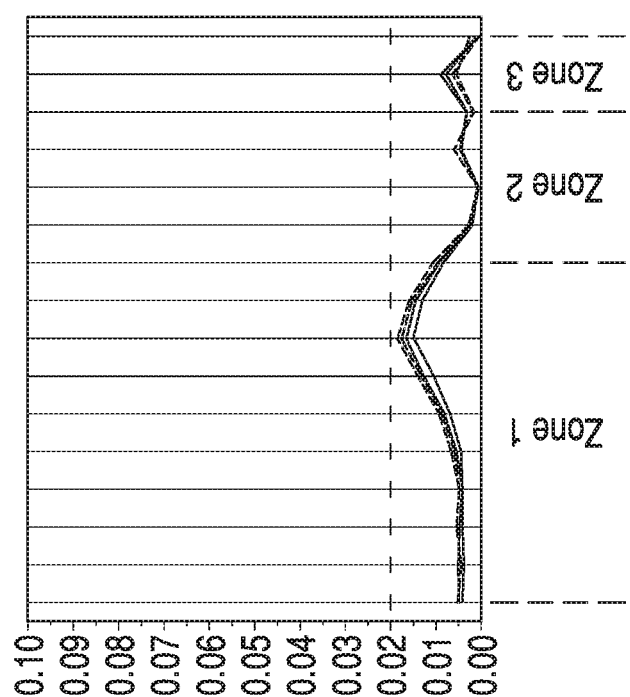

Examples of chromatograms generated from elution assays for a first target molecule are shown in FIGS. 23A-26C. FIGS. 23A-23C show chromatograms of elution assays including the first target molecule on Capto™ Phenyl (High Sub) media, FIGS. 24A-24C show chromatograms of elution assays including the first target molecule on Capto™ Butyl media, FIGS. 25A-C show chromatograms of elution assay including the first target molecule on POROS™ Benzyl media, FIGS. 26A-C show chromatograms of elution assay including the first target molecule on Phenyl Sepharose® media. FIGS. 23A, 24A, 25A, and 26A show chromatograms of the elution assay run at a pH of 4.5, FIGS. 23B, 24B, 25B, and 26B show chromatograms of the elution assay run at a pH of 6.25, and FIGS. 23C, 24C, 25C, and 26C show chromatograms of the elution assay run at a pH of 8. In FIGS. 23A-26C, the dashed line represents chromatograms from elution assays including a 5 mM NaOH wash, and the solid line represents chromatograms from elution assays including a 1 N NaOH wash.

Figure 27A:
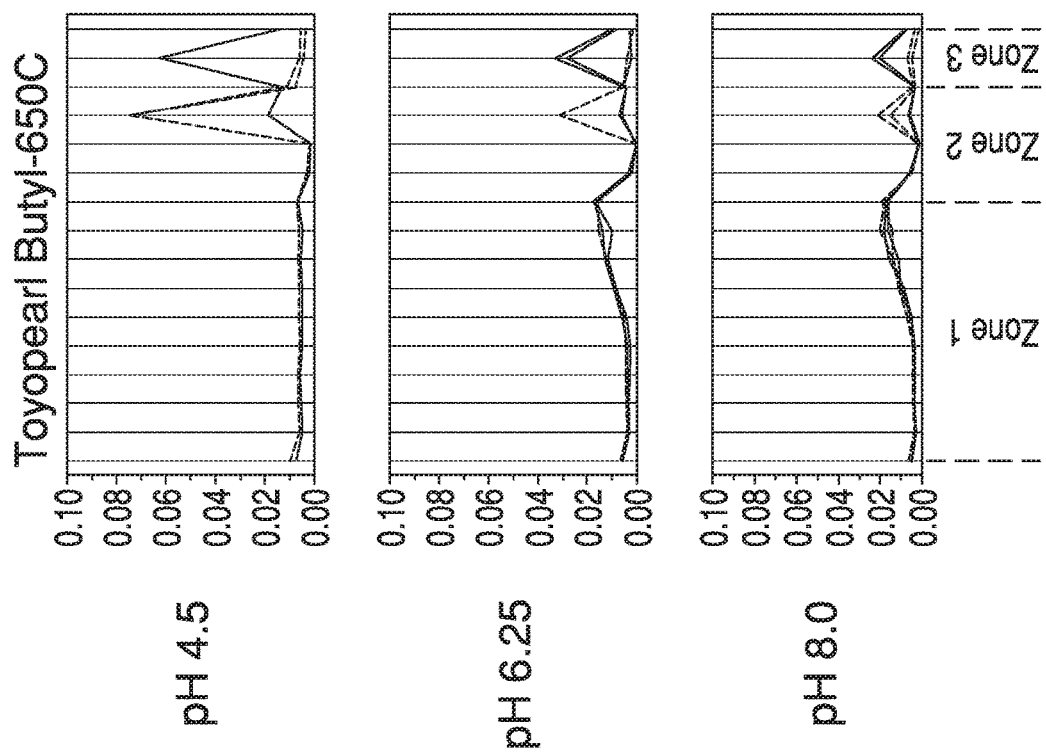
FIGS. 27A-28D depict chromatograms for a second target molecule, generated multiple hydrophobic interaction chromatography media, pH parameters, and stripping solutions, according to aspects of the present disclosure.
Figure 27B:
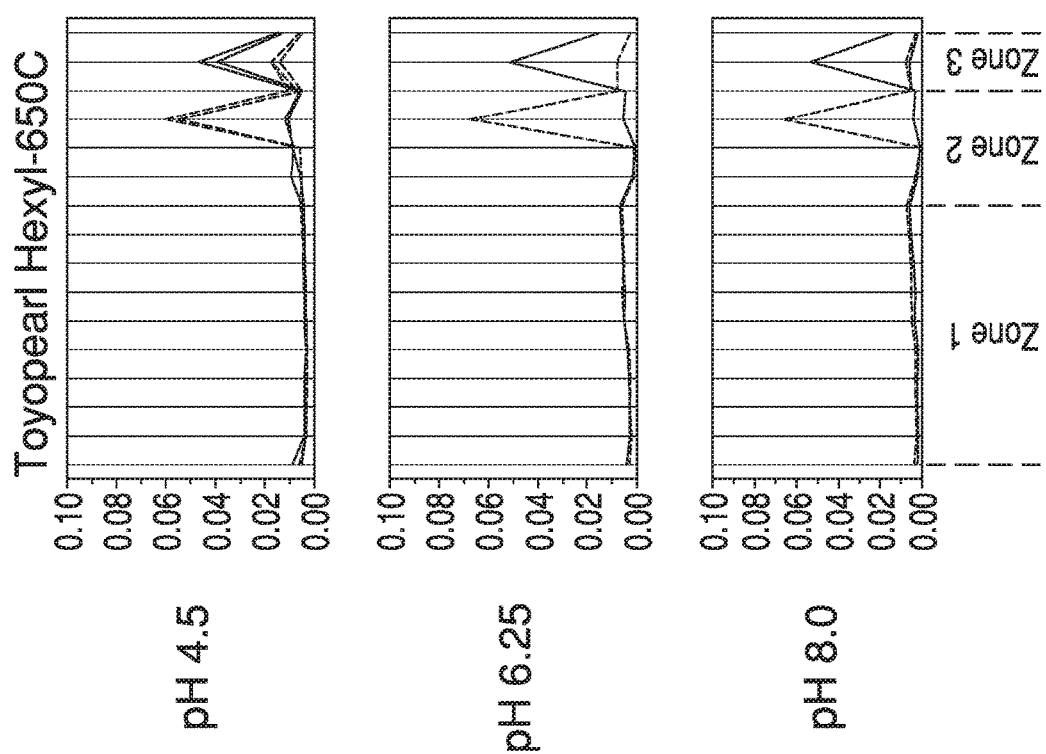
Figures 27C, 27D:
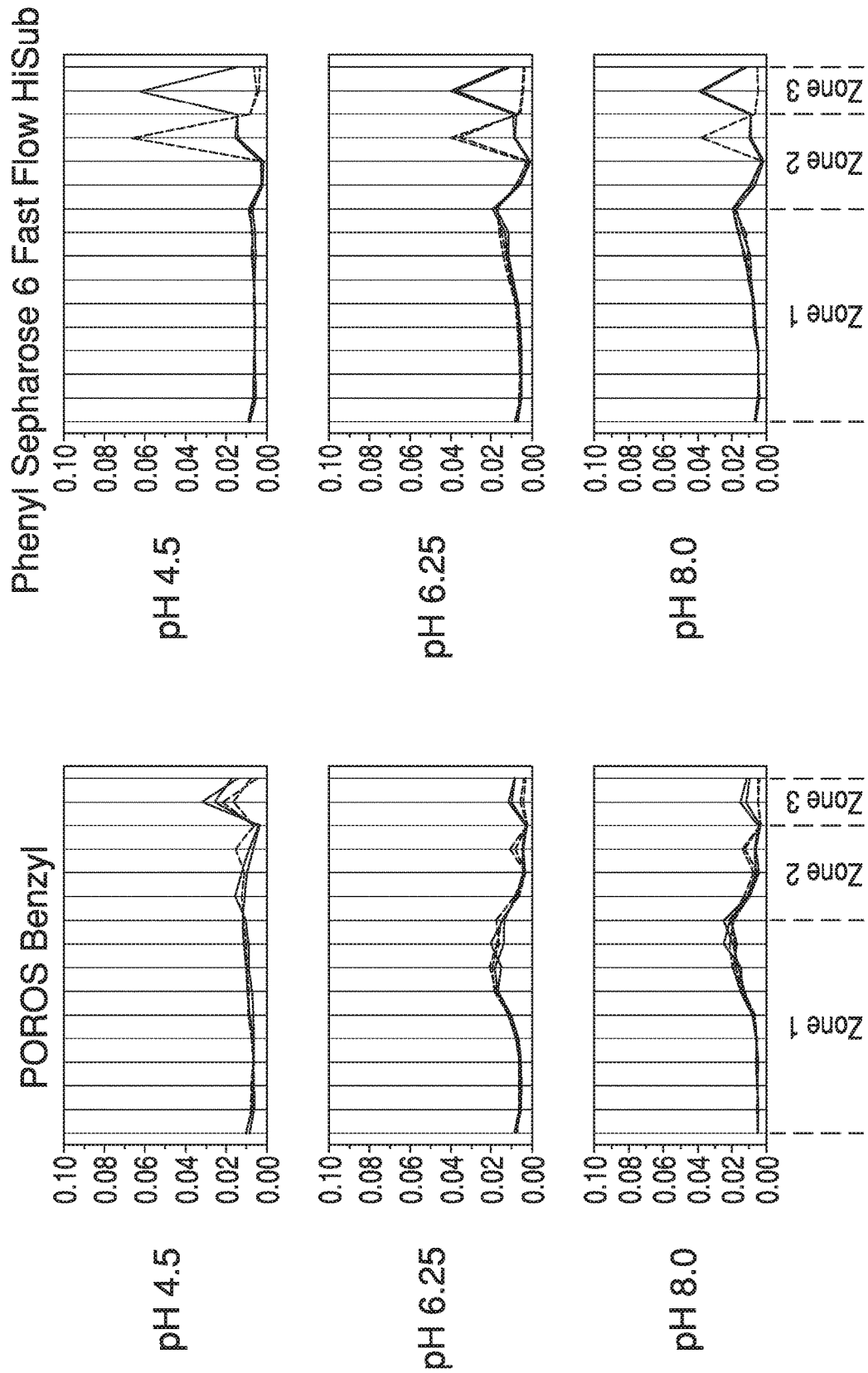
Figure 28B:
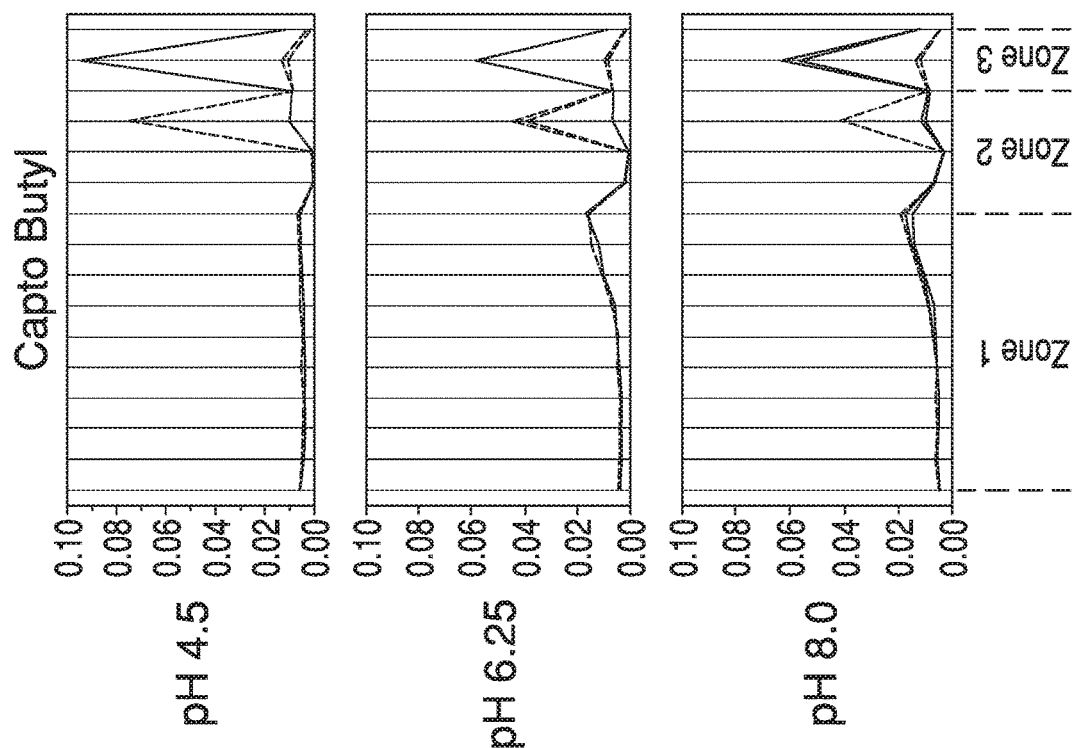
Figure 28A:
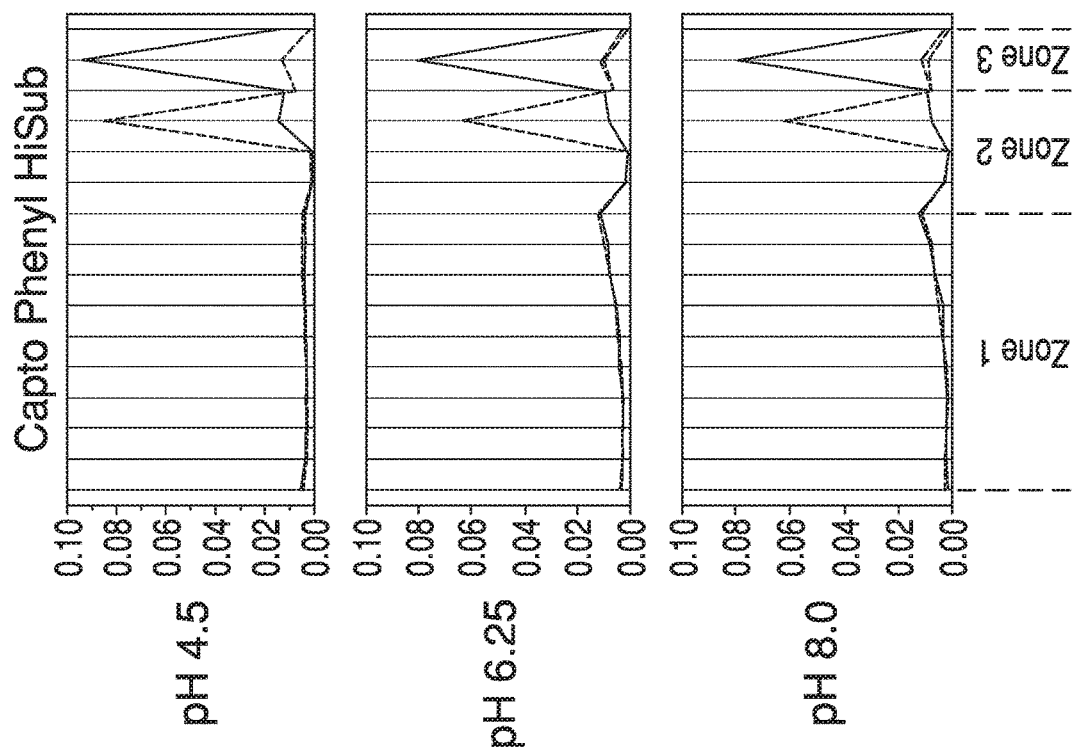
Figure 28D:
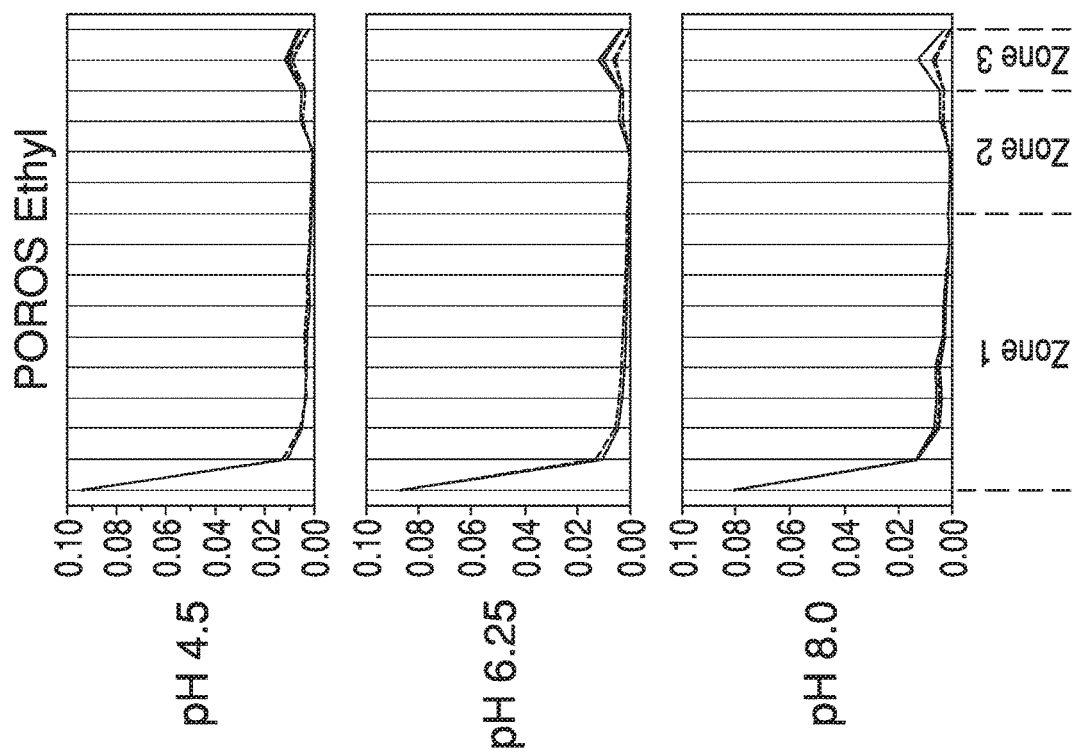
Figure 28C:
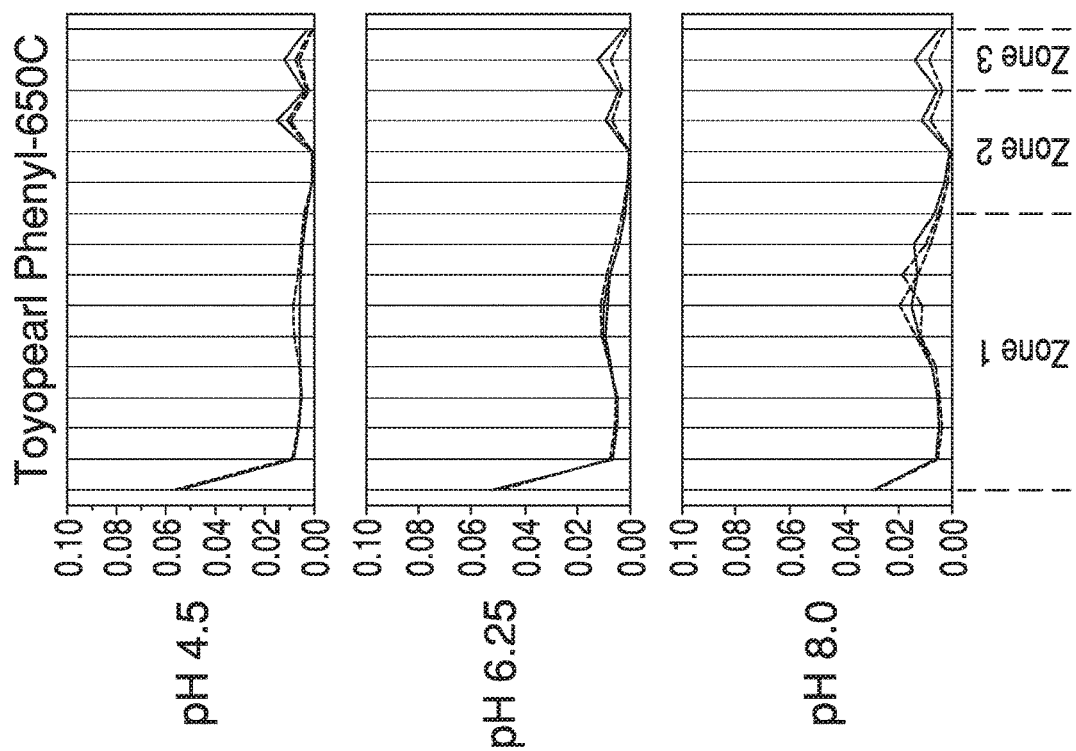

Examples of chromatograms generated from elution assays for a second target molecule are shown in FIGS. 27A-28D. Each figure of FIGS. 27A-28, shows three chromatograms, each from an elution assay run at a different pH. FIG. 27A shows chromatograms from elution assays run on Capto™ Phenyl (High Sub) media, FIG. 27B shows chromatograms from elution assays run on Capto™ Butyl media, FIG. 27C shows chromatograms from elution assays run on TOYOPEARL™ Phenyl-650C media, FIG. 27D shows chromatograms from elution assays run on POROS™ Ethyl media, FIG. 28A shows chromatograms from elution assays run on TOYOPEARL™ Hexyl-650C media, FIG. 28B shows chromatograms from elution assays run on TOYOPEARL™ Butyl-650C media, FIG. 28C shows chromatograms from elution assays run on POROS™ Benzyl media, FIG. 28D shows chromatograms from elution assays run on Phenyl Sepharose® media. In FIGS. 27A-28D, the dashed line represents chromatograms from elution assays including a 5 mM NaOH wash, and the solid line represents chromatograms from elution assays including a 1 N NaOH wash.

As can be seen from the chromatograms, all tested protocols including a 1N NaOH strip included a large percent of target molecule mass than comparable protocols including a 5 mM NaOH strip. That is, more target molecule remained bound to the column after a 1N NaOH strip, compared to the 5 mM NaOH strip.

By comparing chromatograms of different HIC protocols for a given target molecule, certain HIC media and/or pHs may be excluded from consideration. Using a series of elution assays to remove undesirable target molecule, HIC media, and pH combinations from consideration, can improve the speed at which HIC protocol are developed and tested. For example, chromatograms that indicate over 5% (e.g., over 10%) of the target molecule was eluted in Zone 3, may indicate that the given HIC media, pH, and target molecule combination is not suitable for integration into a HIC protocol.

In addition to excluding HIC media, pH, and target molecules from consideration using elution assays, the Zone 3 mass calculated from the chromatograms may be transformed via a transfer function to predict the mass of target molecules eluted in Zone 3 during a full-scale chromatography run. This predicted mass may also be used to exclude combinations of HIC media, pHs, and target molecules from consideration. An exemplary listing of calculated Zone 3 target molecule recoveries for a given target molecule in a series of HIC protocols using various combinations HIC media and pH is shown in Table 14.

TABLE 14

| HIC Media | pH | Zone 3 Normalized Recovery | Predicted Full-Scale Zone 3 Recovery |
|---|---|---|---|
| Capto ™ Phenyl (High Sub) | 4.5 | 38.2% | 10.6% |
| Capto ™ Phenyl (High Sub) | 6.25 | 24.0% | −3.1% |
| Capto ™ Phenyl (High Sub) | 8 | 36.1% | 9.1% |
| Capto ™ Butyl | 4.5 | 10.1% | 4.9% |
| Capto ™ Butyl | 6.25 | 4.6% | 4.6% |
| Capto ™ Butyl | 8 | 8.6% | 4.9% |
| POROS ™ Benzyl | 4.5 | 18.0% | 5.7% |
| POROS ™ Benzyl | 6.25 | 6.9% | 1.5% |
| POROS ™ Benzyl | 8 | 9.9% | −0.3% |
| Phenyl Sepharose ® | 4.5 | 15.7% | 1.6% |
| Phenyl Sepharose ® | 6.25 | 6.3% | 0.0% |
| Phenyl Sepharose ® | 8 | 9.7% | 0.6% |

As can be seen in Table 14, an elution assay including the given target molecule on Capto™ Phenyl (High Sub) media at a pH of 4.5 resulted in a normalized percent recovery of 38.2%. This result, when transformed through the transfer function, results in a predicted full-scale Zone 3 recovery of 10.6%. In embodiments where a pre-determined threshold is 10%, this would be greater than the threshold, and therefore, the combination of the target molecule, Capto™ Phenyl (High Sub) media, and a pH of 4.5 would be excluded from the development of further HIC protocols. In some embodiments, if exclusion of a media and pH combination for a given target molecule is warranted, that media and pH combination may also be excluded from the development of further protocols including other target molecules.

Those skilled in the art will appreciate that the conception upon which this disclosure is based may readily be used as a basis for designing other methods and systems for carrying out the several purposes of the present disclosure. Accordingly, the claims are not to be considered as limited by the foregoing description.

What is claimed is:

1. A method of regenerating a hydrophobic interaction chromatography column to which a load mass has been applied, the method comprising:
passing one or more column volumes of an alkaline solution through hydrophobic interaction media within the column, wherein the alkaline solution exhibits a pH of between about 10 and about 14, and a conductivity of between about 0.5 mS/cm and about 10 mS/cm,
wherein material bound to the hydrophobic interaction media is removed.

2. The method of claim 1, wherein the alkaline solution includes one of sodium hydroxide, potassium hydroxide, calcium hydroxide, magnesium hydroxide, or Tris.

3. The method of claim 1, wherein the alkaline solution exhibits a conductivity of between about 0.8 mS/cm and about 1.6 mS/cm, and/or the alkaline solution includes a total dissolved salt concentration of between about 0.1 mM and about 10 mM.

4. The method of claim 1, wherein the material removed from the media includes host cell proteins, aggregated proteins, lipids, polypeptide fragments, biomolecules, or nucleic acids, and/or after removal of material bound to the hydrophobic interaction media, less than about 1.0% of the load mass remains bound to the hydrophobic interaction media as a residual mass.

5. The method of claim 1, wherein the material removed from the media does not include bacteria or fungi.

6. The method of claim 1, wherein the method does not include contacting the hydrophobic interaction media with a chaotropic agent or an organic solvent.

7. The method of claim 1, wherein the step of passing the one or more column volumes of an alkaline solution through the hydrophobic interaction media within the column takes between about 10 minutes and about 1 hour.

8. A method of regenerating a chromatography column to which a load mass has been applied, the method comprising:
passing one or more column volumes of an alkaline solution through media within the column, wherein the alkaline solution includes sodium hydroxide at a total dissolved concentration of between about 0.5 mM and about 50 mM, and a conductivity of between about 0.5 mS/cm and about 10 mS/cm,
wherein material bound to the media is removed.

9. The method of claim 8, wherein the media include a matrix comprising ligands having between 2 and 10 hydrocarbons in an aliphatic or aromatic configuration, and the ligands are present in the media at a density of between about 20 and about 30 μmol per ml of media.

10. The method of claim 8, wherein the media do not include ligands including 30 or more hydrocarbons.

11. The method of claim 8, wherein the chromatography column is not used in a mixed-mode chromatography process.

12. The method of claim 8, wherein the media include a matrix comprising cross-linked agarose and phenyl ligands.

13. The method of claim 8, wherein the method does not include contacting the media with alcohol, ethylene glycol, or sodium chloride.

14. The method of claim 8, further comprising:
after passing the one or more column volumes of the alkaline solution through the column, passing one or more column volumes of a chaotropic agent through the column, wherein the chaotropic agent is one of 6N guanidine hydrochloride or 8N urea.

15. A method of preparing a chromatography column for storage, comprising:
performing the method of claim 8; and
contacting the column with a storage buffer comprising sodium hydroxide at a total dissolved concentration of between about 0.05M and about 0.15M.

16. A method for reusing a chromatography column, the method comprising:
applying a first load mass to the chromatography column;
performing the method of claim 8 to the chromatography column; and
applying a second load mass to the chromatography column, wherein the method does not include cleaning the chromatography column.

17. The method of claim 1, wherein the material bound to the hydrophobic interaction media includes a target molecule, wherein the target molecule is dupilumab.

18. The method of claim 1, wherein the material bound to the hydrophobic interaction media includes a target molecule, wherein the target molecule is an anti-interleukin 4 receptor antibody.

19. The method of claim 8, wherein the material bound to the media includes a target molecule, wherein the target molecule is dupilumab.

20. The method of claim 8, wherein the material bound to the media includes a target molecule, wherein the target molecule is an anti-interleukin 4 receptor antibody.

21. The method of claim 1, wherein the load mass comprises dupilumab.

22. The method of claim 1, wherein the load mass comprises an anti-interleukin 4 receptor antibody.

23. The method of claim 8, wherein the load mass comprises dupilumab.

24. The method of claim 8, wherein the load mass comprises an anti-interleukin 4 receptor antibody.

* * * * *